(12) United States Patent
Stoessel et al.

(10) Patent No.: US 9,331,290 B2
(45) Date of Patent: May 3, 2016

(54) METAL COMPLEXES

(75) Inventors: Philipp Stoessel, Frankfurt am Main (DE); Dominik Joosten, Frankfurt am Main (DE); Anja Gerhard, Egelsbach (DE); Esther Breuning, Ober-Ramstadt (DE)

(73) Assignee: Merck Patent GmbH (DE)

( * ) Notice: Subject to any disclaimer, the term of this patent is extended or adjusted under 35 U.S.C. 154(b) by 476 days.

(21) Appl. No.: 13/809,913

(22) PCT Filed: Jun. 17, 2011

(86) PCT No.: PCT/EP2011/002985
§ 371 (c)(1),
(2), (4) Date: Jan. 14, 2013

(87) PCT Pub. No.: WO2012/007086
PCT Pub. Date: Jan. 19, 2012

(65) Prior Publication Data
US 2013/0112920 A1    May 9, 2013

(30) Foreign Application Priority Data

Jul. 16, 2010  (DE) .......................... 10 2010 027 317

(51) Int. Cl.
| | |
|---|---|
| H01L 51/00 | (2006.01) |
| C07D 487/02 | (2006.01) |
| C07D 487/12 | (2006.01) |
| C07F 15/00 | (2006.01) |
| C09K 11/06 | (2006.01) |
| H05B 33/14 | (2006.01) |
| H01L 51/50 | (2006.01) |

(52) U.S. Cl.
CPC .......... *H01L 51/0085* (2013.01); *C07D 487/02* (2013.01); *C07D 487/12* (2013.01); *C07F 15/0033* (2013.01); *C09K 11/06* (2013.01); *H01L 51/0087* (2013.01); *H05B 33/14* (2013.01); *C09K 2211/1029* (2013.01); *C09K 2211/1044* (2013.01); *C09K 2211/1059* (2013.01); *C09K 2211/1092* (2013.01); *C09K 2211/185* (2013.01); *H01L 51/0059* (2013.01); *H01L 51/0067* (2013.01); *H01L 51/0072* (2013.01); *H01L 51/0077* (2013.01); *H01L 51/5016* (2013.01); *Y02E 10/549* (2013.01)

(58) Field of Classification Search
None
See application file for complete search history.

(56) References Cited

U.S. PATENT DOCUMENTS

| | | |
|---|---|---|
| 2010/0141125 A1 | 6/2010 | Otsu et al. |
| 2010/0141126 A1 | 6/2010 | Otsu et al. |
| 2011/0284799 A1 | 11/2011 | Stoessel et al. |

FOREIGN PATENT DOCUMENTS

| | | |
|---|---|---|
| JP | 2010-028014 A | 2/2010 |
| JP | 2010-118591 A | 5/2010 |
| JP | 2010-141008 A | 6/2010 |
| JP | 2010272727 A | 12/2010 |
| WO | WO-2007/095118 A2 | 8/2007 |
| WO | WO-2008/140114 A1 | 11/2008 |
| WO | WO-2008/140115 A1 | 11/2008 |
| WO | WO-2008/143059 A1 | 11/2008 |
| WO | WO-2010/004887 A1 | 1/2010 |
| WO | WO-2010/086089 A1 | 8/2010 |

OTHER PUBLICATIONS

Caplus Database, XP002658735, (2010).
International Search Report for PCT/EP2011/002985 mailed Oct. 10, 2011.

*Primary Examiner* — Bijan Ahvazi
*Assistant Examiner* — Catherine S Branch
(74) *Attorney, Agent, or Firm* — Drinker Biddle & Reath LLP

(57) ABSTRACT

The present invention relates to metal complexes and to electronic devices, in particular organic electro-luminescent devices, comprising these metal complexes. M(L)n(L')m formula (1), where the compound contains a moiety M(L)n of the formula (2).

26 Claims, No Drawings

METAL COMPLEXES

CROSS-REFERENCE TO RELATED APPLICATIONS

This application is a national stage application (under 35 U.S.C. §371) of PCT/EP2011/002985, filed Jun. 17, 2011, which claims benefit of German application 10 2010 027 317.1, filed Jul. 16, 2010 which are both incorporated by reference.

The present invention relates to metal complexes which are suitable for use as emitters in organic electroluminescent devices.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organometallic complexes which exhibit phosphorescence instead of fluorescence (M. A. Baldo et al., Appl. Phys. Lett. 1999, 75, 4-6). For quantum-mechanical reasons, an up to four-fold energy and power efficiency is possible using organometallic compounds as phosphorescence emitters. In general, there is still a need for improvement in OLEDs which exhibit triplet emission, in particular with respect to efficiency, operating voltage and lifetime.

The prior art discloses iridium complexes which contain imidazophenanthridine derivatives or diimidazoquinazoline derivatives as ligands (WO 2007/095118). When used in organic electroluminescent devices, these complexes exhibit, in particular, blue and green phosphorescence. Further improvements are still desirable here with respect to efficiency, operating voltage and lifetime. Furthermore, there is still a need for improvement here, in particular, with respect to the colour coordinates in order to be able to achieve yellow, orange or red emission.

WO 2010/086089 discloses metal complexes which contain imidazoisoquinoline derivatives as ligands. Using complexes of this type, good advances have already been achieved in the development of triplet emitters, in particular triplet emitters which exhibit blue emission. However, further improvements are also still desirable here with respect to efficiency, operating voltage and lifetime. In particular, there is still a need for improvement here with respect to the colour coordinates in order to be able to achieve green, yellow, orange or red emission using structures of this type.

The object of the present invention is therefore the provision of novel metal complexes which are suitable as emitters for use in OLEDs. In particular, the object is to provide emitters which are suitable for green-, yellow-, orange- or red-phosphorescent OLEDs and which at the same time exhibit good properties with respect to efficiency, operating voltage, lifetime and colour coordinates.

Surprisingly, it has been found that certain metal chelate complexes described in greater detail below achieve this object and result in improvements in the organic electroluminescent device. These metal complexes are accessible in high yield. The present invention therefore relates to these metal complexes and to organic electroluminescent devices which comprise these complexes.

The invention thus relates to a compound of the formula (1), $$M(L)_n(L')_m \qquad \text{formula (1)}$$

where the compound of the general formula (1) contains a moiety $M(L)_n$ of the formula (2):

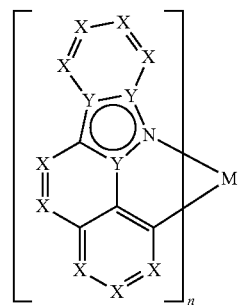

formula (2)

where the following applies to the symbols and indices used:

M is a metal;

Y is on each occurrence, identically or differently, C or N, with the proviso that precisely one symbol Y in each ligand stands for N and the other two symbols Y stand for C;

X is on each occurrence, identically or differently, CR or N;

R is on each occurrence, identically or differently, H, D, F, Cl, Br, I, $N(R^1)_2$, CN, $NO_2$, OH, COOH, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which may be substituted by one or more radicals $R^1$, where one or more non-adjacent $CH_2$ groups may be replaced by $R^1C=CR^1$, $C\equiv C$, $Si(R^1)_2$, $C=O$, $NR^1$, O, S or $CONR^1$ and where one or more H atoms may be replaced by D, F, Cl, Br, I or CN, or an aromatic or heteroaromatic ring system having 5 to 60 aromatic ring atoms, which may in each case be substituted by one or more radicals $R^1$, or an aryloxy or heteroaryloxy group having 5 to 40 aromatic ring atoms, which may be substituted by one or more radicals $R^1$, or an aralkyl or heteroaralkyl group having 5 to 40 aromatic ring atoms, which may be substituted by one or more radicals $R^1$, or a diarylamino group, diheteroarylamino group or arylheteroarylamino group having 10 to 40 aromatic ring atoms, which may be substituted by one or more radicals $R^1$; two adjacent radicals R here may also form a mono- or polycyclic, aliphatic, aromatic and/or benzo-fused ring system with one another;

$R^1$ is on each occurrence, identically or differently, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which may be substituted by one or more radicals $R^2$, where one or more non-adjacent $CH_2$ groups may be replaced by $R^2C=CR^2$, $C\equiv C$, $Si(R^2)_2$, $C=O$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 40 aromatic ring atoms, which may be substituted by one or more radicals $R^2$, or an aralkyl or heteroaralkyl group having 5 to 40 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals R²; two or more adjacent radicals R¹ here may form a mono- or polycyclic, aliphatic, aromatic and/or benzo-fused ring system with one another;

R² is on each occurrence, identically or differently, H, D, F or an aliphatic, aromatic and/or heteroaromatic hydrocarbon radical having 1 to 20 C atoms, in which, in addition, one or more H atoms may be replaced by F; two or more substituents R² here may also form a mono- or polycyclic, aliphatic ring system with one another;

L' is, identically or differently on each occurrence, any desired co-ligand;

n is 1, 2 or 3;

m is 0, 1, 2, 3 or 4;

a plurality of ligands L here may also be linked to one another or L may be linked to L' via a single bond or any desired bridge V and thus form a tridentate, tetradentate, pentadentate or hexadentate ligand system and/or a substituent R may additionally be coordinated to the metal;

the two following compounds are excluded from the invention:

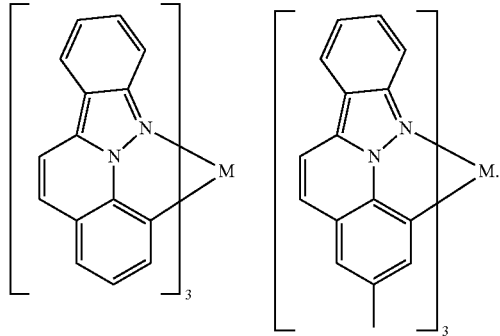

The circle in the five-membered ring in the moiety of the formula (2) denotes that it is a heteroaromatic group having 6 π electrons. The nitrogen here contributes two u electrons and the carbon and each of the groups Y each contribute one u electron to the π-electron system as a whole.

In the complexes of the formula (1), the indices n and m are selected so that the coordination number on the metal M corresponds overall, depending on the metal, to the usual coordination number for this metal. This is usually the coordination number 4, 5 or 6 for transition metals, depending on the metal. It is generally known that metal coordination compounds have different coordination numbers, i.e. bind a different number of ligands, depending on the metal and on the oxidation state of the metal. Since the preferred coordination numbers of metals and metal ions in various oxidation states belong to the general expert knowledge of the person skilled in the art in the area of organometallic chemistry or coordination chemistry, it is readily possible for the person skilled in the art to use a suitable number of ligands, depending on the metal and its oxidation state and depending on the precise structure of the ligand L, and thus to select the indices n and m suitably.

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

An aromatic ring system in the sense of this invention contains 6 to 60 C atoms in the ring system. A heteroaromatic ring system in the sense of this invention contains 1 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, a C, N, O or Si atom or a carbonyl group. Thus, for example, systems such as 9,9'-spirobifluorene, 9,9-diarylfluorene, triarylamine, diaryl ether, stilbene, etc., are also intended to be taken to be aromatic ring systems for the purposes of this invention, as are systems in which two or more aryl groups are interrupted, for example, by a linear or cyclic alkyl group or by a silyl group. Furthermore, systems in which two or more aryl or heteroaryl groups are bonded directly to one another, such as, for example, biphenyl or terphenyl, are likewise intended to be taken to be an aromatic or heteroaromatic ring system.

An aralkyl group in the sense of the present invention is an alkyl group which is substituted by at least one aryl or heteroaryl group in accordance with the definition given above.

A cyclic alkyl, alkoxy or thioalkoxy group in the sense of this invention is taken to mean a monocyclic, bicyclic or polycyclic group.

For the purposes of the present invention, a $C_1$- to $C_{40}$-alkyl group, in which, in addition, individual H atoms or $CH_2$ groups may be substituted by the above-mentioned groups, is taken to mean, for example, the radicals methyl, ethyl, n-propyl, i-propyl, n-butyl, i-butyl, s-butyl, t-butyl, 2-methylbutyl, n-pentyl, s-pentyl, tert-pentyl, 2-pentyl, neopentyl, cyclopentyl, n-hexyl, s-hexyl, tert-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo-[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl or 2,2,2-trifluoroethyl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, sbutoxy, t-butoxy or 2-methylbutoxy.

An aromatic or heteroaromatic ring system having 5-60 aromatic ring atoms, which may also in each case be substituted by the radicals R mentioned above and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or transindenofluorene, cis- or trans-monobenzoindenofluorene, cis- or transdibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

The compounds of the formula (1) may be charged or uncharged. If the compounds of the formula (1) are charged, they also have one or more counterions. Examples of cationic counterions are alkali metal ions, for example lithium, sodium or potassium, tetraalkylammonium or tetraalkylphosphonium ions, where the alkyl groups each preferably contain 1 to 4 C atoms. Examples of anionic counterions are chloride, bromide, iodide, sulfate, phosphate, tetrafluoroborate or hexafluorophosphate.

Preference is given to compounds of the formula (1), characterised in that they are uncharged, i.e. are electrically neutral. This is achieved in a simple manner by selecting the charges of the ligands L and L' in such a way that they compensate for the charge of the complexed metal atom M.

Preference is furthermore given to compounds of the formula (1), characterised in that the sum of the valence electrons around the metal atom is 16 in tetracoordinated complexes and 16 or 18 in pentacoordinated complexes and 18 in hexacoordinated complexes. This preference is due to the particular stability of these metal complexes.

In a preferred embodiment of the invention, M stands for a transition metal, where lanthanides and actinides are excluded, or for a main-group metal. If M stands for a main-group metal, it preferably stands for a metal from the third, fourth or fifth main group, in particular for tin.

Preference is given to compounds of the formula (1) in which M stands for a transition metal, where lanthanides and actinides are excluded, in particular for a tetracoordinated, pentacoordinated or hexacoordinated transition metal, particularly preferably selected from the group consisting of chromium, molybdenum, tungsten, rhenium, ruthenium, osmium, rhodium, iridium, nickel, palladium, platinum, copper, silver and gold, in particular molybdenum, tungsten, rhenium, ruthenium, osmium, iridium, copper, platinum and gold. Very particular preference is given to iridium and platinum. The metals here can be in various oxidation states. The above-mentioned metals are preferably in the oxidation states Cr(0), Cr(II), Cr(III), Cr(IV), Cr(VI), Mo(0), Mo(II), Mo(III), Mo(IV), Mo(VI), W(0), W(II), W(III), W(IV), W(VI), Re(I), Re(II), Re(III), Re(IV), Ru(II), Ru(III), Os(II), Os(III), Os(IV), Rh(I), Rh(III), Ir(I), Ir(III), Ir(IV), Ni(0), Ni(II), Ni(IV), Pd(II), Pt(II), Pt(IV), Cu(I), Cu(II), Cu(III), Ag(I), Ag(II), Au(I), Au(III) and Au(V). Particular preference is given to Mo(0), W(O), Re(I), Ru(II), Os(II), Rh(III), Cu(I), Ir(III) and Pt(II). Very particular preference is given to Ir(III) and Pt(II).

In a preferred embodiment of the invention, M is a tetracoordinated metal, and the index n stands for 1 or 2. If the index n=1, one bidentate or two monodentate ligands L', preferably one bidentate ligand L', are also coordinated to the metal M. If the index n=2, the index m=0. A preferred tetracoordinated metal is Pt(II).

In a further preferred embodiment of the invention, M is a hexacoordinated metal, and the index n stands for 1, 2 or 3, preferably for 2 or 3. If the index n=1, four monodentate or two bidentate or one bidentate and two monodentate or one tridentate and one monodentate or one tetradentate ligand L', preferably two bidentate ligands L', are also coordinated to the metal. If the index n=2, one bidentate or two monodentate ligands L', preferably one bidentate ligand L', are also coordinated to the metal. If the index n=3, the index m=0. A preferred hexacoordinated metal is Ir(III).

In the ligand L, preferably all groups X stand for CR or precisely one, two, three or four groups X, particularly preferably one, two or three groups X, very particularly preferably one or two groups X, stand for N. Especially preferably, all groups X stand for CR or precisely one group X stands for N and the other groups X stand for CR.

If the ligand L stands for the following formula (3), it is preferred for at least one group X to stand for N:

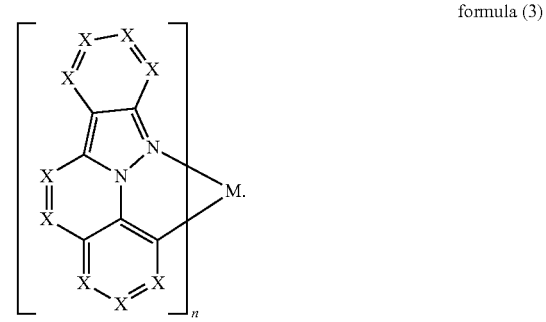

formula (3)

If all groups X stand for CR, the moieties of the formula (2) are selected from the moieties of the following formulae (4), (5) and (6),

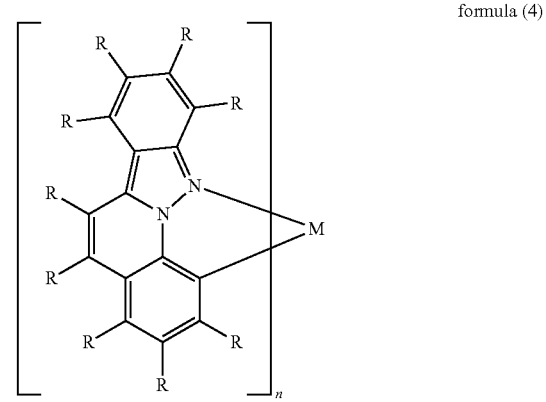

formula (4)

formula (5)
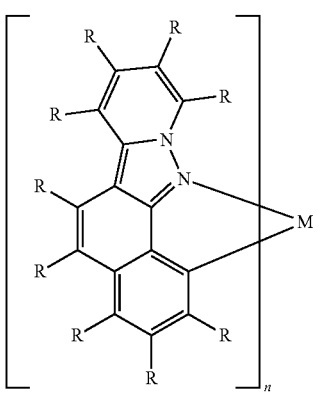
formula (6)
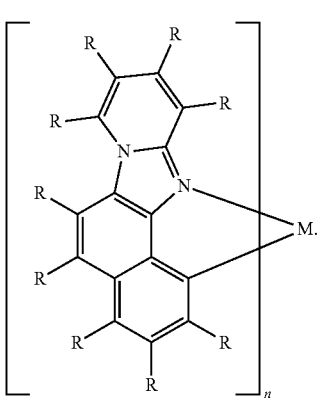
If precisely one group X stands for N, preferred moieties of the formula (2) are the moieties of the following formulae (7) to (33),
formula (7)
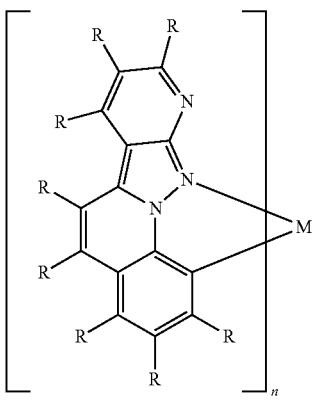
formula (8)
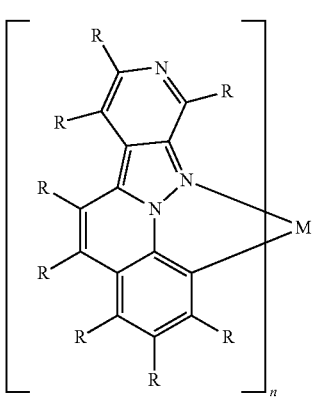
formula (9)
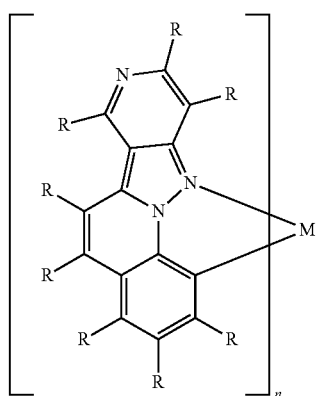
formula (10)
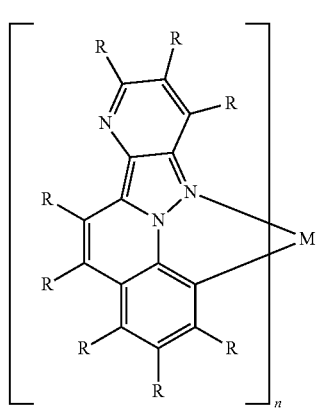
formula (11)
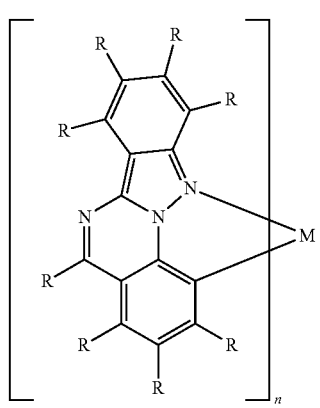
formula (12)
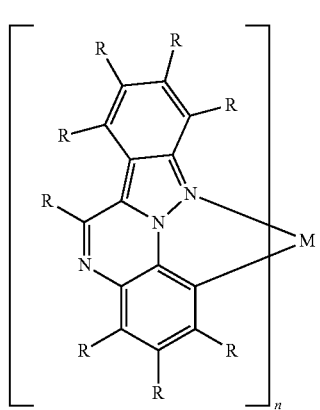

formula (13)
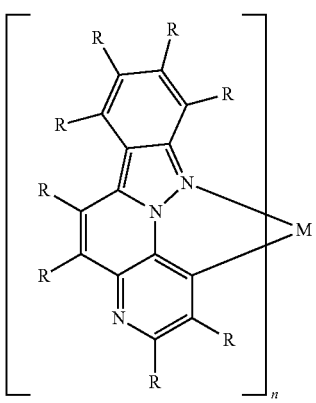
formula (14)
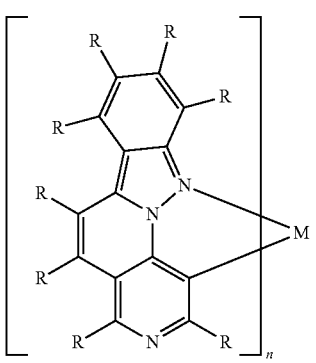
formula (15)
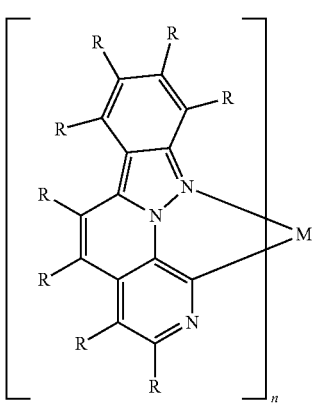
formula (16)
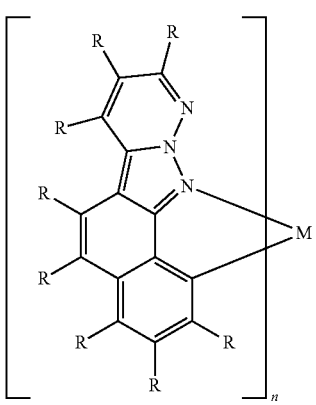
formula (17)
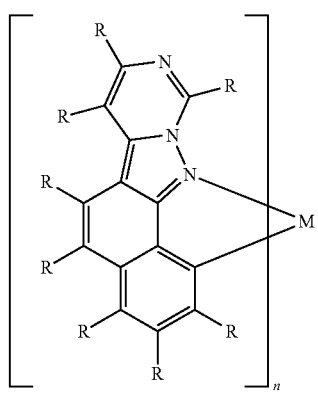
formula (18)
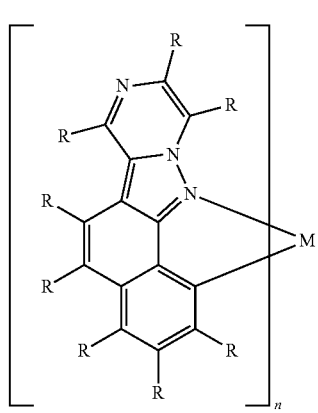
formula (19)
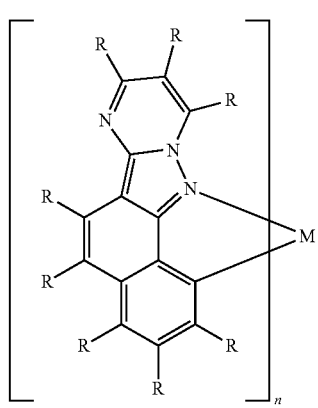
formula (20)
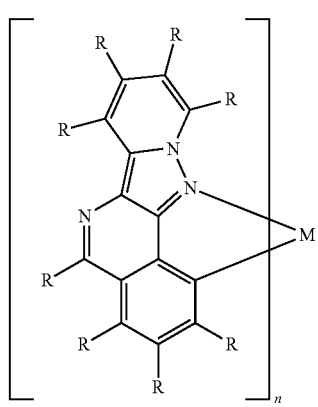

-continued
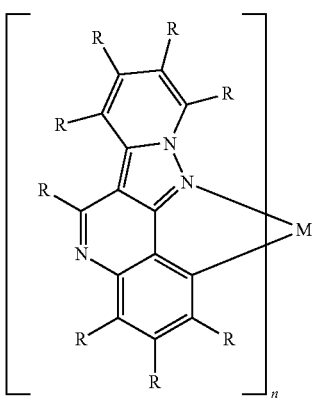
formula (21)
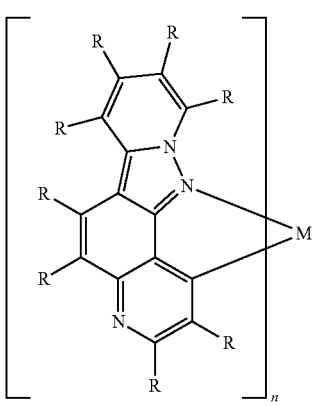
formula (22)
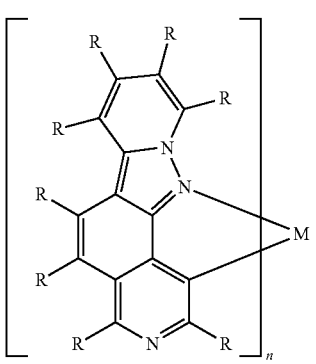
formula (23)
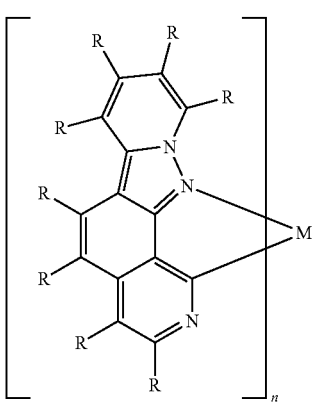
formula (24)
-continued
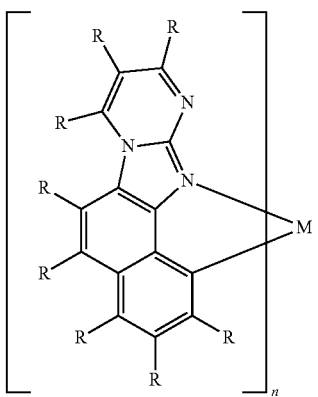
formula (25)
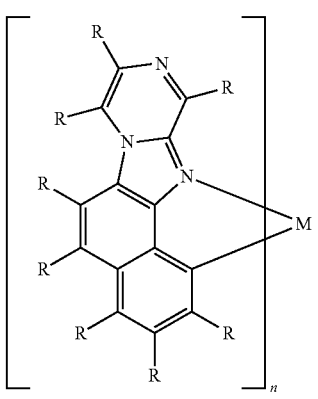
formula (26)
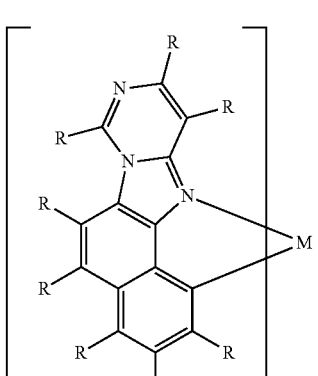
formula (27)
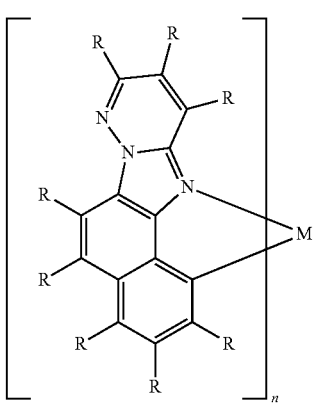
formula (28)

formula (29)

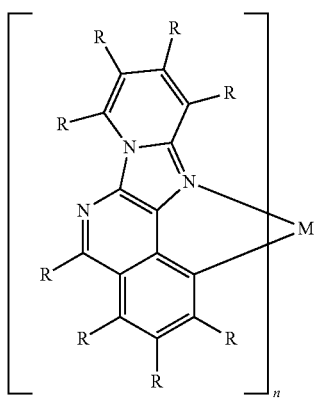

formula (30)

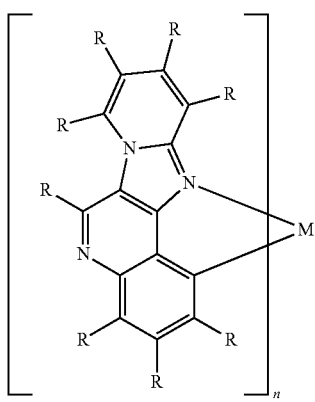

formula (31)

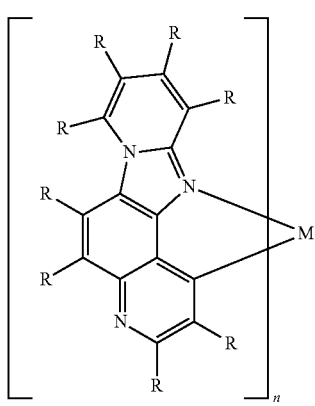

formula (32)

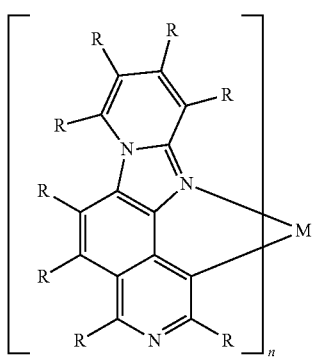

formula (33)

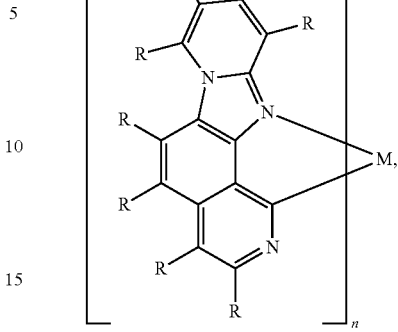

where the symbols and indices used have the meanings given above.

In a preferred embodiment of the invention, for moieties of the formula (2) in which at least one group X=N, at least one group X which is adjacent to this nitrogen atom stands for a $CR^3$ group. This applies analogously to the moieties of the formulae (7) to (33).

$R^3$ here is on each occurrence, identically or differently, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which may be substituted by one or more radicals $R^1$, where one or more non-adjacent $CH_2$ groups may be replaced by $R^1C$=$CR_1$, C≡C, $Si(R^1)_2$, C=O, $NR^1$, O, S or $CONR^1$ and where one or more H atoms may be replaced by D, F, Cl, Br, I or CN, or an aromatic or heteroaromatic ring system having 5 to 60 aromatic ring atoms, which may in each case be substituted by one or more radicals $R^1$, or an aryloxy or heteroaryloxy group having 5 to 40 aromatic ring atoms, which may be substituted by one or more radicals $R^1$, or an aralkyl or heteroaralkyl group having 5 to 40 aromatic ring atoms, which may be substituted by one or more radicals $R^1$, or a diarylamino group, diheteroarylamino group or arylheteroarylamino group having 10 to 40 aromatic ring atoms, which may be substituted by one or more radicals $R^1$; $R^3$ here may also form a mono- or polycyclic, aliphatic, aromatic and/or benzo-fused ring system with an adjacent radical R. $R^3$ is particularly preferably, identically or differently on each occurrence, $CF_3$, $OCF_3$, a branched or cyclic alkyl or alkoxy group having 3 to 20 C atoms, which may in each case be substituted by one or more radicals $R^1$, where one or more non-adjacent $CH_2$ groups which are not bonded directly to the aromatic carbon atom of the ligand may be replaced by $R^1C$=$CR^1$, C≡C, $Si(R^1)_2$, C=O, $NR^1$, O, S or $CONR^1$ and where one or more H atoms may be replaced by D, F, Cl, Br, I or CN, or $Si(R^1)_3$, where $R^1$ is not equal to H or D, a dialkylamino group, where the alkyl groups each have 1 to 10 C atoms and may be linear, branched or cyclic, or an aromatic or heteroaromatic ring system having 5 to 60 aromatic ring atoms, which may in each case be substituted by one or more radicals $R^1$, or an aralkyl or heteroaralkyl group having 5 to 40 aromatic ring atoms, which may be substituted by one or more radicals $R^1$.

In the definition of X, "at least one group X which is adjacent to this nitrogen" means that this X is able to bond directly to the nitrogen or that it is the next-possible position in which an X is present in formula (2). This is explained again with reference to two specific ligands in the following diagrammatic representation:

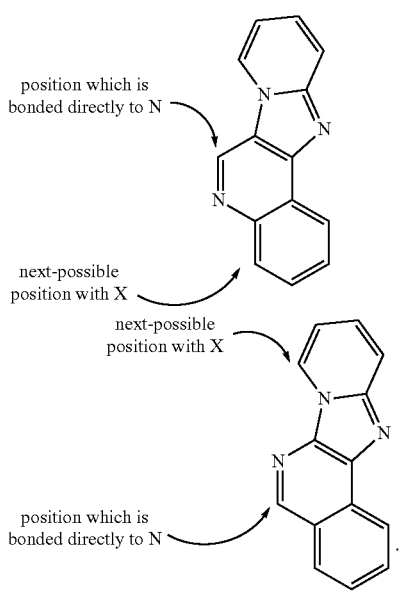

In this representation, both the position which is bonded directly to the nitrogen and the next-possible position in which an X is present is labelled. Both positions are regarded as adjacent positions to the nitrogen for the purposes of the present application.

Preferred embodiments of the structures of the formula (7) to (33) are therefore the structures of the following formulae (7a) to (33a) and (8b) to (32b), formula (7a)
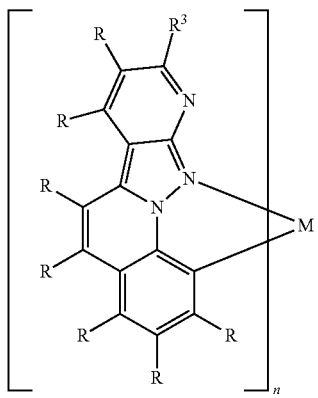

formula (8a)
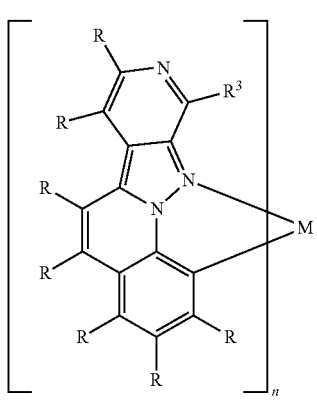

formula (8b)
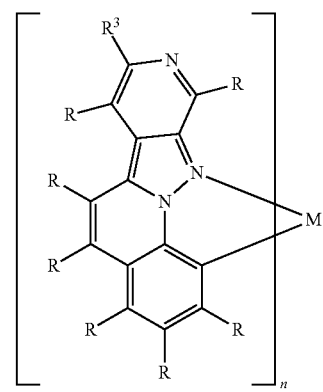

formula (9a)
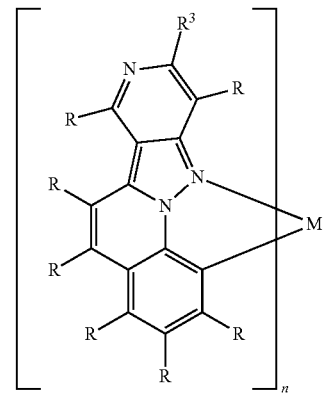

formula (9b)
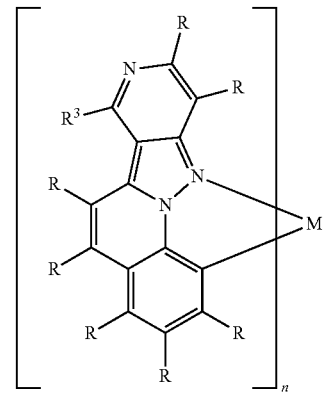

formula (10a)

formula (10b)
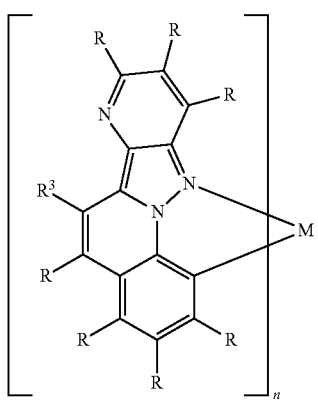
formula (11a)
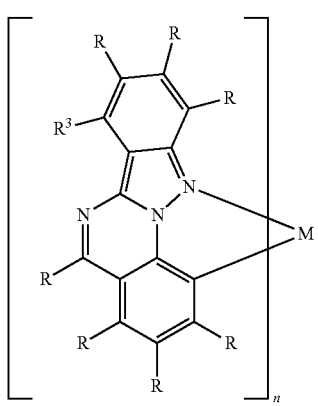
formula (11b)
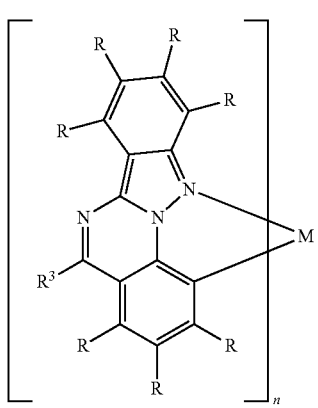
formula (12a)
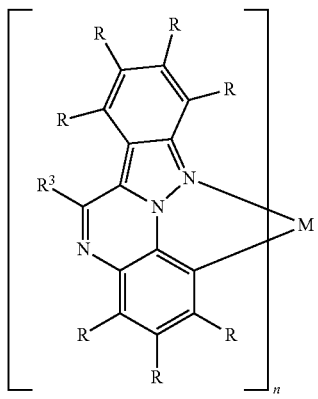
formula (12b)
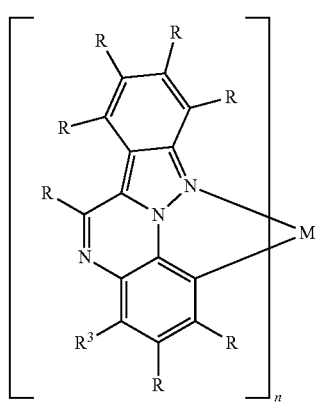
formula (13a)
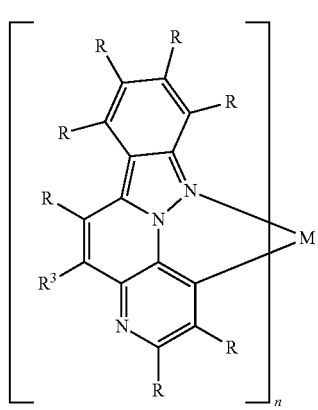
formula (13b)
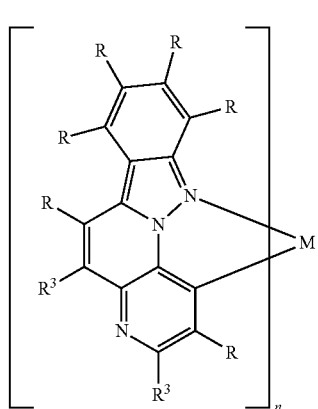
formula (14a)
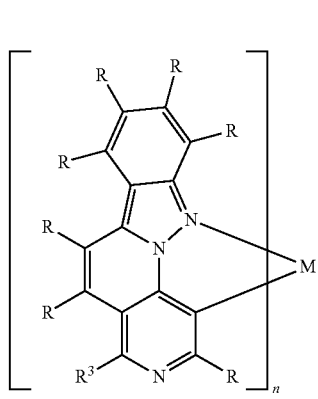

formula (14b)
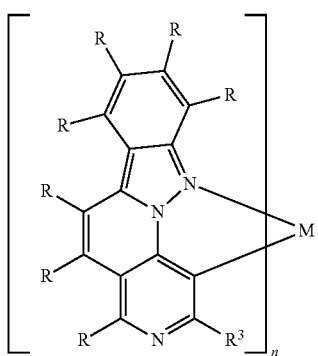
formula (15a)
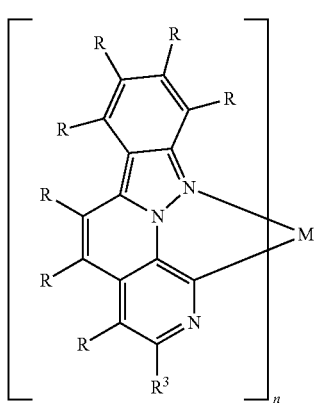
formula (16a)
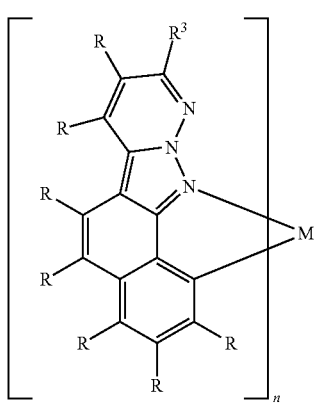
formula (17a)
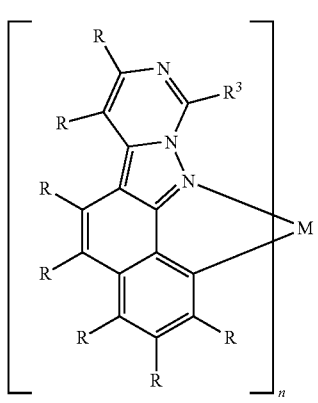
formula (17b)
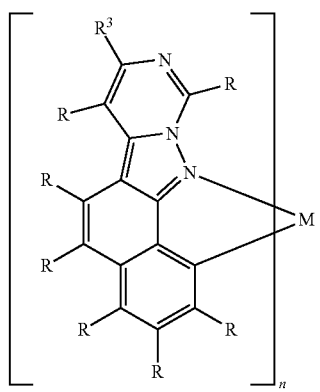
formula (18a)
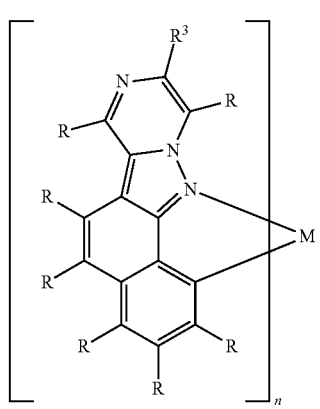
formula (18b)
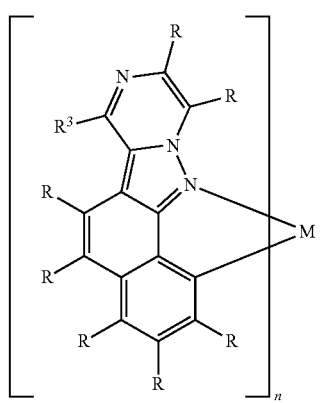
formula (19a)
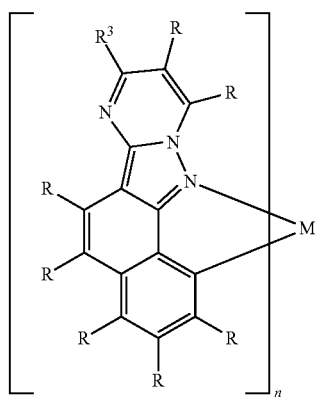

formula (19b)
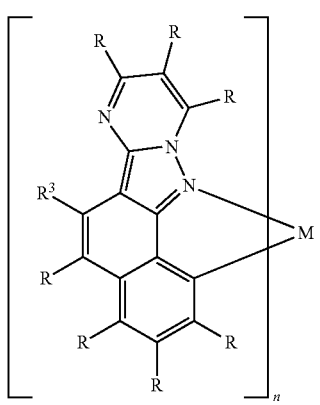
formula (20a)
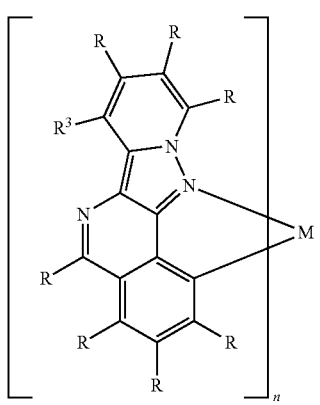
formula (20b)
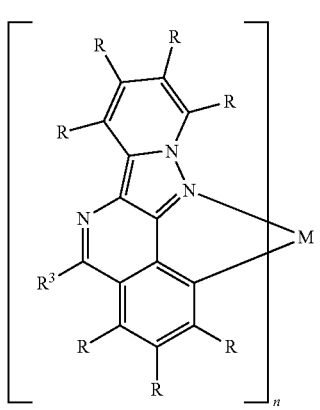
formula (21a)
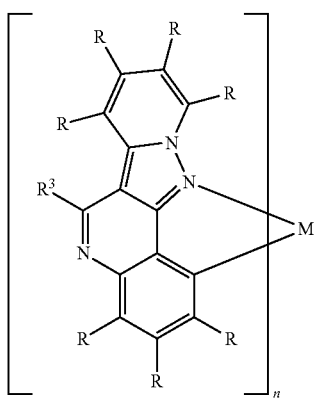
formula (21b)
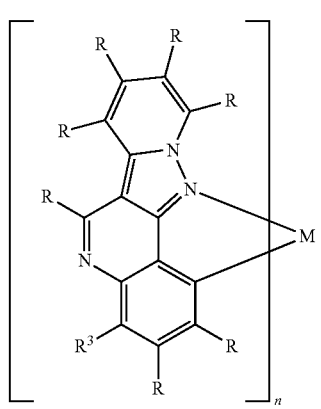
formula (22a)
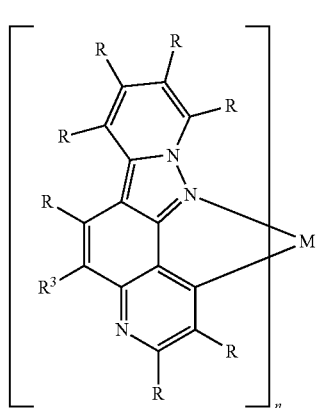
formula (22b)
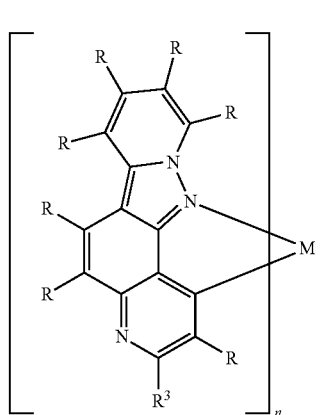
formula (23a)
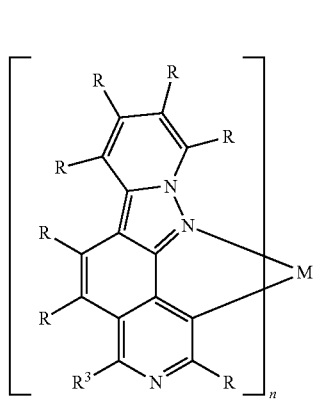

formula (23b)
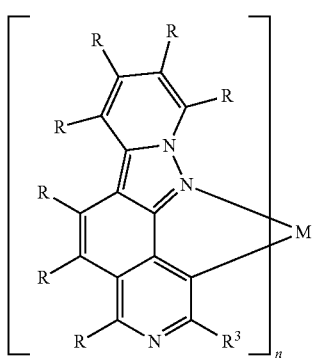
formula (24a)
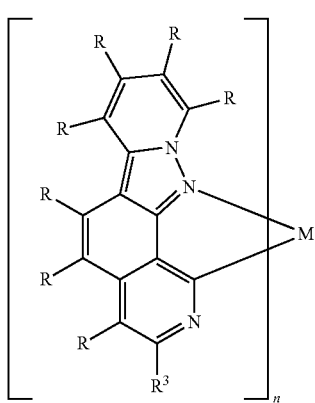
formula (25a)
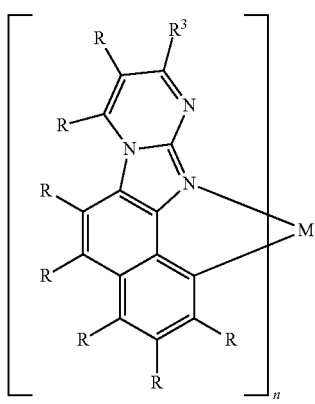
formula (26a)
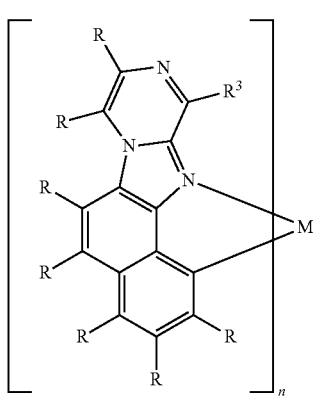
formula (26b)
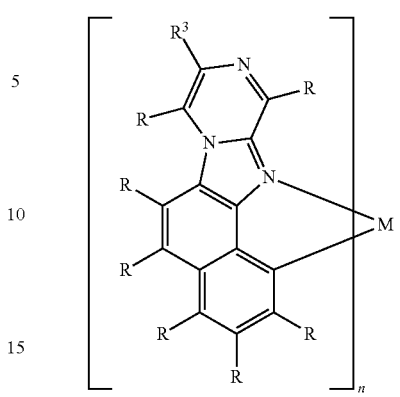
formula (27a)
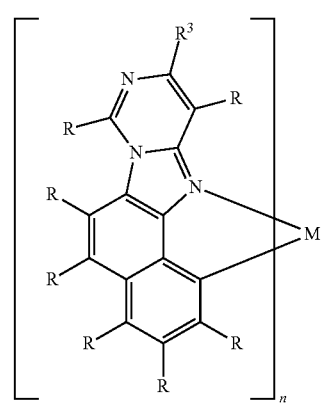
formula (27b)
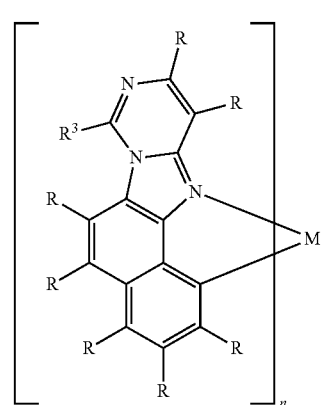
formula (28a)
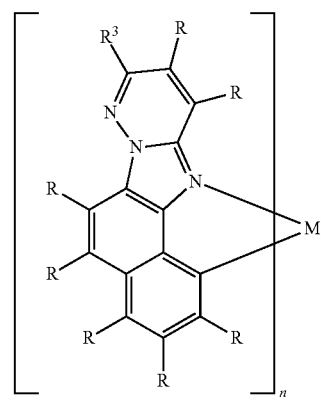

-continued
formula (28b)
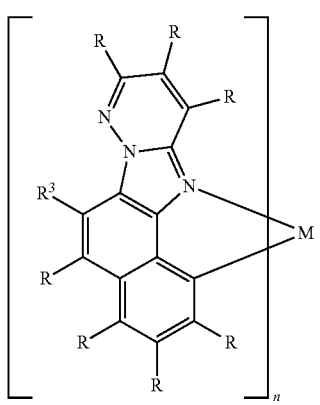
formula (29a)
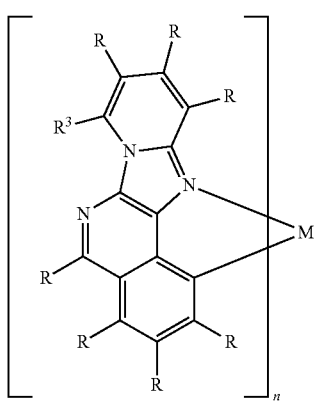
formula (29b)
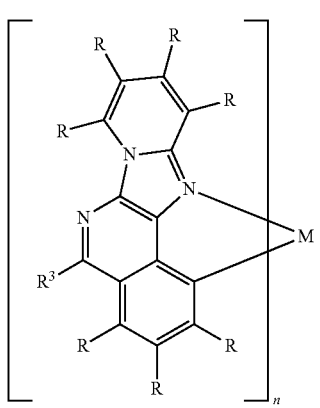
formula (30a)
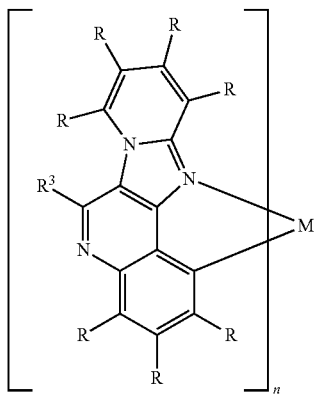
formula (30b)
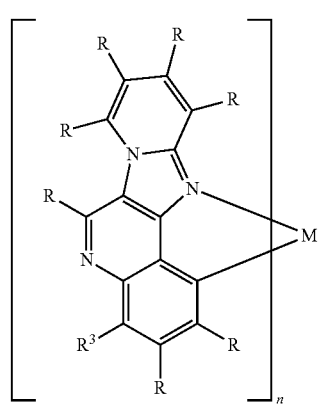
formula (31a)
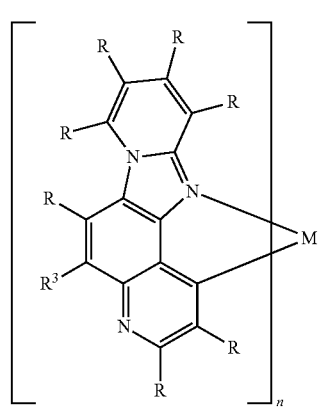
formula (31b)
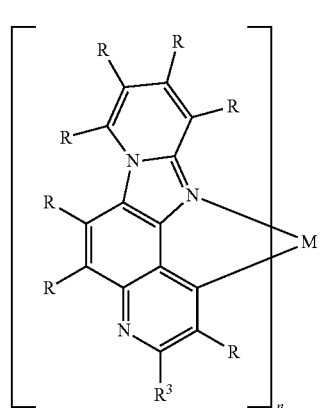
formula (32a)
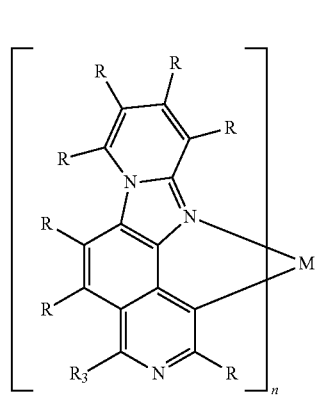

formula (32b)

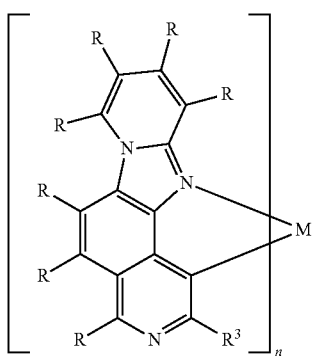

formula (33a)

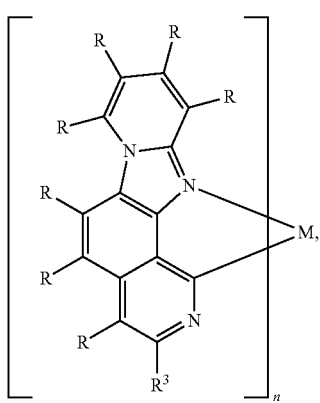

where the symbols and indices used have the meanings given above.

As defined above, $R^3$ is a group selected from alkyl, alkoxy or thioalkoxy groups, silyl groups, aromatic or heteroaromatic ring systems, aralkyl or heteroaralkyl groups or substituted amino groups. These groups are sterically bulky groups.

If $R^3$ stands for an alkyl group, this alkyl group then preferably has 3 to 20, in particular 4 to 10 C atoms. It is furthermore preferably a secondary or tertiary alkyl group in which the secondary or tertiary C atom is either bonded directly to the ligand or is bonded to the ligand via a $CH_2$ group. This alkyl group is particularly preferably selected from the structures of the following formulae $(R^3\text{-}1)$ to $(R^3\text{-}33)$, where in each case the linking of these groups to the ligand is denoted by "Lig":

($R^3$-1)

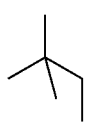

($R^3$-2)

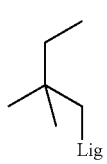

($R^3$-3)

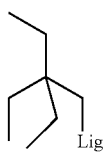

($R^3$-4)

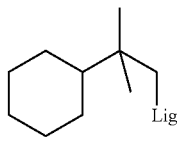

($R^3$-5)

($R^3$-6)

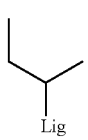

($R^3$-7)

($R^3$-8)

($R^3$-9)

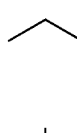

($R^3$-10)

($R^3$-11)

($R^3$-12)

($R^3$-13)

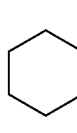

($R^3$-14)

-continued (R³-15) 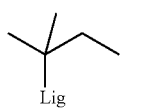

(R³-16) 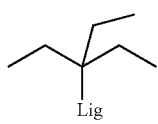

(R³-17) 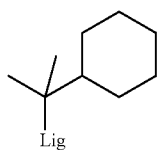

(R³-18) 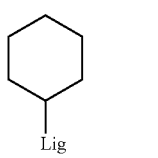

(R³-19) 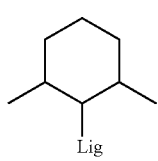

(R³-20) 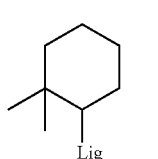

(R³-21) 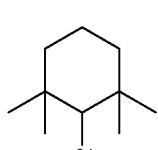

(R³-22) 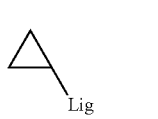

(R³-23) 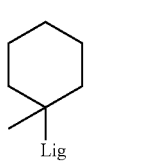

(R³-24) 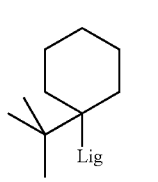

(R³-25) 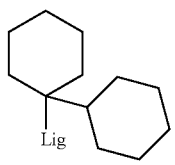

(R³-26) 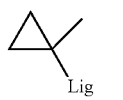

(R³-27) 

(R³-28) 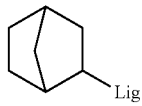

(R³-29) 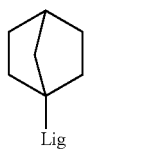

(R³-30) 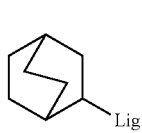

(R³-31) 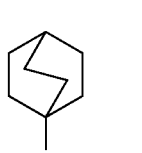

(R³-32) 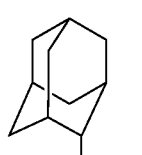

(R³-33) 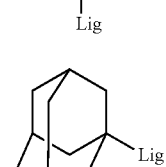

where Lig denotes the linking of the alkyl group to the ligand.

If $R^3$ stands for an alkoxy group, this alkoxy group then preferably has 3 to 20, in particular 4 to 10 C atoms. This alkoxy group is preferably selected from the structures of the following formulae ($R^3$-34) to ($R^3$-47), where in each case the linking of these groups to the ligand is denoted by "Lig":

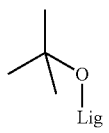 (R³-34)

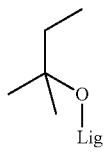 (R³-35)

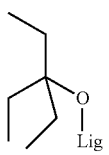 (R³-36)

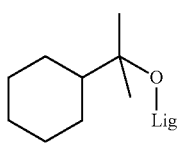 (R³-37)

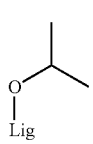 (R³-38)

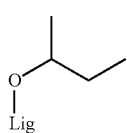 (R³-39)

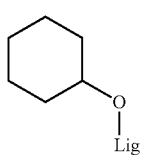 (R³-40)

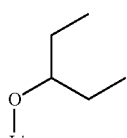 (R³-41)

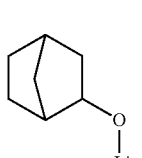 (R³-42)

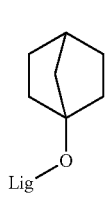 (R³-43)

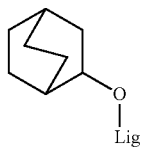 (R³-44)

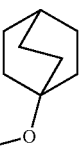 (R³-45)

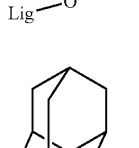 (R³-46)

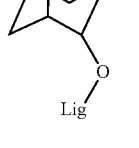 (R³-47)

where Lig denotes the linking of the alkyl group to the ligand.

If $R^3$ stands for a dialkylamino group, each of these alkyl groups then preferably has 1 to 8 C atoms, particularly preferably 1 to 6 C atoms. Examples of suitable alkyl groups are methyl, ethyl or the structures mentioned above as (R³-1) to (R³-33) groups. The dialkylamino group is particularly preferably selected from the structures of the following formulae (R³-48) to (R³-55), where in each case the linking of these groups to the ligand is denoted by "Lig":

 (R³-48)

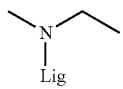 (R³-49)

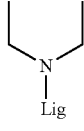 (R³-50)

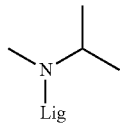 (R³-51)

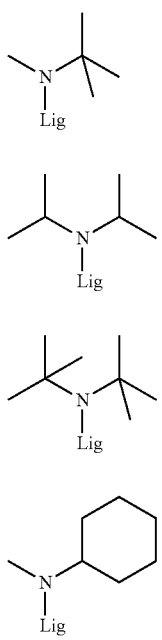
where Lig denotes the linking of the alkyl group to the ligand.
If $R^3$ stands for an aralkyl group, this aralkyl group is then preferably selected from the structures of the following formulae ($R^3$-56) to ($R^3$-69), where in each case the linking of these groups to the ligand is denoted by "Lig":
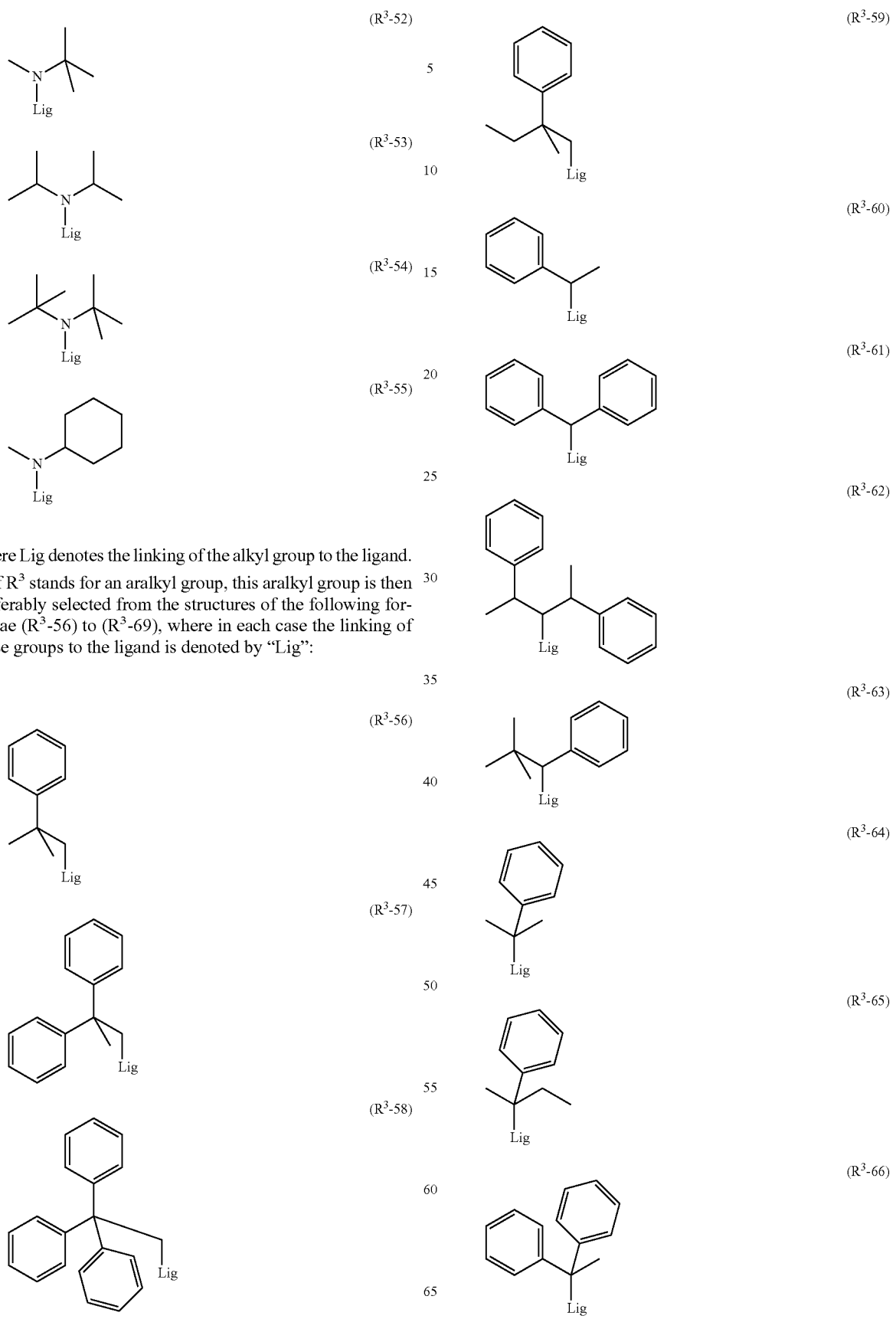

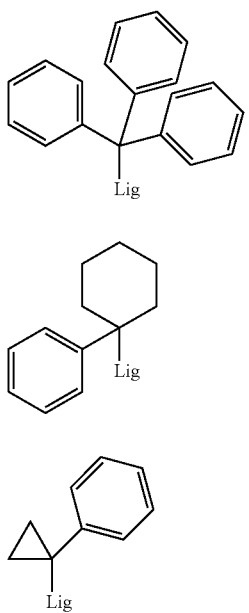

(R³-67)

(R³-68)

(R³-69)

where Lig denotes the linking of the aralkyl group to the ligand and the phenyl groups may each be substituted by one or more radicals R³.

The alkyl, alkoxy, dialkylamino and aralkyl groups may, depending on the precise structure, also have one or more stereocentres. Since the basic structure of the complex may also be a chiral structure, the formation of diastereomers is possible, in particular also if a plurality of such alkyl, alkoxy, dialkylamino and aralkyl groups having stereocentres are present. The complexes according to the invention then encompass both the mixtures of the various diastereomers or the corresponding racemates and also the individual isolated diastereomers or enantiomers.

If R³ stands for an aromatic or heteroaromatic ring system, this aromatic or heteroaromatic ring system then preferably has 5 to 30 aromatic ring atoms, particularly preferably 5 to 24 aromatic ring atoms. If the aromatic ring system contains condensed aryl groups, these are preferably selected from naphthalene, phenanthrene or triphenylene, but no other condensed aryl groups. The aromatic or heteroaromatic ring system preferably preferably contains no aryl or heteroaryl groups in which more than two aromatic six-membered rings are condensed directly onto one another. The aromatic or heteroaromatic ring system particularly preferably contains no condensed aryl or heteroaryl groups at all, and it very particularly preferably contains only phenyl groups. The aromatic ring system here is preferably selected from the structures of the following formulae (R³-70) to (R³-84), where in each case the linking of these groups to the ligand is denoted by "Lig":

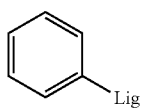

(R³-70)

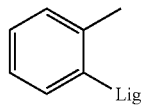

(R³-71)

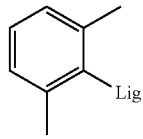

(R³-72)

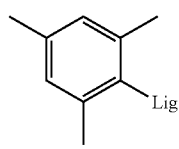

(R³-73)

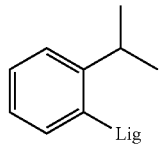

(R³-74)

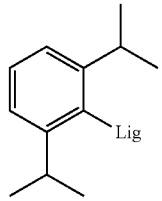

(R³-75)

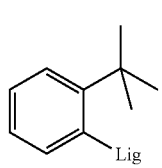

(R³-76)

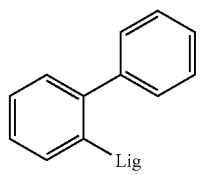

(R³-77)

(R³-78)

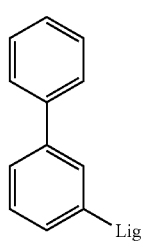

(R³-79)

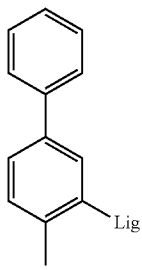 (R³-80)

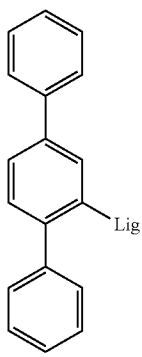 (R³-81)

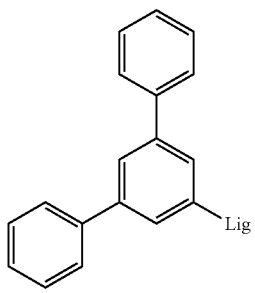 (R³-82)

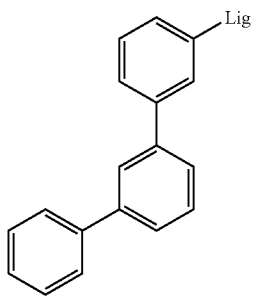 (R³-83)

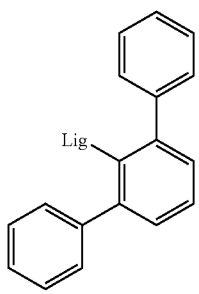 (R³-84)

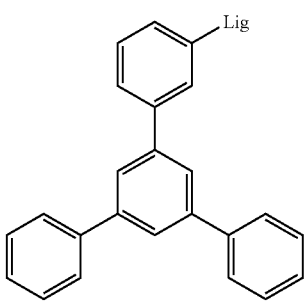 (R³-84a)

where Lig denotes the linking of the aromatic or heteroaromatic ring system to the ligand and the phenyl groups may each be substituted by one or more radicals R¹.

Furthermore, the heteroaromatic ring system is preferably selected from the structures of the following formulae (R³-85) to (R³-115), where in each case the linking of these groups to the ligand is denoted by "Lig":

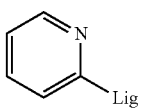 (R³-85)

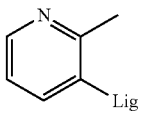 (R³-86)

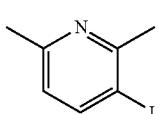 (R³-87)

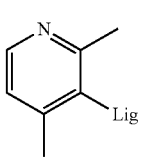 (R³-88)

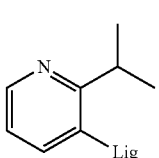 (R³-89)

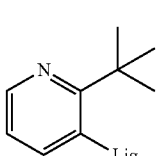 (R³-90)

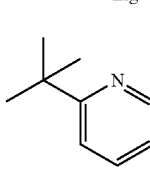 (R³-91)

(R³-92) 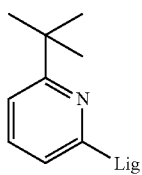
(R³-93) 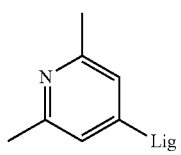
(R³-94) 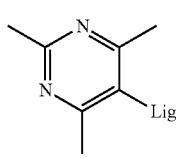
(R³-95) 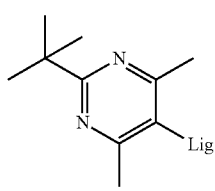
(R³-96) 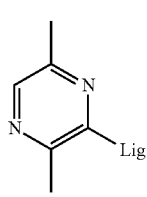
(R³-97) 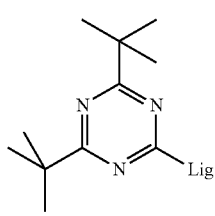
(R³-98) 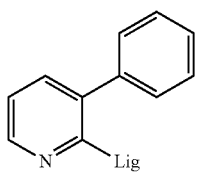
(R³-99) 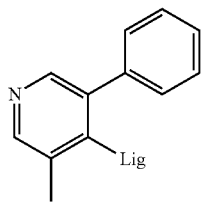
(R³-100) 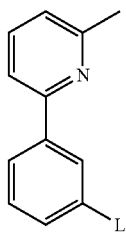
(R³-101) 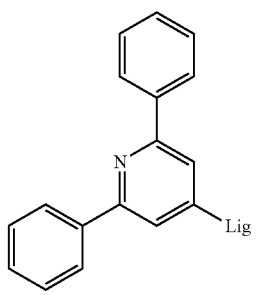
(R³-102) 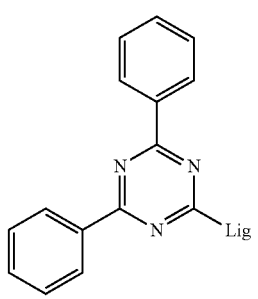
(R³-103) 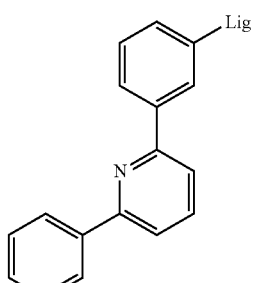
(R³-104) 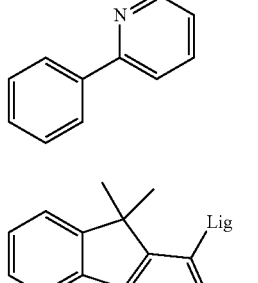
(R³-105) 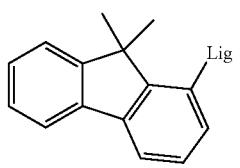
(R³-106) 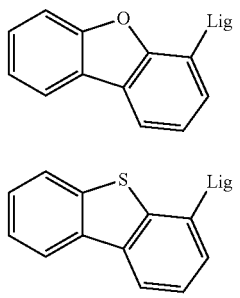

(R³-107) 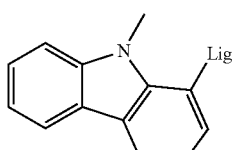

(R³-108) 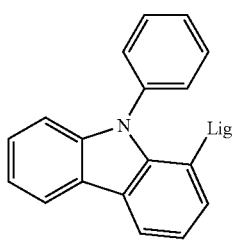

(R³-109) 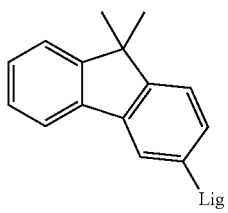

(R³-110) 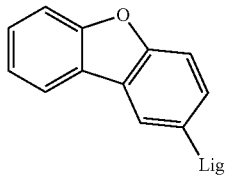

(R³-111) 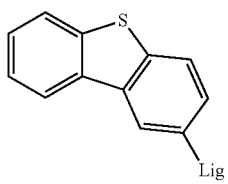

(R³-112) 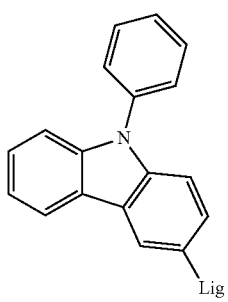

(R³-113) 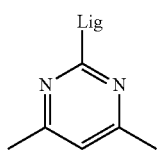

(R³-114) 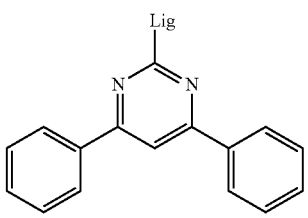

(R³-115) 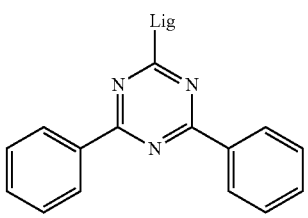

where Lig denotes the linking of the aromatic or heteroaromatic ring system to the ligand and the aromatic and heteroaromatic groups may each be substituted by one or more radicals R¹.

If radicals R which do not stand for R³ are bonded in the moiety of the formula (2), these radicals R are preferably selected on each occurrence, identically or differently, from the group consisting of H, D, F, Br, I, N(R¹)₂, CN, Si(R¹)₃, B(OR¹)₂, C(=O)R¹, a straight-chain alkyl group having 1 to 10 C atoms or an alkenyl group having 2 to 10 C atoms or a branched or cyclic alkyl group having 3 to 10 C atoms, each of which may be substituted by one or more radicals R¹, where one or more H atoms may be replaced by D or F, or an aromatic or heteroaromatic ring system having 5 to 30 aromatic ring atoms, which may in each case be substituted by one or more radicals R¹; two adjacent radicals R here may also form a mono- or polycyclic, aliphatic, aromatic and/or benzo-fused ring system with one another. These radicals R are particularly preferably selected on each occurrence, identically or differently, from the group consisting of H, D, F, N(R¹)₂, a straight-chain alkyl group having 1 to 6 C atoms or a branched or cyclic alkyl group having 3 to 10 C atoms, where one or more H atoms may be replaced by D or F, or an aromatic or heteroaromatic ring system having 5 to 24 aromatic ring atoms, which may in each case be substituted by one or more radicals R¹; two adjacent radicals R here may also form a mono- or polycyclic, aliphatic, aromatic and/or benzo-fused ring system with one another.

In a preferred embodiment of the invention, the radicals R which are bonded to the central six-membered ring do not form an aromatic or benzo-fused ring system with one another, i.e. they either form no ring system at all with one another, or, if they form a ring system with one another, this is an aliphatic ring system. This is explained again with reference to the following diagrammatic representation:

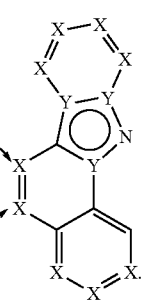

positions of the radicals which are bonded to the central six-membered ring

It is furthermore possible for the substituent R which is in the ortho-position to the metal coordination to represent a group which is likewise coordinated or bonded to the metal M. Preferred coordinating groups R are aryl or heteroaryl groups, for example phenyl or pyridyl, aryl or alkyl cyanides, aryl or alkyl isocyanides, amines or amides, alcohols or alcoholates, thioalcohols or thioalcoholates, phosphines, phosphites, carbonyl functions, carboxylates, carbamides or aryl- or alkylacetylides. The moieties ML of the following formulae (34) to (40), for example, are accessible here:

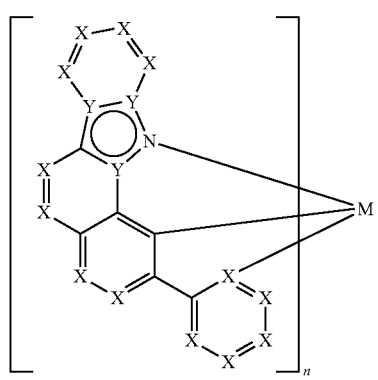

formula (34)

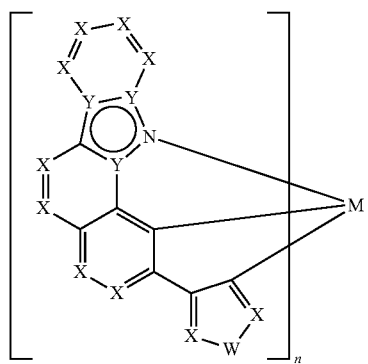

formula (35)

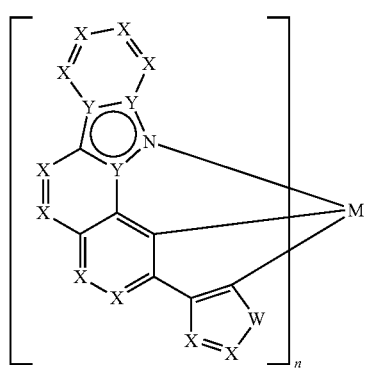

formula (36)

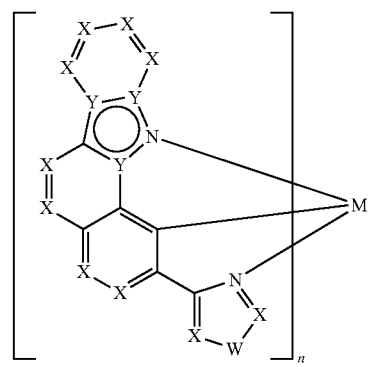

formula (37)

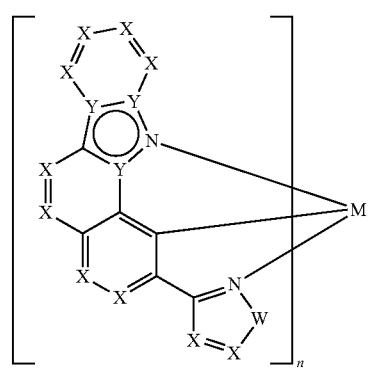

formula (38)

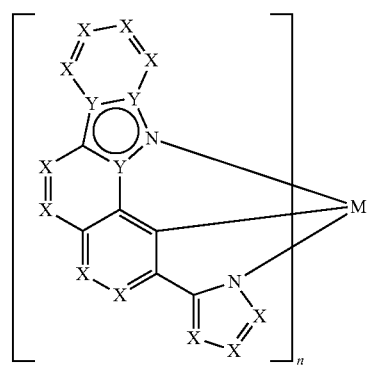

formula (39)

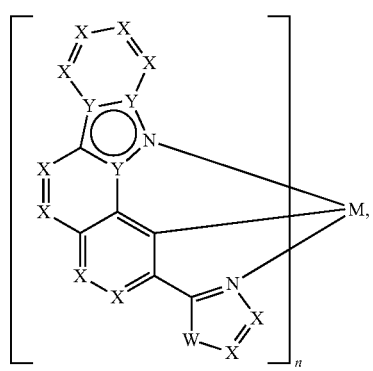

formula (40)

where the symbols and indices used have the same meanings as described above, and W stands, identically or differently on each occurrence, for S, O or $NR^1$.

The formulae (34) to (40) show, merely by way of example, how the substituent R can additionally coordinate to the metal. Other groups R which coordinate to the metal, for example also carbenes, are also accessible entirely analogously without further inventive step.

As described above, a single bond or a bridging unit V which links this ligand L to one or more further ligands L or L' may also be present instead of one of the radicals R. In a preferred embodiment of the invention, a single bond or a bridging unit V is present instead of one of the radicals R, in particular instead of the radicals R which are in the ortho- or meta-position to the coordinating atom, so that the ligands have a tridentate or polydentate or polypodal character. It is also possible for two such bridging units V to be present. This results in the formation of macrocyclic ligands or in the formation of cryptates.

Preferred structures containing polydentate ligands are the metal complexes of the following formulae (41) to (46),

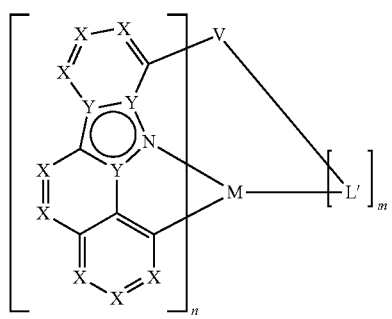

formula (41)

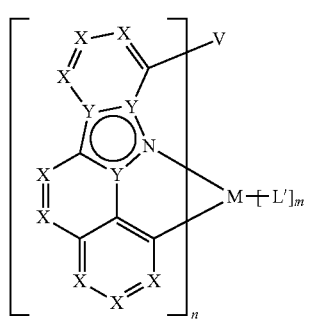

formula (42)

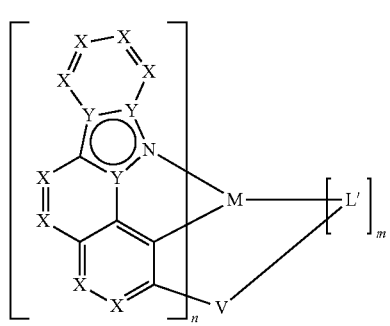

formula (43)

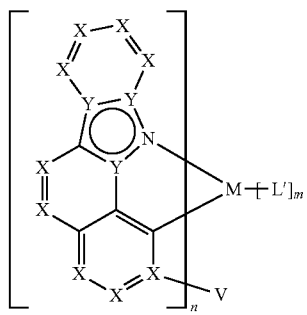

formula (44)

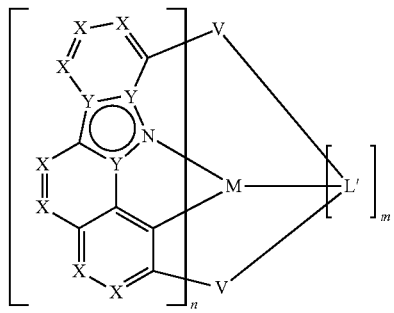

formula (45)

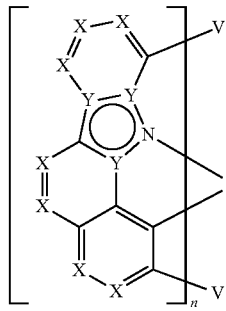

formula (46)

where the symbols used have the meanings given above, where V preferably represents a single bond or a bridging unit containing 1 to 80 atoms from the third, fourth, fifth and/or sixth main group (IUPAC group 13, 14, 15 or 16), preferably 1 to 20 atoms from the third, fourth, fifth and/or sixth main group, or a 3- to 6-membered homo- or heterocycle which covalently bonds the part-ligands L to one another or L to L' to one another. The bridging unit V here may also have an asymmetrical structure, i.e. the linking of V to L and L' need not be identical, and V may also be substituted by one or more radicals $R^1$. The bridging unit V can be neutral, singly, doubly or triply negatively charged or singly, doubly or triply positively charged. V is preferably neutral or singly negatively charged or singly positively charged, particularly preferably neutral. The charge of V is preferably selected so that overall a neutral complex forms. The preferences given above for the moiety $ML_n$ apply to the ligands and n is preferably at least 2.

The precise structure and chemical composition of the group V has no significant influence on the electronic properties of the complex, since the job of this group is essentially to increase the chemical and thermal stability of the complexes by the bridging of L with one another or with L'.

If V is a trivalent group, i.e. bridges three ligands L to one another or two ligands L to L' or one ligand L to two ligands L', V is preferably selected, identically or differently on each occurrence, from the group consisting of B, $B(R^1)^-$, $B(C(R^1)_2)_3$, $(R^1)B(C(R^1)_2)_3^-$, $B(O)_3$, $(R^1)B(O)_3^-$, $B(C(R^1)_2C$ $(R^1)_2)_3$, $(R^1)B(C(R^1)_2C(R^1)_2)_3^-$, $B(C(R^1)_2O)_3$, $(R^1)B(C(R^1)_2O)_3^-$, $B(OC(R^1)_2)_3$, $(R^1)B(OC(R^1)_2)_3^-$, $C(R^1)$, $CO^-$, $CN(R^1)_2$, $(R^1)C(C(R^1)_2)_3$, $(R^1)C(O)_3$, $(R^1)C(C(R^1)_2C(R^1)_2)_3$, $(R^1)C(C(R^1)_2O)_3$, $(R^1)C(OC(R^1)_2)_3$, $(R^1)C(Si(R^1)_2)_3$, $(R^1)C(Si(R^1)_2C(R^1)_2)_3$, $(R^1)C(C(R^1)_2Si(R^1)_2)_3$, $(R^1)C(Si(R^1)_2Si(R^1)_2)_3$, $Si(R^1)$, $(R^1)Si(C(R^1)_2)_3$, $(R^1)Si(O)_3$, $(R^1)Si(C(R^1)_2C(R^1)_2)_3$, $(R^1)Si(OC(R^1)_2)_3$, $(R^1)Si(C(R^1)_2O)_3$, $(R^1)Si(Si(R^1)_2)_3$, $(R^1)Si(Si(R^1)_2C(R^1)_2)_3$, $(R^1)Si(C(R^1)_2Si(R^1)_2)_3$, $(R^1)Si(Si(R^1)_2Si(R^1)_2)_3$, $N$, $NO$, $N(R^1)^+$, $N(C(R^1)_2)_3$, $(R^1)N(C(R^1)_2)_3^+$, $N(C=O)_3$, $N(C(R^1)_2C(R^1)_2)_3$, $(R^1)N(C(R^1)_2C(R^1)_2)^+$, $P$, $P(R^1)^+$, $PO$, $PS$, $PSe$, $PTe$, $P(O)_3$, $PO(O)_3$, $P(OC(R^1)_2)_3$, $PO(OC(R^1)_2)_3$, $P(C(R^1)_2)_3$, $P(R^1)(C(R^1)_2)_3^+$, $PO(C(R^1)_2)_3$, $P(C(R^1)_2C(R^1)_2)_3$, $P(R^1)(C(R^1)_2C(R^1)_2)_3^+$, $PO(C(R^1)_2C(R^1)_2)_3$, $S^+$, $S(C(R^1)_2)_3^+$, $S(C(R^1)_2C(R^1)_2)_3^+$, or a unit of the formula (47), (48), (49) or (50),

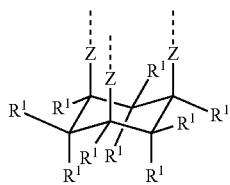

formula (47)

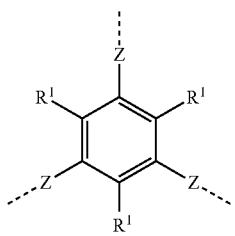

formula (48)

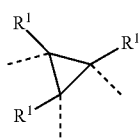

formula (49)

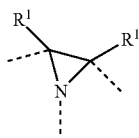

formula (50)

where the dashed bonds in each case indicate the bond to the part-ligands L or L', and Z is selected, identically or differently on each occurrence, from the group consisting of a single bond, O, S, S(=O), S(=O)$_2$, NR$^1$, PR$^1$, P(=O)R$^1$, P(=NR$^1$), C(R$^1$)$_2$, C(=O), C(=NR$^1$), C(=C(R$^1$)$_2$), Si(R$^1$)$_2$ or BR$^1$. The other symbols used have the meanings given above.

If V is a divalent group, i.e. bridges two ligands L to one another or one ligand L to L', V is preferably selected, identically or differently on each occurrence, from the group consisting of BR$^1$, B(R$^1$)$_2^-$, C(R$^1$)$_2$, C(=O), Si(R$^1$)$_2$, NR$^1$, PR$^1$, P(R$^1$)$_2^+$, P(=O)(R$^1$), P(=S)(R$^1$), AsR$^1$, As(=O)(R$^1$), As(=S)(R$^1$), O, S, Se, or a unit of the formulae (51) to (60),

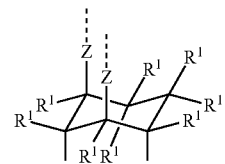

formula (51)

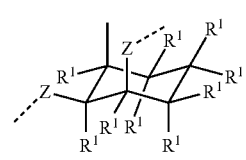

formula (52)

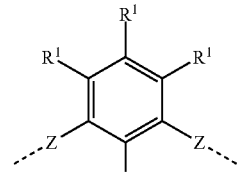

formula (53)

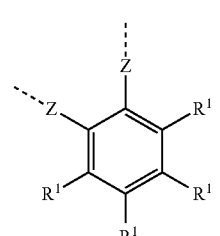

formula (54)

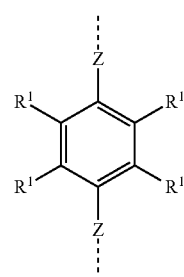

formula (55)

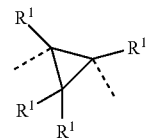

formula (56)

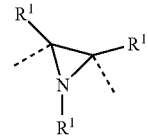

formula (57)

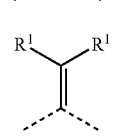

formula (58)

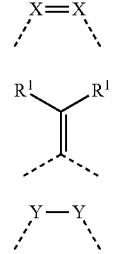

formula (59)

formula (60)

where the dashed bonds in each case indicate the bond to the part-ligands L or L', Y stands on each occurrence, identically or differently, for $C(R^1)_2$, $N(R^1)$, O or S, and the other symbols used each have the meanings indicated above.

Preferred ligands L' as occur in formula (1) are described below. The ligand groups L' can also be selected correspondingly if they are bonded to L via a bridging unit V, as indicated in formulae (41), (43) and (45).

The ligands L' are preferably neutral, monoanionic, dianionic or trianionic ligands, particularly preferably neutral or monoanionic ligands. They can be monodentate, bidentate, tridentate or tetradentate and are preferably bidentate, i.e. preferably have two coordination sites. As described above, the ligands L' can also be bonded to L via a bridging group V.

Preferred neutral, monodentate ligands L' are selected from the group consisting of carbon monoxide, nitrogen monoxide, alkyl cyanides, such as, for example, acetonitrile, aryl cyanides, such as, for example, benzonitrile, alkyl isocyanides, such as, for example, methyl isonitrile, aryl isocyanides, such as, for example, benzoisonitrile, amines, such as, for example, trimethylamine, triethylamine, morpholine, phosphines, in particular halophosphines, trialkylphosphines, triarylphosphines or alkylarylphosphines, such as, for example, trifluorophosphine, trimethylphosphine, tricyclohexylphosphine, tri-tert-butylphosphine, triphenylphosphine, tris(pentafluorophenyl)phosphine, dimethylphenylphosphine, methyldiphenylphosphine, bis(tert-butyl)phenylphosphine, phosphites, such as, for example, trimethyl phosphite, triethyl phosphite, arsines, such as, for example, trifluoroarsine, trimethylarsine, tricyclohexylarsine, tri-tert-butylarsine, triphenylarsine, tris(pentafluorophenyl)arsine, stibines, such as, for example, trifluorostibine, trimethylstibine, tricyclohexylstibine, tri-tert-butylstibine, triphenylstibine, tris(pentafluorophenyl)stibine, nitrogen-containing heterocycles, such as, for example, pyridine, pyridazine, pyrazine, pyrimidine, triazine, and carbenes, in particular Arduengo carbenes.

Preferred monoanionic, monodentate ligands L' are selected from hydride, deuteride, the halides $F^-$, $Cl^-$, $Br^-$ and $I^-$, alkylacetylides, such as, for example, methyl-C≡$C^-$, tert-butyl-C≡$C^-$, arylacetylides, such as, for example, phenyl-C≡$C^-$, cyanide, cyanate, isocyanate, thiocyanate, isothiocyanate, aliphatic or aromatic alcoholates, such as, for example, methanolate, ethanolate, propanolate, iso-propanolate, tert-butylate, phenolate, aliphatic or aromatic thioalcoholates, such as, for example, methanethiolate, ethanethiolate, propanethiolate, iso-propanethiolate, tert-thiobutylate, thiophenolate, amides, such as, for example, dimethylamide, diethylamide, di-iso-propylamide, morpholide, carboxylates, such as, for example, acetate, trifluoroacetate, propionate, benzoate, aryl groups, such as, for example, phenyl, naphthyl, and anionic, nitrogen-containing heterocycles, such as pyrrolide, imidazolide, pyrazolide. The alkyl groups in these groups are preferably $C_1$-$C_{20}$-alkyl groups, particularly preferably $C_1$-$C_{10}$-alkyl groups, very particularly preferably $C_1$-$C_4$-alkyl groups. An aryl group is also taken to mean heteroaryl groups. These groups are as defined above.

Preferred di- or trianionic ligands are $O^{2-}$, $S^{2-}$, carbides, which result in coordination in the form R—C≡M, and nitrenes, which result in coordination in the form R—N=M, where R generally stands for a substituent, or $N^{3-}$.

Preferred neutral or mono- or dianionic, bidentate or polydentate ligands L' are selected from diamines, such as, for example, ethylenediamine, N,N,N',N'-tetramethylethylenediamine, propylenediamine, N,N,N',N'-tetramethylpropylenediamine, cis- or trans-diaminocyclohexane, cis- or trans-N,N,N',N'-tetramethyldiaminocyclohexane, imines, such as, for example, 2-[1-(phenylimino)ethyl]pyridine, 2-[1-(2-methylphenylimino)ethyl]pyridine, 2-[1-(2,6-di-iso-propylphenylimino)ethyl]pyridine, 2-[1-(methylimino)ethyl]-pyridine, 2-[1-(ethylimino)ethyl]pyridine, 2-[1-(iso-propylimino)ethyl]pyridine, 2-[1-(tert-butylimino)ethyl]pyridine, diimines, such as, for example, 1,2-bis(methylimino)ethane, 1,2-bis(ethylimino)ethane, 1,2-bis(iso-propylimino)ethane, 1,2-bis(tert-butylimino)ethane, 2,3-bis(methylimino)butane, 2,3-bis(ethylimino)butane, 2,3-bis(iso-propylimino)butane, 2,3-bis(tertbutylimino)butane, 1,2-bis(phenylimino)ethane, 1,2-bis(2-methylphenylimino)ethane, 1,2-bis(2,6-di-iso-propylphenylimino)ethane, 1,2-bis(2,6-di-tert-butylphenylimino)ethane, 2,3-bis(phenylimino)butane, 2,3-bis(2-methylphenylimino)butane, 2,3-bis(2,6-di-iso-propylphenylimino)butane, 2,3-bis(2,6-di-tert-butylphenylimino)butane, heterocycles containing two nitrogen atoms, such as, for example, 2,2'-bipyridine, o-phenanthroline, diphosphines, such as, for example, bis(diphenylphosphino)methane, bis(diphenylphosphino)ethane, bis(diphenylphosphino)propane, bis(diphenylphosphino)butane, bis(dimethylphosphino)methane, bis(dimethylphosphino)ethane, bis(dimethylphosphino)propane, bis(diethylphosphino)methane, bis(diethylphosphino)ethane, bis(diethylphosphino)propane, bis(di-tert-butylphosphino)methane, bis(di-tert-butylphosphino)ethane, bis(tert-butylphosphino)propane, 1,3-diketonates derived from 1,3-diketones, such as, for example, acetylacetone, benzoylacetone, 1,5-diphenylacetylacetone, dibenzoylmethane, bis(1,1,1-trifluoroacetyl)methane, 2,2,6,6-tetramethyl-3,5-heptanedione, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylaminoalanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol, and dithiolates derived from dithiols, such as, for example, 1,2-ethylenedithiol, 1,3-propylenedithiol.

Preferred tridentate ligands are borates of nitrogen-containing heterocycles, such as, for example, tetrakis(1-imidazolyl) borate and tetrakis(1-pyrazolyl) borate.

Preference is furthermore given to bidentate monoanionic, neutral or dianionic ligands L', in particular monoanionic ligands, which, with the metal, form a cyclometallated five- or six-membered ring with at least one metal-carbon bond, in particular a cyclometallated five-membered ring. These are, in particular, ligands as are generally used in the area of phosphorescent metal complexes for organic electroluminescent devices, i.e. ligands of the type phenylpyridine, naphthylpyridine, phenylquinoline, phenylisoquinoline, etc., each of which may be substituted by one or more radicals R. A multiplicity of ligands of this type is known to the person skilled in the art in the area of phosphorescent electroluminescent devices, and he will be able, without inventive step, to select further ligands of this type as ligand L' for compounds of the formula (1). The combination of two groups as depicted by the following formulae (61) to (88) is generally particularly suitable for this purpose, where one group is preferably bonded via a neutral nitrogen atom or a carbene carbon atom and the other group is preferably bonded via a negatively charged carbon atom or a negatively charged nitrogen atom. The ligand L' can then be formed from the groups of the formulae (61) to (88) through these groups bonding to one another in each case at the position denoted by #. The position at which the groups coordinate to the metal is denoted by *. These groups may also be bonded to the ligand L via one or two bridging units V.
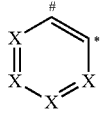
formula (61)
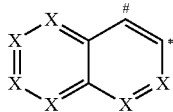
formula (62)
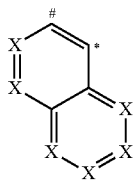
formula (63)
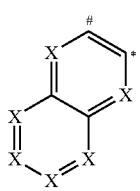
formula (64)
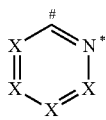
formula (65)
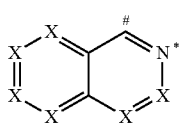
formula (66)
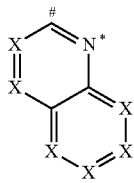
formula (67)
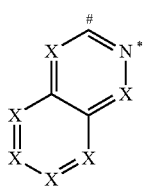
formula (68)
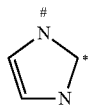
formula (69)
-continued
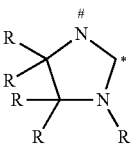
formula (70)
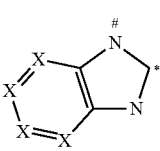
formula (71)
formula (72)
formula (73)
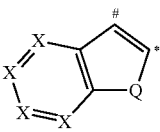
formula (74)
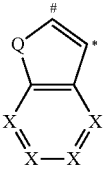
formula (75)
formula (76)
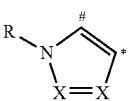
formula (77)
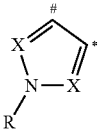
formula (78)
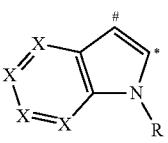
formula (79)

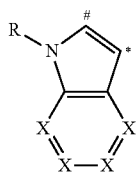
formula (80)

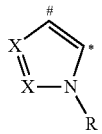
formula (81)

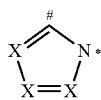
formula (82)

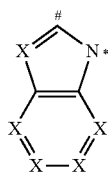
formula (83)

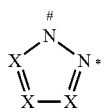
formula (84)

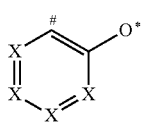
formula (85)

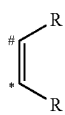
formula (86)

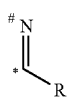
formula (87)

formula (88)

Q here stands, identically or differently on each occurrence, for O or S, and X and R have the same meanings as described above. Preferably, a maximum of three symbols X in each group stand for N, particularly preferably a maximum of two symbols X in each group stand for N, very particularly preferably a maximum of one symbol X in each group stands for N. Especially preferably, all symbols X stand for CR.

Likewise preferred ligands L' are $\eta^5$-cyclopentadienyl, $\eta^5$-pentamethylcyclopentadienyl, $\eta^6$-benzene or $\eta^7$-cycloheptatrienyl, each of which may be substituted by one or more radicals R.

Likewise preferred ligands L' are 1,3,5-cis,cis-cyclohexane derivatives, in particular of the formula (89), 1,1,1-tri(methylene)methane derivatives, in particular of the formula (90), and 1,1,1-trisubstituted methanes, in particular of the formulae (91) and (92):

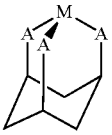
formula (89)

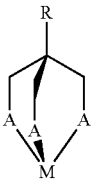
formula (90)

formula (91)

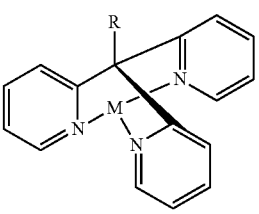
formula (92)

where the coordination to the metal M is shown in each of the formulae, R has the meaning given above, and A stands, identically or differently on each occurrence, for $O^-$, $S^-$, $COO^-$, $PR_2$ or $NR_2$.

The complexes according to the invention can be facial or pseudofacial or they can be meridional or pseudomeridional.

The preferred embodiments indicated above can be combined with one another as desired. In a particularly preferred embodiment of the invention, the preferred embodiments indicated above apply simultaneously.

The metal complexes according to the invention can in principle be prepared by various processes. However, the processes described below have proven particularly suitable.

The present invention therefore furthermore relates to a process for the preparation of the metal complex compounds of the formula (1) by reaction of the corresponding free ligands with metal alkoxides of the formula (93), with metal ketoketonates of the formula (94), with metal halides of the formula (95) or with dimeric metal complexes of the formula (96):

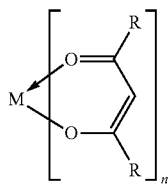 formula (93)

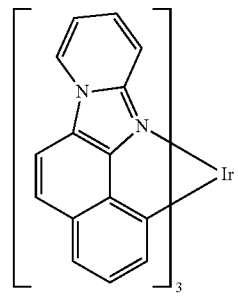 formula (94)

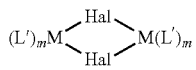 formula (95)

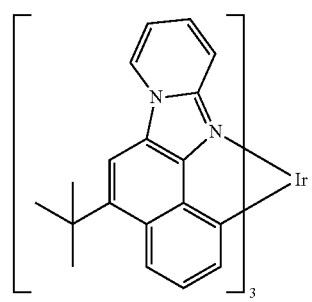 formula (96)

where the symbols M, L', m, n and R have the meanings indicated above, and Hal =F, Cl, Br or I.

It is likewise possible to use metal compounds, in particular iridium compounds, which carry both alkoxide and/or halide and/or hydroxyl radicals as well as ketoketonate radicals. These compounds may also be charged. Corresponding iridium compounds which are particularly suitable as starting materials are disclosed in WO 2004/085449. Particularly suitable are [IrCl$_2$(acac)$_2$T, for example Na[IrCl$_2$(acac)$_2$],], metal complexes with acetylacetonate Derivatives as ligand, for example Ir(acac)$_3$ or tris(2,2,6,6-tetramethylheptane-3,5-dionato)iridium, and IrCl$_3$.xH$_2$O, where x usually stands for a number between 2 and 4.

Suitable platinum starting materials are, for example, PtCl$_2$, K$_2$[PtCl$_4$], PtCl$_2$(DMSO)$_2$, Pt(Me)$_2$(DMSO)$_2$ or PtCl$_2$(benzonitrile)$_2$.

The synthesis of the complexes is preferably carried out as described in WO 2002/060910, WO 2004/085449, WO 2007/065523 and WO 2010/086089. Heteroleptic complexes can also be synthesised, for example, in accordance with WO 2005/042548. The synthesis here can also be activated, for example, thermally, photochemically and/or by microwave radiation. In a preferred embodiment of the invention, the reaction is carried out in the melt without the use of an additional solvent. "Melt" here means that the ligand is in molten form and the metal precursor is dissolved or suspended in this melt.

These processes enable the compounds of the formula (1) according to the invention to be obtained in high purity, preferably greater than 99% (determined by means of $^1$H-NMR and/or HPLC).

The compounds according to the invention can also be rendered soluble through suitable substitution, for example by relatively long alkyl groups (about 4 to 20 C atoms), in particular branched alkyl groups, or optionally substituted aryl groups, for example xylyl, mesityl or oligoaryl groups, for example linear or branched terphenyl or quaterphenyl groups. Such compounds are then soluble in common organic solvents, such as, for example, toluene or xylene, at room temperature in sufficient concentration in order to be able to process the complexes from solution. These soluble compounds are particularly highly suitable for processing from solution, for example by printing processes.

Examples of compounds according to the invention are structures 1 to 66 depicted below.

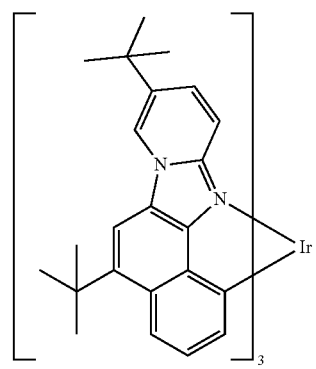

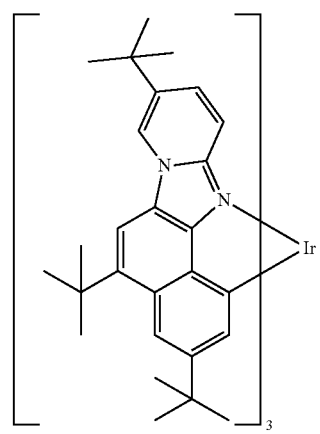

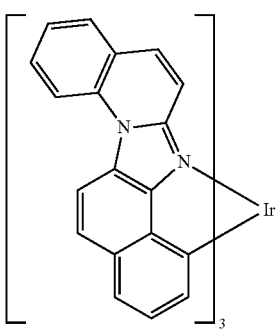
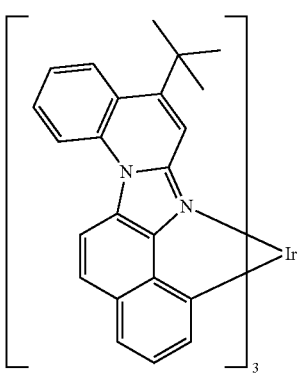
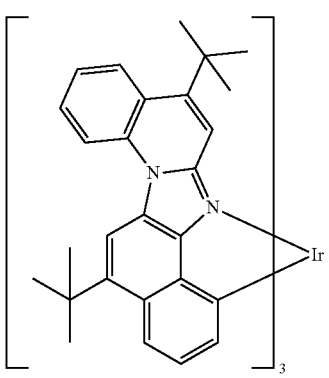
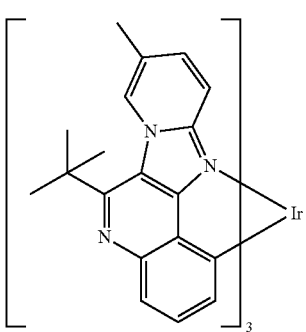
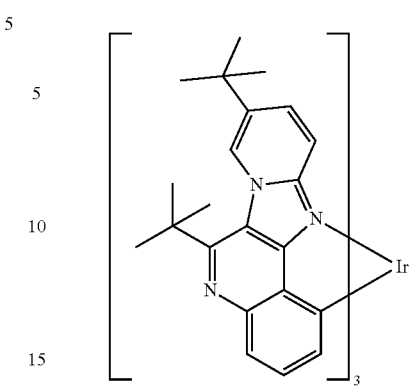
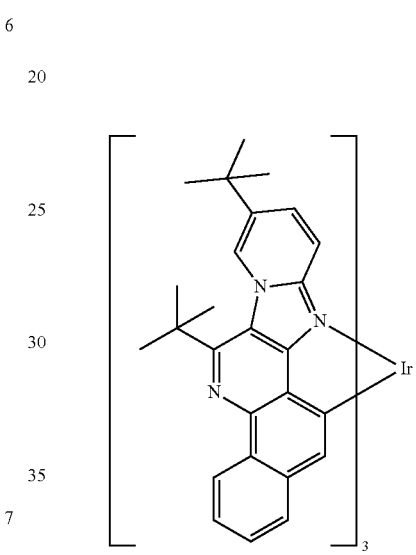
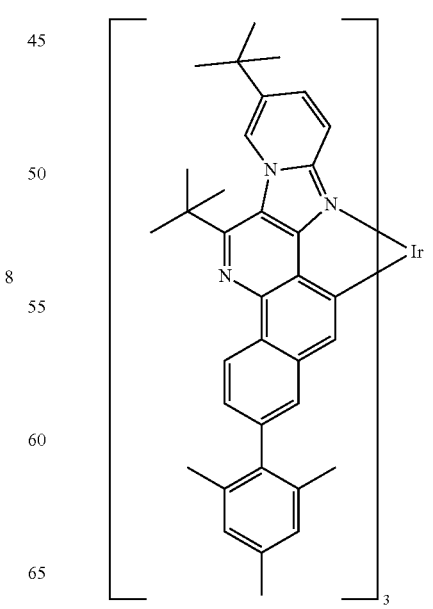

12
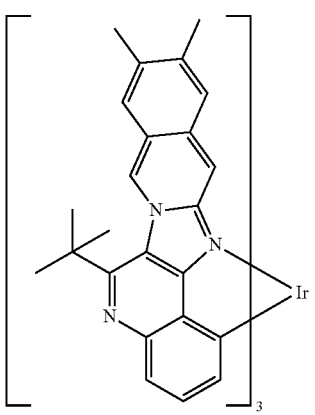
13
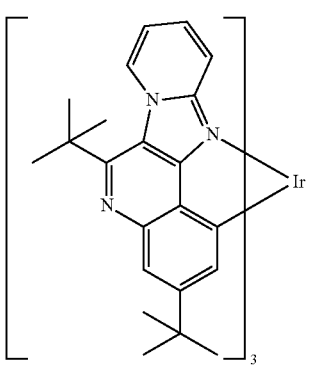
14
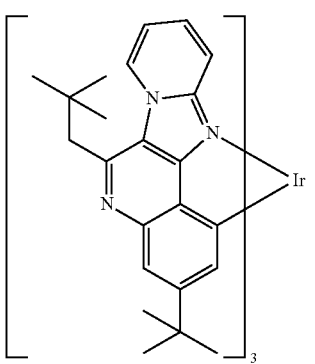
15
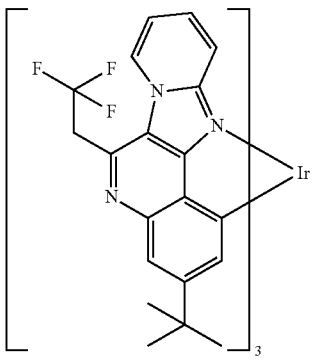
16
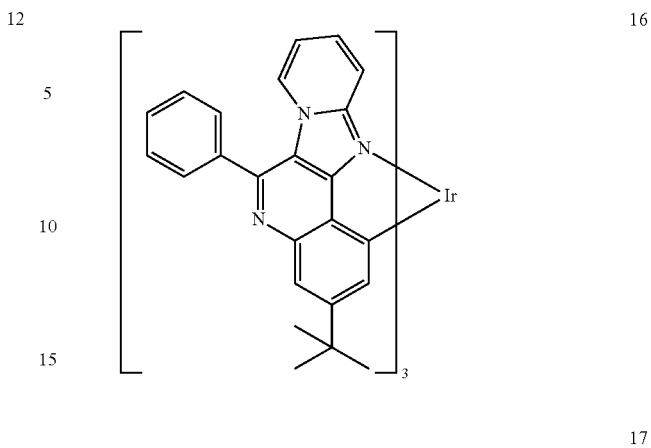
17
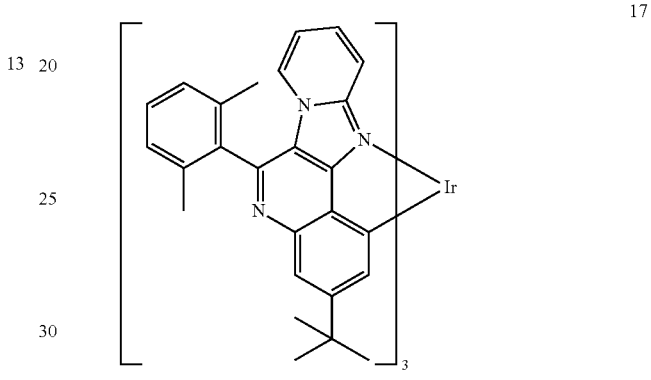
18
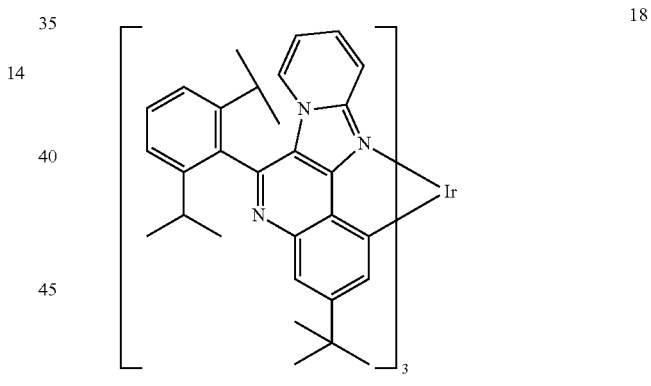
19
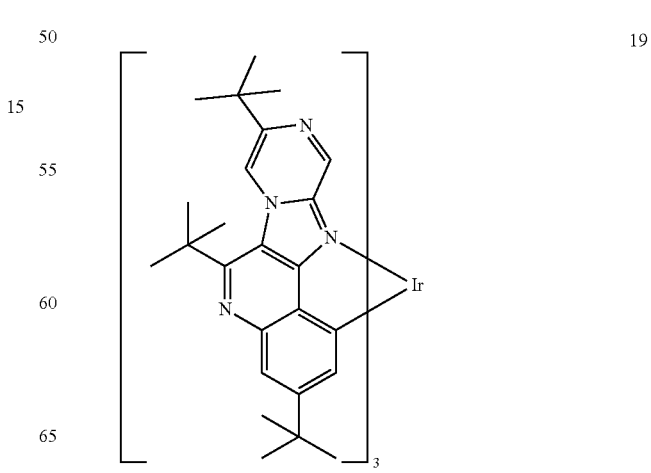

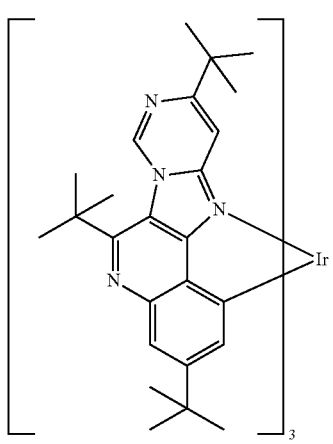
20
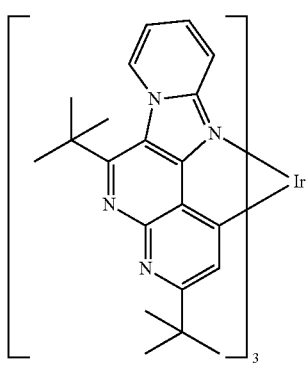
21
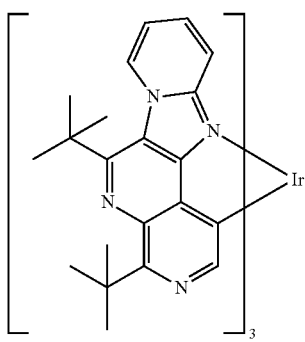
22
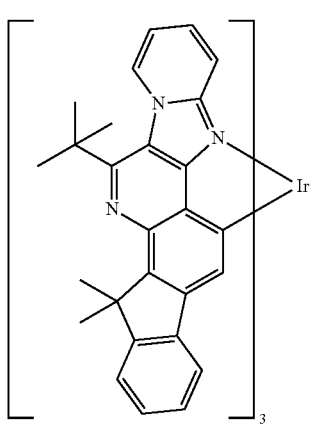
23
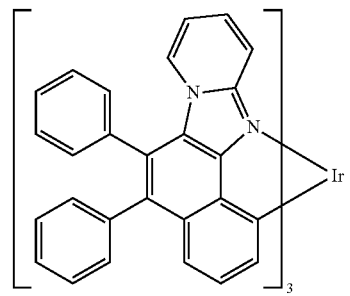
24
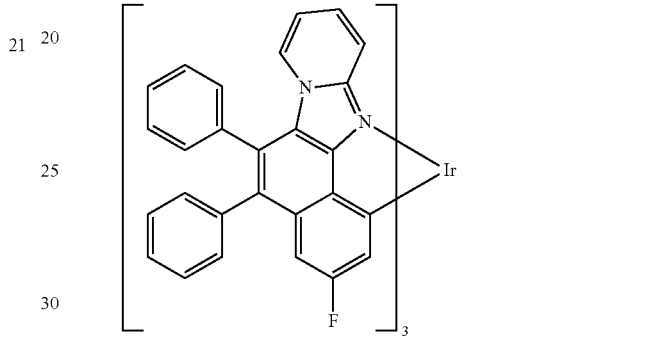
25
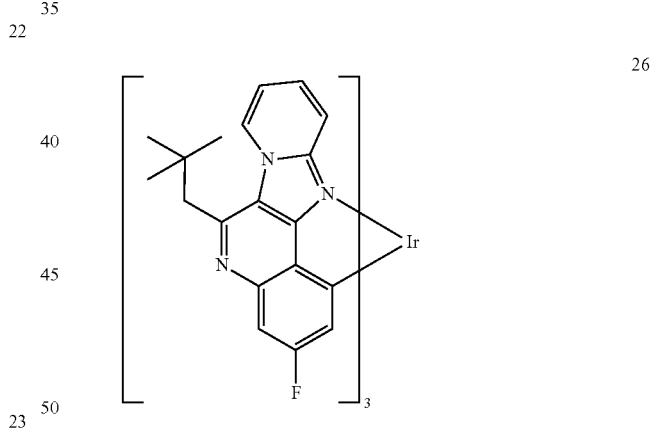
26
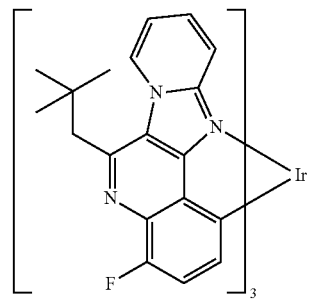
27

-continued
28
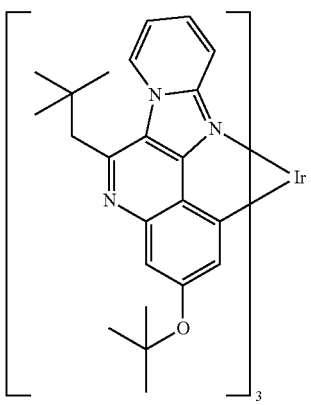
29
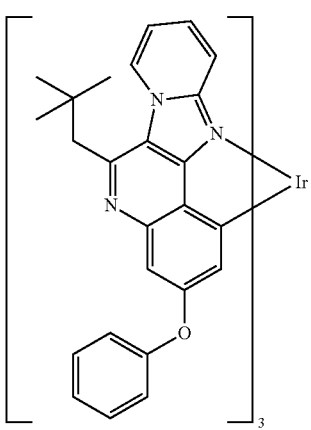
30
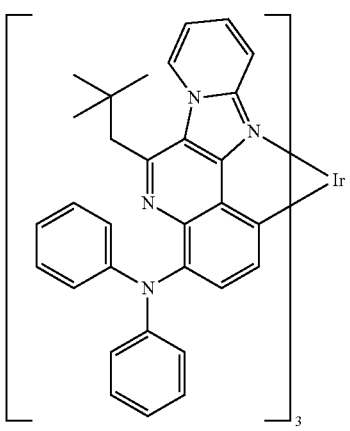
31
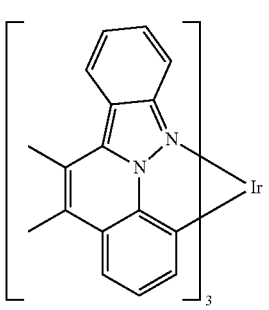
-continued
32
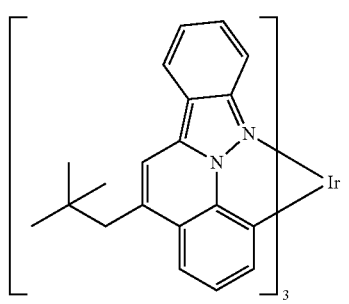
33
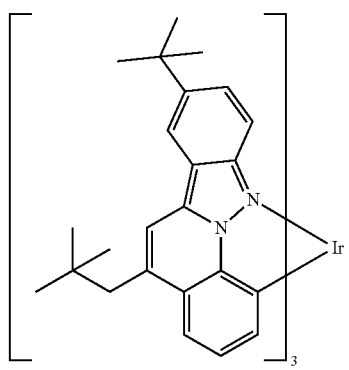
34
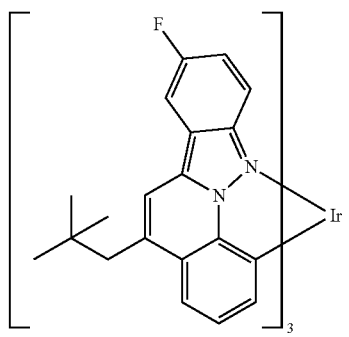
35
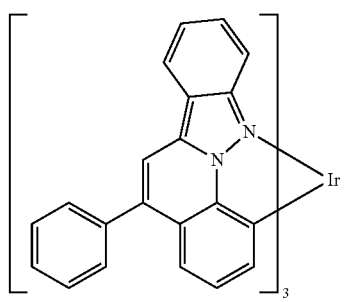
36
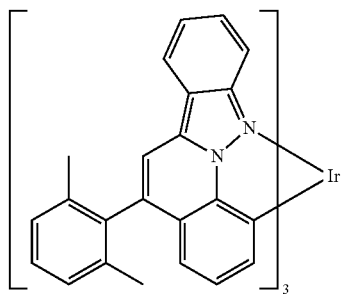

37
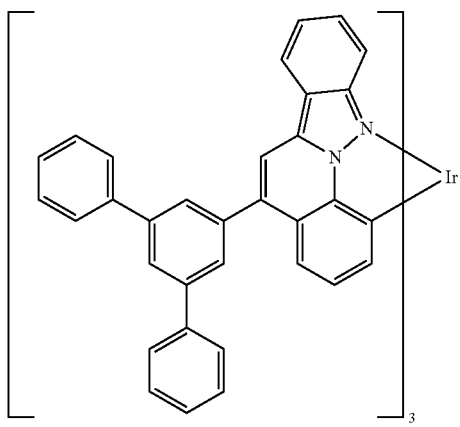
38
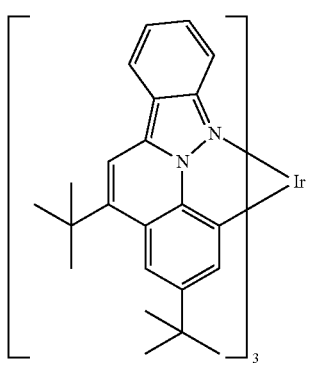
39
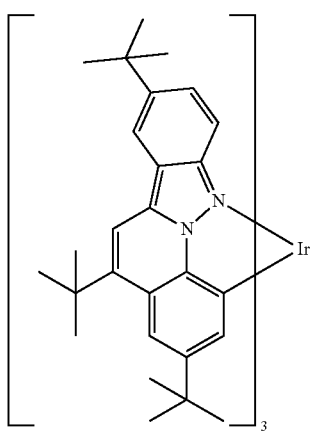
40
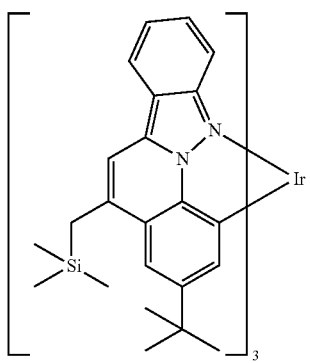
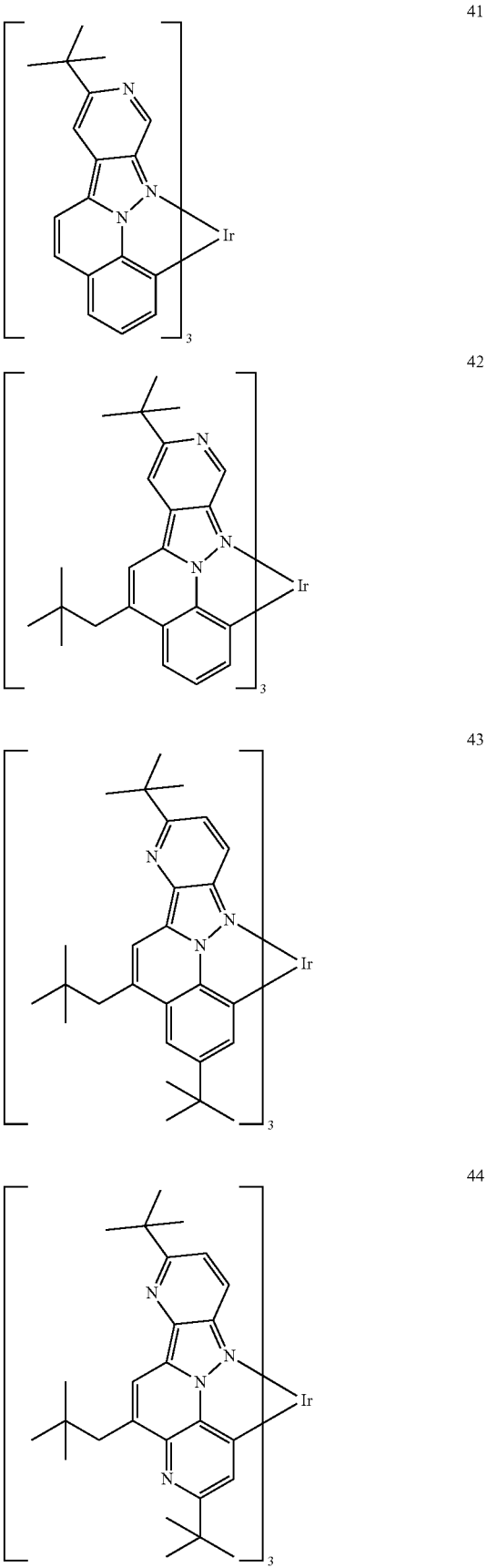

45
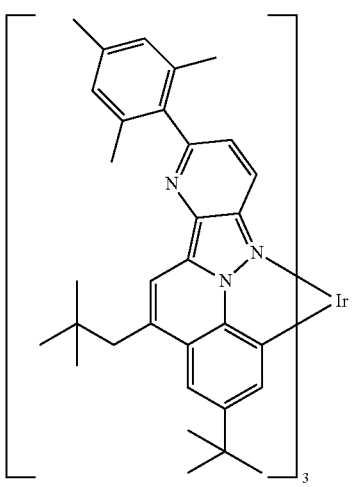
46
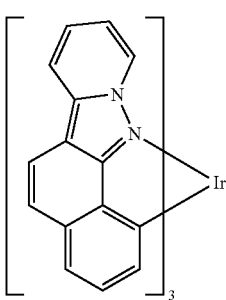
47
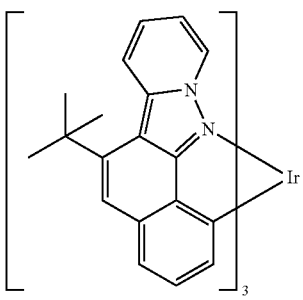
48
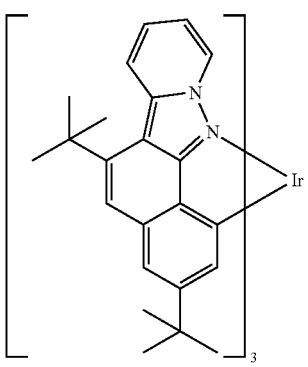
49
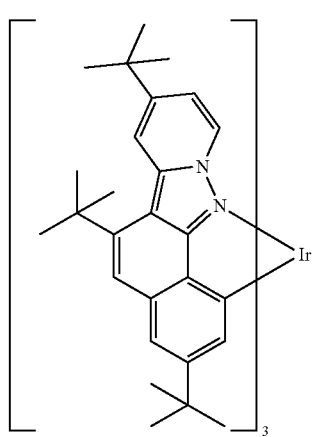
50
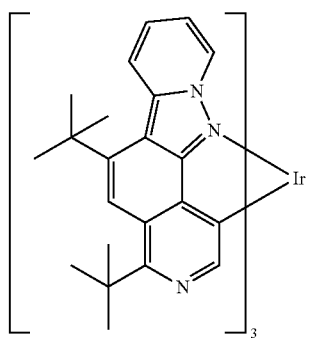
51
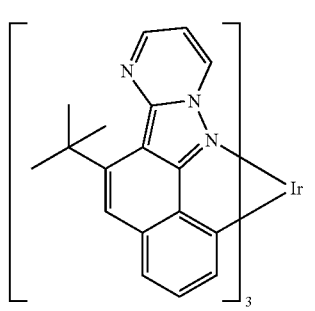
52
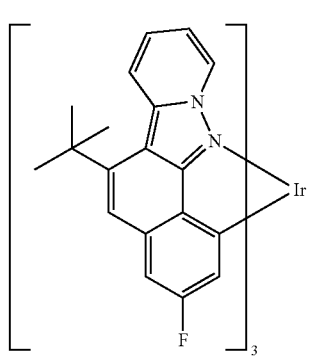

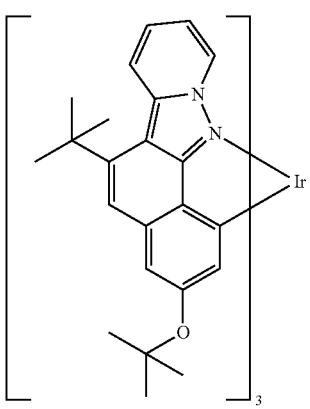
53
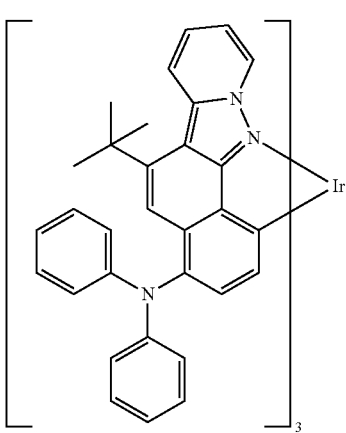
54
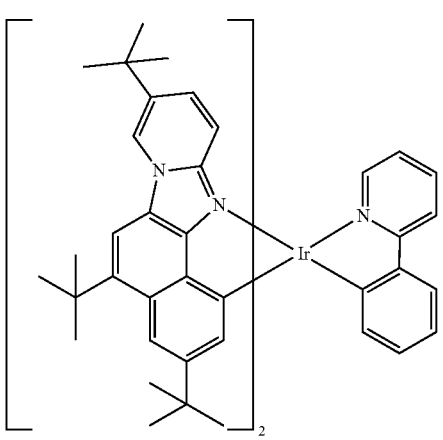
55
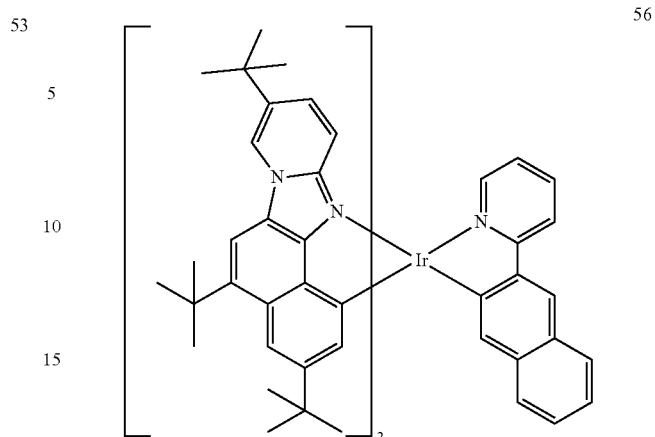
56
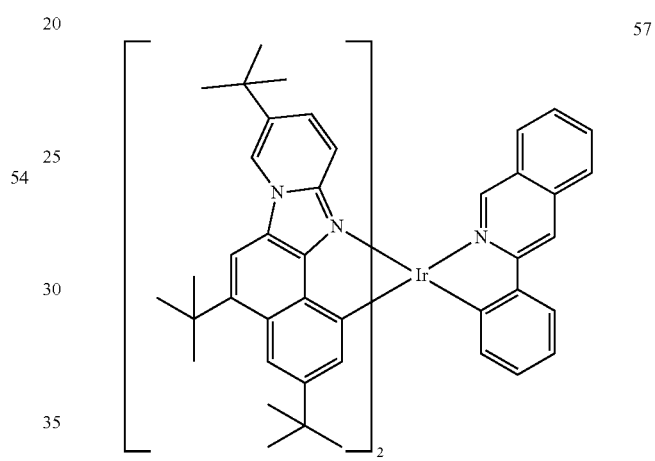
57
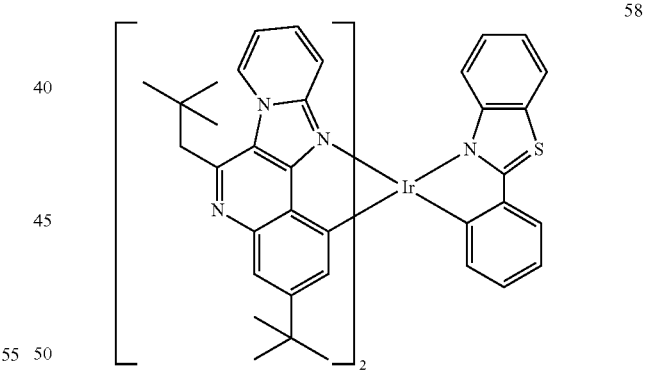
58
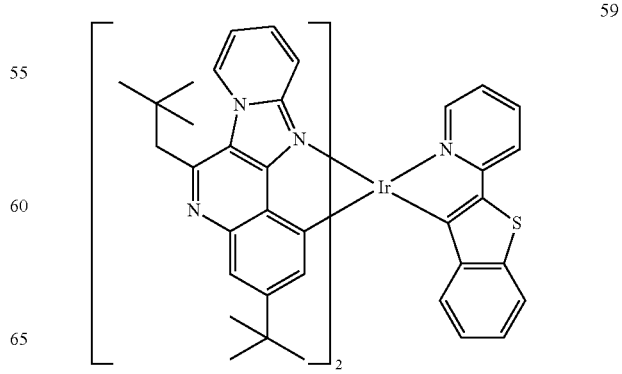
59

60

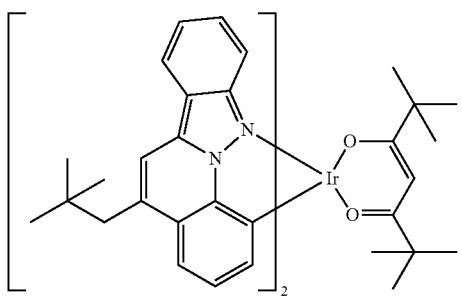

61

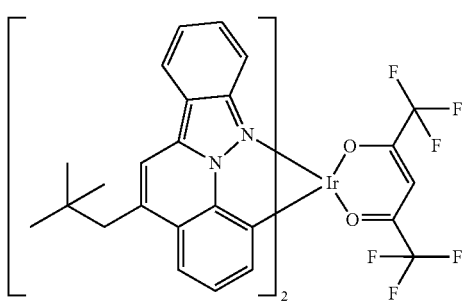

62

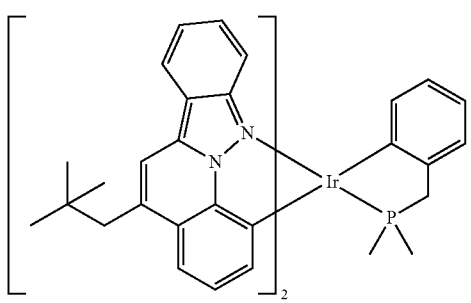

63

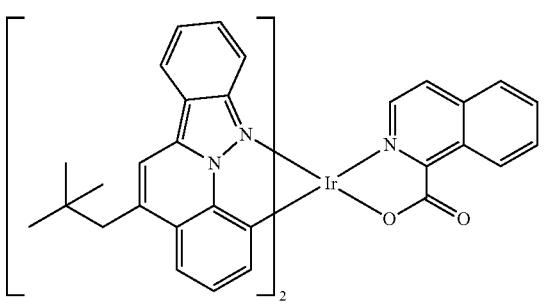

64

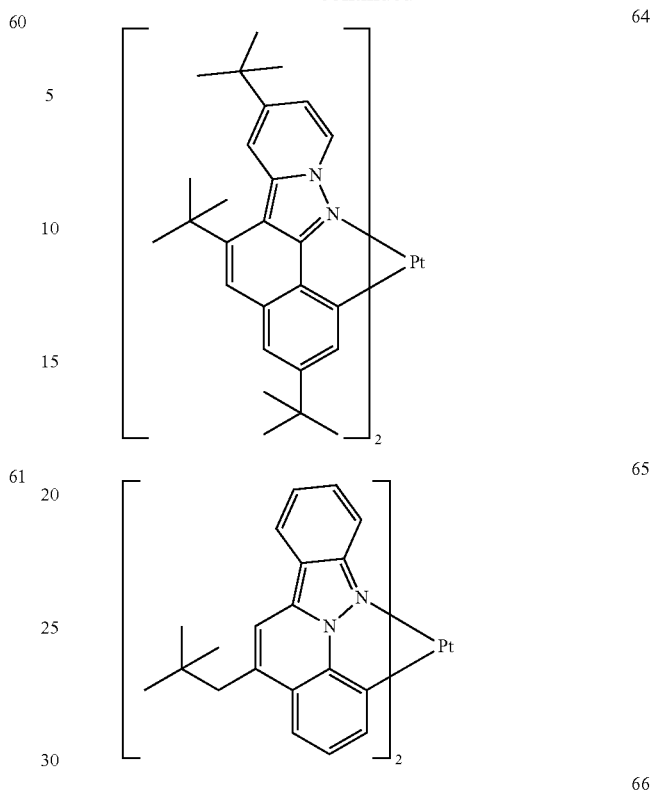

65

66

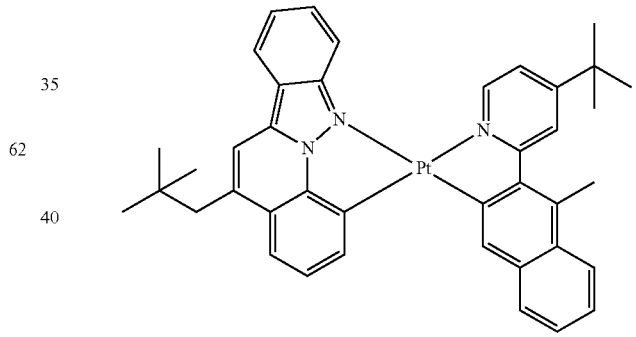

The complexes of the formula (1) described above or the preferred embodiments indicated above can be used as active component in the electronic device. An electronic device is taken to mean a device which comprises an anode, a cathode and at least one layer, where this layer comprises at least one organic or organometallic compound. The electronic device according to the invention thus comprises an anode, a cathode and at least one layer which comprises at least one compound of the formula (1) given above. Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), comprising at least one compound of the formula (1) given above in at least one layer. Particular preference is given to organic electroluminescent devices. Active components are generally the organic or inorganic materials which have been introduced between the anode and cathode, for example charge injection, charge-transport or charge-blocking materials, but in particular emission materials and matrix materials. The compounds according to the invention exhibit particularly good properties as emission material in organic electroluminescent devices. Organic electroluminescent devices are therefore a preferred embodiment of the invention.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers, charge-generation layers and/or organic or inorganic p/n junctions. Interlayers which have, for example, an exciton-blocking function and/or control the charge balance in the electroluminescent device may likewise be introduced between two emitting layers. However, it should be pointed out that each of these layers does not necessarily have to be present. The organic electroluminescent device may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013), or systems which have more than three emitting layers. It may also be a hybrid system, where one or more layers fluoresce and one or more other layers phosphoresce. It is likewise possible to generate white emission by two or more emitters which emit in different colours being present in the same emission layer.

In a preferred embodiment of the invention, the organic electroluminescent device comprises the compound of the formula (1) or the preferred embodiments indicated above as emitting compound in one or more emitting layers.

If the compound of the formula (1) is employed as emitting compound in an emitting layer, it is preferably employed in combination with one or more matrix materials. The mixture comprising the compound of the formula (1) and the matrix material comprises between 0.1 and 99% by vol., preferably between 1 and 90% by vol., particularly preferably between 3 and 40% by vol., especially between 5 and 15% by vol., of the compound of the formula (1), based on the mixture as a whole comprising emitter and matrix material. Correspondingly, the mixture comprises between 99.9 and 1% by vol., preferably between 99 and 10% by vol., particularly preferably between 97 and 60% by vol., especially between 95 and 85% by vol., of the matrix material, based on the mixture as a whole comprising emitter and matrix material.

The matrix material employed can in general be all materials which are known for this purpose in accordance with the prior art. The triplet level of the matrix material is preferably higher than the triplet level of the emitter.

Suitable matrix materials for the compounds according to the invention are ketones, phosphine oxides, sulfoxides and sulfones, for example in accordance with WO 2004/013080, WO 2004/093207, WO 2006/005627 or WO 2010/006680, triarylamines, carbazole derivatives, for example CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example in accordance with WO 2007/063754 or WO 2008/056746, indenocarbazole derivatives, for example in accordance with WO 2010/136109 or WO 2011/000455, azacarbazoles, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, diazasilole derivatives, for example in accordance with WO 2010/054729, diazaphosphole derivatives, for example in accordance with WO 2010/054730, triazine derivatives, for example in accordance with WO 2010/015306, WO 2007/063754 or WO 2008/056746, zinc complexes, for example in accordance with EP 652273 or WO 2009/062578, dibenzofuran derivatives, for example in accordance with WO 2009/148015, or bridged carbazole derivatives, for example in accordance with US 2009/0136779, WO 2010/050778 or the unpublished applications DE 102009048791.3 and DE 102010005697.9.

It may also be preferred to employ a plurality of different matrix materials as a mixture, in particular at least one electron-conducting matrix material and at least one hole-conducting matrix material. A preferred combination is, for example, the use of an aromatic ketone, a triazine derivative or a phosphine oxide derivative with a triarylamine derivative or a carbazole derivative as mixed matrix for the metal complex according to the invention. Preference is likewise given to the use of a mixture of a charge-transporting matrix material and an electrically inert matrix material which is not involved or not significantly involved in charge transport, as described, for example, in WO 2010/108579.

It is furthermore preferred to employ a mixture of two or more triplet emitters together with a matrix. The triplet emitter having the shorter-wave emission spectrum serves as co-matrix for the triplet emitter having the longer-wave emission spectrum here. Thus, for example, the complexes of the formula (1) according to the invention can be employed as emitters together with a metal complex emitting at shorter wavelength as co-matrix.

The compounds according to the invention can also be employed in other functions in the electronic device, for example as hole-transport material in a hole-injection or -transport layer, as charge-generation material or as electron-blocking material. The complexes according to the invention can likewise be employed as matrix material for other phosphorescent metal complexes in an emitting layer.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag, may also be used in addition to the said metals, in which case combinations of the metals, such as, for example, Mg/Ag, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). Organic alkali-metal complexes, for eample Liq (lithium quinolinate), are likewise suitable for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/NiO$_x$, Al/PtO$_x$) may also be preferred. For some applications, at least one of the electrodes must be transparent or partially transparent in order either to facilitate irradiation ofO the organic material (O-SCs) or the coupling-out of light (OLEDs/PLEDs, O-LASERs). Preferred anode materials here are conductive mixed metal oxides. Particular preference is given to indium tin oxide (ITO) or indium zinc oxide (IZO). Preference is furthermore given to conductive, doped organic materials, in particular conductive doped polymers, for example PEDOT, PANI or derivatives of these polymers All materials as are used in accordance with the prior art for the layers can generally be used in the further layers, and the person skilled in the art will be able to combine each of these materials with the materials according to the invention in an electronic device without inventive step.

The device is correspondingly structured (depending on the application), provided with contacts and finally hermetically sealed, since the lifetime of such devices is drastically shortened in the presence of water and/or air.

Preference is furthermore given to an organic electroluminescent device, characterised in that one or more layers are coated by means of a sublimation process, in which the materials are vapour-deposited in vacuum sublimation units at an initial pressure of usually less than $10^{-5}$ mbar, preferably less than $10^{-6}$ mbar. It is also possible for the initial pressure to be even lower or even higher, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing or nozzle printing, but particularly preferably LITI (light induced thermal imaging, thermal transfer printing) or ink-jet printing. Soluble compounds are necessary for this purpose, which are obtained, for example, through suitable substitution.

The organic electroluminescent device may also be produced as a hybrid system by applying one or more layers from solution and applying one or more other layers by vapour deposition. Thus, for example, it is possible to apply an emitting layer comprising a compound of the formula (1) and a matrix material from solution and to apply a hole-blocking layer and/or an electron-transport layer on top by vacuum vapour deposition.

These processes are generally known to the person skilled in the art and can be applied by him without problems to organic electroluminescent devices comprising compounds of the formula (1) or the preferred embodiments indicated above.

The electronic devices according to the invention, in particular organic electroluminescent devices, are distinguished by the following surprising advantages over the prior art:

1. Organic electroluminescent devices comprising compounds of the formula (1) as emitting materials have a very good lifetime.
2. Organic electroluminescent devices comprising compounds of the formula (1) as emitting materials have excellent efficiency.
3. The metal complexes according to the invention give access to organic electroluminescent devices which phosphoresce in the green, yellow, orange or red colour regions.
4. The metal complexes according to the invention are readily accessible synthetically and in high yield.

These advantages mentioned above are not accompanied by an impairment of the other electronic properties.

The invention is explained in greater detail by the following examples, without wishing to restrict it thereby. The person skilled in the art will be able to produce further electronic devices according to the invention without inventive step on the basis of the descriptions and will thus be able to carry out the invention throughout the range claimed.

EXAMPLES

The following syntheses are carried out, unless indicated otherwise, under a protective-gas atmosphere in dried solvents. The metal complexes are in addition handled with exclusion of light. The solvents and reagents can be purchased from Sigma-ALDRICH or ABCR. The numbers indicated for the compounds known from the literature relate to the CAS numbers.

1) Synthesis of the Ligands

Example 1

6-tert-Butyl-5,6b,11-triazabenzo[a]fluorene (L1)

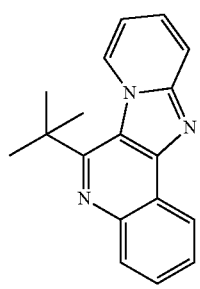 [SMILES: CC(C)(C)c1nc2ccccc2c2nc3ccccn3c12]

Preparation analogous to S. Sharma et al., J. Comb. Chem. 2007, 9, 783. A mixture of 20.9 g (100 mmol) of 2-imidazo[1,2-a]pyridin-2-ylphenylamine [127219-06-1], 42.1 g (500 mmol) of 2,2-dimethylpropanal [630-19-3] and 1.9 g (10 mmol) of p-toluenesulfonic acid hydrate in 500 ml of xylene is heated under reflux for 16 h, during which the water formed is removed by azeotropic distillation and a gentle stream of air is passed into the solution. After cooling, the solvent is removed in vacuo, the residue is taken up in 1000 ml of ethyl acetate, washed twice with 500 ml of water each time, once with 500 ml of saturated sodium chloride solution and dried over magnesium sulfate. After recrystallisation from ethanol twice, the solid is freed from low-boiling and non-volatile secondary components by sublimation (p about $1\times10^{-5}$ mbar, T about 180° C.). Yield: 9.1 g (33 mmol), 33%, purity: about 99.5% (NMR).

Example 2

5-tert-Butylindazolo[2,3-a]quinoline (L2)

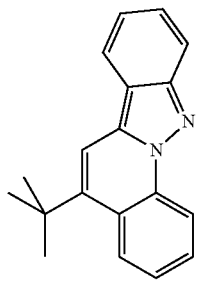 [SMILES: CC(C)(C)c1cc2c3ccccc3nn2c2ccccc12]

Preparation analogous to N. Shindoh, J. Org. Chem. 2008, 73, 7451.

Step 1: 2-(2-Nitrophenyl)-4-tert-butylquinoline

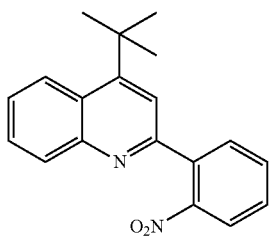 [SMILES: CC(C)(C)c1cc(-c2ccccc2[N+](=O)[O-])nc2ccccc12]

37.5 ml (15 mmol) of bis(trifluoromethanesulfonyl)amine [82113-65-3] (0.4 M solution in toluene) are added dropwise at room temperature to a solution of 22.6 g (100 mmol) of N-[2-nitrophenyl]methylene]phenylamine [1624-50-6] and 10.1 g (120 mmol) of 3,3-dimethylbut-1-ene [558-37-2] in 300 ml of 1,2-dichloroethane, and the mixture is subsequently stirred at 70° C. for 4 h. After cooling to room temperature, 50.0 g (220 mmol) of 2,3-dichloro-5,6-dicyano-1,4-benzoquinone [84-58-2] are added in portions, the mixture is stirred until the exothermic reaction has subsided and is finally warmed at 50° C. for a further 1 h. After cooling, the mixture is diluted with 1000 ml of chloroform, filtered through a Celite bed, the organic phase is washed twice with 300 ml of saturated sodium hydrogencarbonate solution each time, dried over magnesium sulfate, filtered through an aluminium oxide bed (aluminium oxide, basic, activity grade 1), the solvent is removed in vacuo, and the residue is recrystallised from ethanol. Yield: 22.7 g (74 mmol), 74%, purity: about 98% (NMR).

Step 2

A solution of 15.3 g (50 mmol) of 2-(2-nitrophenyl)-4-tert-butylquinoline and 34.1 g (130 mmol) of triphenylphosphine in 150 ml of o-dichlorobenzene is heated under reflux for 12 h. After cooling, the solvent is removed in vacuo, the residue is recrystallised twice from ethyl acetate and then chromatographed on silica gel (DCM:heptane 3:1, v:v+0.2% of triethylamine). The solid obtained in this way is freed from readily volatile and non-volatile secondary components by fractional sublimation (p about $1\times10^{-5}$ mbar, T about 180° C.). Yield: 8.8 g (32 mmol), 64%, purity: about 99.5% (NMR).

The following are prepared analogously:

| Ex. | Olefin | Product | Yield |
|---|---|---|---|
| 3 | 762-62-9 | L3 | 58% |
| 4 | 1524-26-1 | L4 | 30% |
| 5 | 769-25-5 | L5 | 22% |

Example 46

6-Mesityl-5,6b,11-triazabenzo[a]fluorene (L46)

Preparation analogous to Example 1, using 500 mmol of 2,4,6-trimethylbenzaldehyde [487-68-3] instead of 500 mmol of 2,2-dimethylpropanal. Yield: 7.1 g (21 mmol), 21%, purity: about 99.5% (NMR).

The following compounds are prepared analogously from the corresponding aldehdes:

| Ex. | Aldehyde | Product | Yield |
|---|---|---|---|
| 47 | 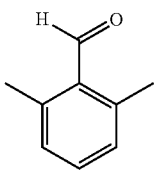<br>1123-56-4 | 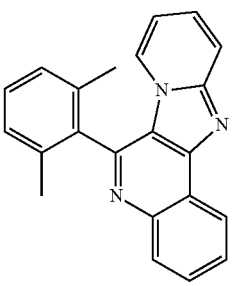<br>L47 | 32% |
| 48 | 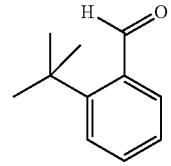<br>16358-79-5 | 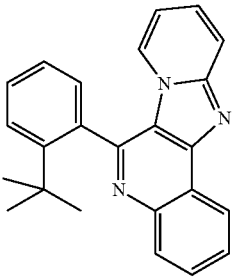<br>L48 | 26% |
| 49 | 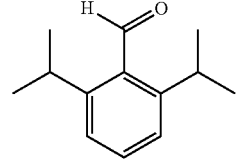<br>179554-06-4 | 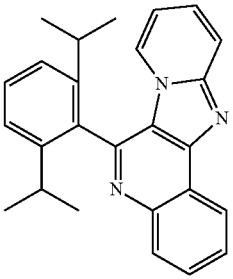<br>L49 | 14% |
| 50 | 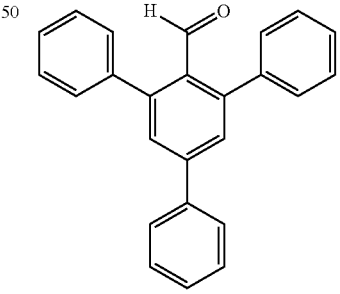<br>85390-98-3 | 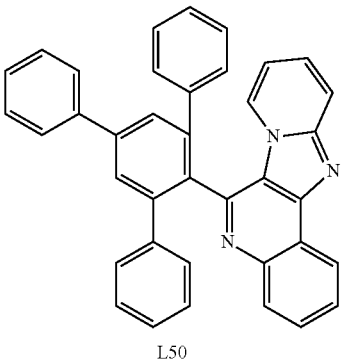 [SMILES: c1ccc(-c2cc(-c3ccccc3)c(-c3nc4ccccc4c4nc5ccccn5c34)c(-c3ccccc3)c2)cc1]<br>L50 | 17% |

-continued

| Ex. | Aldehyde | Product | Yield |
|---|---|---|---|
| 51 | 437-81-0 | L51 | 26% |
| 52 | 3392-97-0 | L52 | 21% |
| 53 | 6140-64-3 | L53 | 23% |
| 54 | 3805-10-5 | L54 | 26% |
| 55 | 2987-16-8 | L55 | 34% |

Example 56

6,9-Di-tert-butyl-5,6b,8,11-tetraazabenzo[a]fluorene (L56)

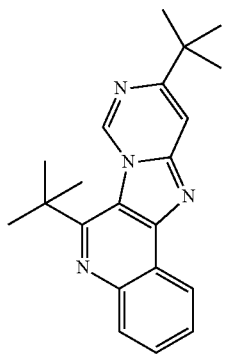 [SMILES: CC(C)(C)c1cc2nc3c4ccccc4nc(C(C)(C)C)c3n2cn1]

A solution of 15.1 g (100 mmol) of 6-tert-butylpyrimidin-4-ylamine [3435-27-6] and 24.4 g (100 mmol) of 2-bromo-1-(2-nitrophenyl)ethanone [6851-99-6] in 300 ml of ethanol is heated under reflux for 8 h. The solvent is removed in vacuo, the residue is taken up in 200 ml of water, the mixture is rendered alkaline by addition of 2 N NaOH, the aqueous phase is extracted three times with 100 ml of dichloromethane each time, the organic phase is washed once with 100 ml of saturated sodium chloride solution, and the dichloromethane is removed in vacuo. The oily residue is dissolved in 500 ml of ethanol, 112.8 g (500 mmol) of tin(II) chloride dihydrate are added, and the mixture is heated under reflux for 2 h. After cooling, the reaction mixture is poured into 1000 ml of ice-water, the mixture is rendered weakly alkaline by addition of saturated sodium hydrogencarbonate solution, 500 ml of ethyl acetate are added, the mixture is filtered through a short Celite bed, the organic phase is separated off, washed once with 300 ml of water and once with 300 ml of saturated sodium chloride solution, and the solvent is then removed in vacuo. The 2-(7-tert-butylimidazo[1,2-c]pyrimidin-2-yl)phenylamine obtained in this way is reacted further as described in Example 1 with 42.1 g (500 mmol) of 2,2-dimethylpropanal [630-19-3] and 1.9 g (10 mmol) of p-toluenesulfonic acid hydrate. Yield: 9.0 g (27 mmol), 27%, purity: about 99.5% (NMR).

The following compounds are prepared analogously from the corresponding amines and aldehydes:

| Ex. | Amine | Aldehyde | Product | Yield |
|---|---|---|---|---|
| 57 | (structure, NH₂) | (structure) 1123-56-4 | L57 | 24% |
| 58 | (structure, NH₂) 59489-38-2 | (structure) 630-19-3 | L58 | 24% |

-continued
| Ex. | Amine | Aldehyde | Product | Yield |
|---|---|---|---|---|
| 59 | 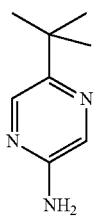 59489-38-2 | 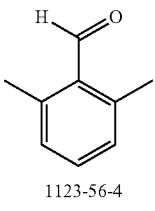 1123-56-4 | 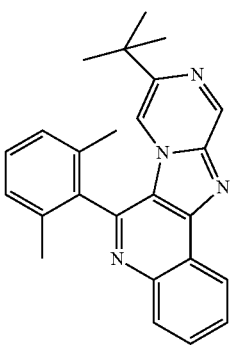 L59 | 27% |
| 60 | 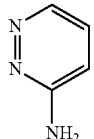 5469-70-5 | 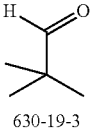 630-19-3 | 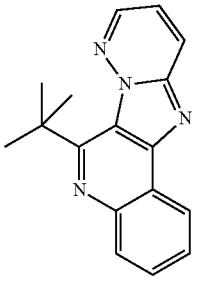 L60 | 22% |
| 61 | 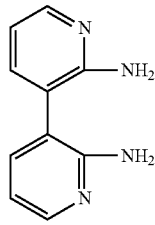 77200-37-4 | 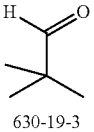 630-19-3 | 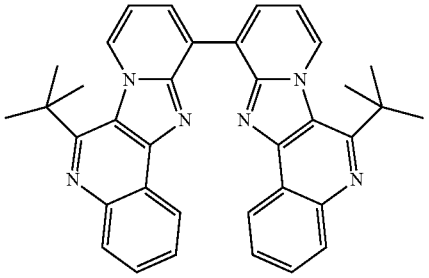 L61 | 14% |
| 62 | 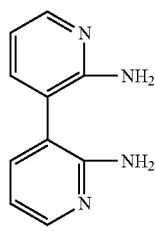 77200-37-4 | 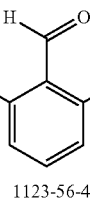 1123-56-4 | 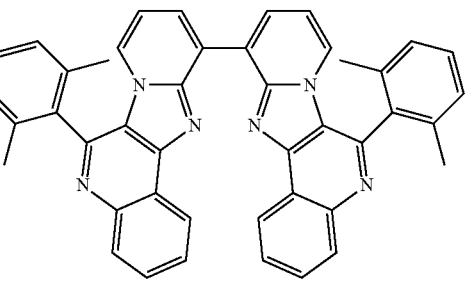 L62 | 11% |

Example 63

5-Methylindazolo[2,3-a]quinoline (L63)

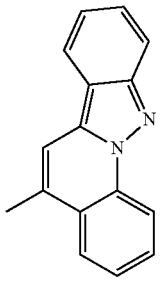 [SMILES: Cc1cc2c3ccccc3nn2c2ccccc12]

Step 1: 2-(4-Methylquinolin-2-yl)phenylamine hydrochloride

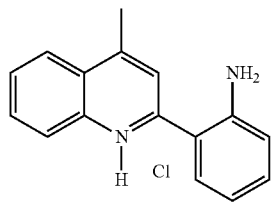

A mixture of 22.3 g (100 mmol) of 2-bromo-4-methylquinoline [64658-04-4], 13.7 g (120 mmol) of 2-aminobenzeneboronic acid, 1.2 g (1 mmol) of tetrakis(triphenylphosphino)palladium(0), 21.2 g (200 mmol) of sodium carbonate, 500 ml of toluene, 100 ml of ethanol and 300 ml of water is heated under reflux for 12 h. After cooling, the organic phase is separated off, washed twice with 200 ml of water each time, evaporated to about 100 ml in vacuo, 30 ml of concentrated hydrochloric acid are added with vigorous stirring, the mixture is stirred for a further 30 min., the hydrochloride is filtered off with suction, washed once with 50 ml of toluene and then dried in vacuo. Yield: 23.5 g (87 mmol), 87%, purity: about 98% (NMR).

The following compounds are prepared analogously from the corresponding quinolines and amines:

| Ex. | Quinoline | Amine | Product | Yield |
|---|---|---|---|---|
| 64 | 103858-47-5 | 5570-18-3 | | 80% |
| 65 | 103862-51-7 | 5570-18-3 | | 85% |
| 66 | 590372-17-1 | 5570-18-3 | | 71% |
| 67 | 596845-29-3 | 5570-18-3 | | 73% |

-continued

| Ex. | Quinoline | Amine | Product | Yield |
|---|---|---|---|---|
| 68 | 133131-93-8 | 5570-18-3 | | 93% |
| 60 | 103858-47-5 | 850689-37-1 | | 89% |
| 70 | 103858-47-5 | 948592-72-1 | | 85% |
| 71 | 103858-47-5 | 1155372-87-4 | | 77% |
| 72 | 1092837-92-7 | 948592-72-1 | | 63% |
| 73 | 103858-47-5 | 1225227-87-1 | | 65% |

| Ex. | Quinoline | Amine | Product | Yield |
|---|---|---|---|---|
| 74 | 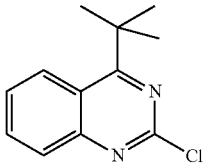<br>1092837-92-7 | 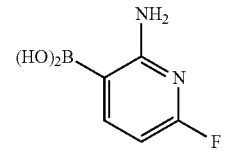<br>1225227-87-1 | 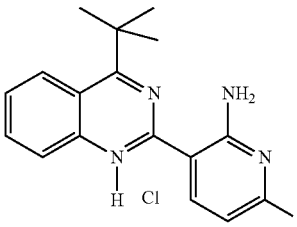 | 53% |

Step 2: 5-Methylindazolo[2,3-a]quinoline (L63)

9 ml of conc. hydrochloric acid are added to a suspension, cooled to 0° C., of 90.5 g (332 mmol) of 2-(4-methylquinolin-2-yl)phenylamine hydrochloride in 1300 ml of ice-water and 1000 ml of toluene in an open 10 l beaker, and a solution of 24.1 g (352 mmol) of sodium nitrite in 100 ml of water is then added dropwise, during which the temperature is kept below +5° C. When the addition is complete, the mixture is stirred for a further 20 min., a solution of 24.9 g (382 mmol) of sodium azide in 500 ml of ice-water is then allowed to run in slowly with vigorous stirring (note: evolution of gas, foaming!), and the mixture is then stirred further until the evolution of gas is complete. After warming to room temperature, the reaction mixture is rendered slightly alkaline using saturated sodium carbonate solution, the organic phase is separated off, washed once with 500 ml of water and once with 500 ml of saturated sodium chloride solution, dried over a mixture of sodium carbonate and magnesium sulfate, the desiccant is filtered off, and the filtrate is slowly heated to reflux under argon (care: evolution of gas from about 80° C.). After 8 h under reflux, the mixture is allowed to cool, filtered through 800 g of alumina (basic, activity grade 1), rinsed with 2000 ml of toluene, and the filtrate is then evaporated to dryness in vacuo. The yellow oil obtained in this way is recrystallised twice from about 300 ml of ethanol. The solid obtained in this way is freed from readily volatile and non-volatile secondary components by fractional sublimation (p about $1\times10^{-5}$ mbar, T about 180° C.). Yield: 48.8 g (210 mmol), 63%, purity: about 99.5% (NMR).

The following compounds are prepared analogously:

| Ex. | Starting material | Product | Yield |
|---|---|---|---|
| 75 | 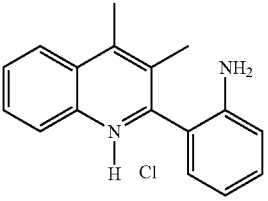 | 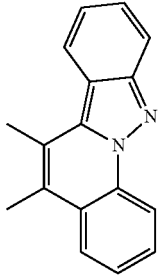<br>L75 | 66% |
| 76 | 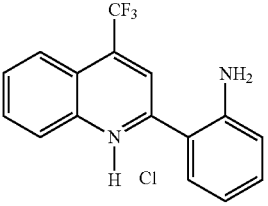 | 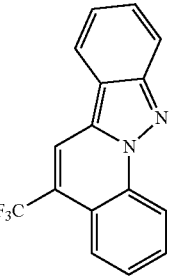<br>L76 | 60% |
| 77 | 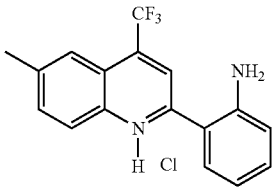 | 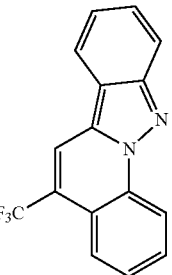<br>L77 | 51% |
| 78 | CF₃ structure | L78 structure | 56% |

| Ex. | Starting material | Product | Yield |
|---|---|---|---|
| 79 | 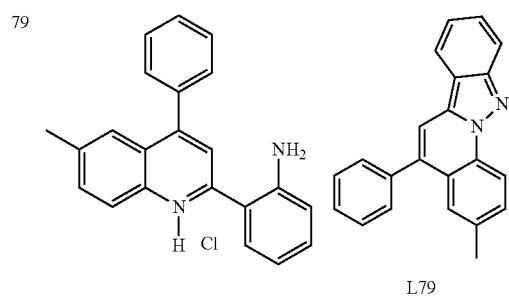 | 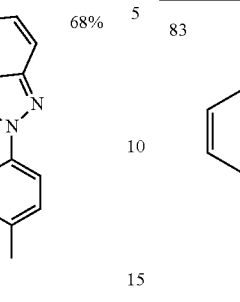 L79 | 68% |
| 80 | 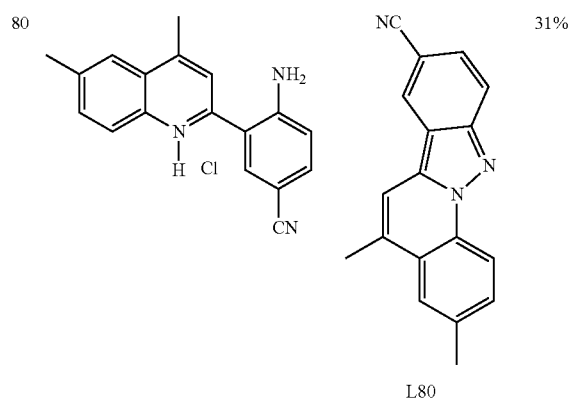 |  L80 | 31% |
| 81 | 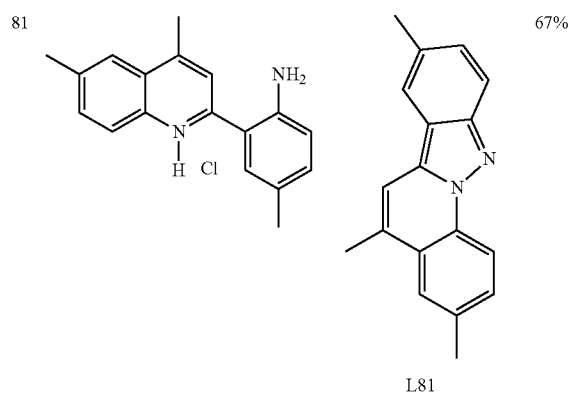 |  L81 | 67% |
| 82 | 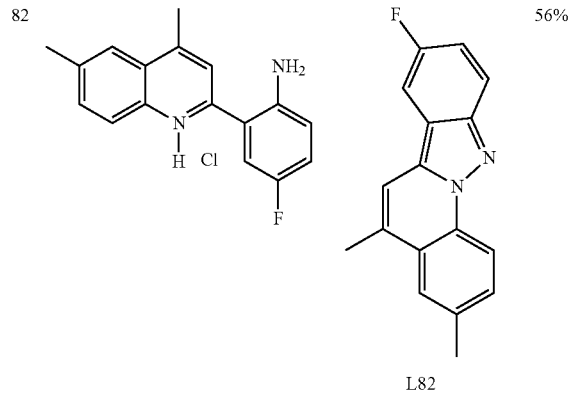 |  L82 | 56% |
| Ex. | Starting material | Product | Yield |
|---|---|---|---|
| 83 | 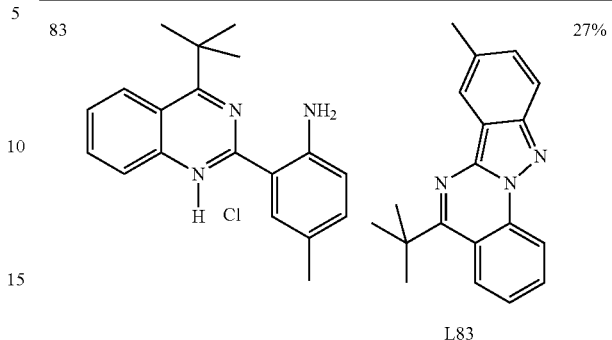 | L83 | 27% |
| 84 | 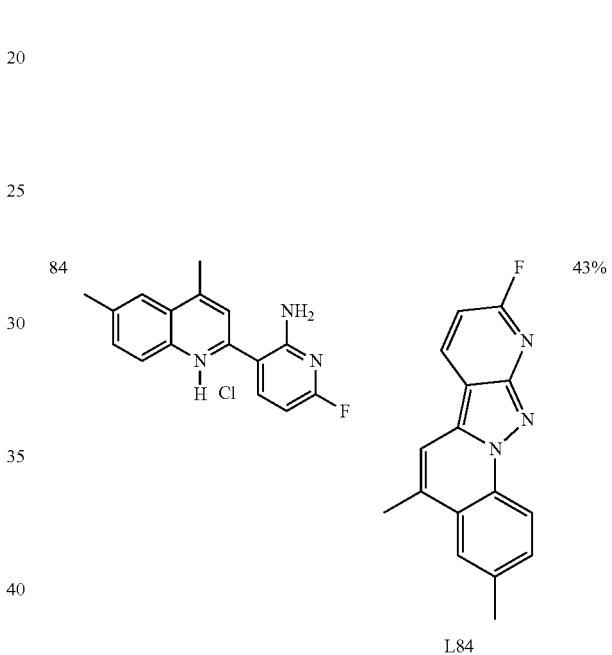 | L84 | 43% |
| 85 | 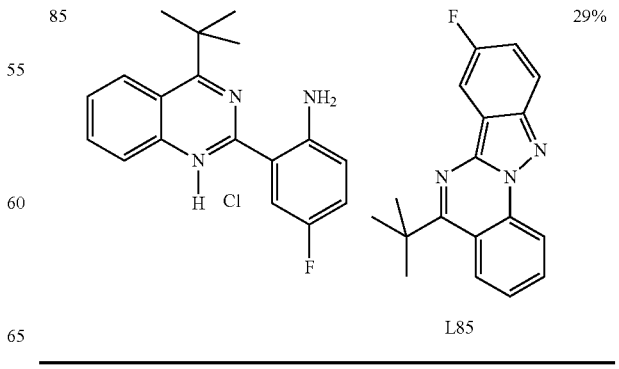 | L85 | 29% |

Example 86

3,5,8,3",5",8"-Hexamethyl[10,10]bi[indazolo[2,3]-quinolinyl] (L86)

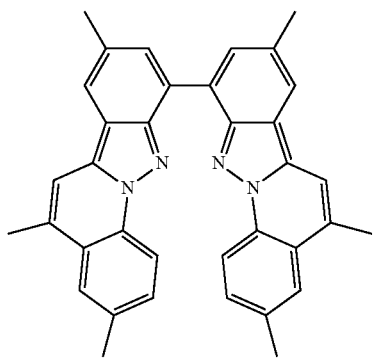

18.7 g (105 mmol) of N-bromosuccinimide are added in portions at 60° C. with exclusion of light to a solution of 51.9 g (100 mmol) of L81 in 300 ml of DMF, and the mixture is then stirred for a further 2 h. After removal of the DMF in vacuo, the oily residue is taken up in 500 ml of ethyl acetate, washed five times with 300 ml of water each time and once with 500 ml of saturated sodium chloride solution. The organic phase is evaporated to about 50 ml in vacuo, and 150 ml of methanol are added. After stirring for 12 h, the crystals formed are filtered off with suction, washed with 50 ml of methanol and dried in vacuo until all the methanol has been removed. The 10-bromo-3,5,8-trimethylindazolo[2,3-a]quinoline obtained in this way is dissolved in a mixture of 150 ml of dimethylacetamide and 300 ml of toluene, the solution is carefully degassed, 11.0 g (200 mmol) of manganese powder, 1.3 g (2 mmol) of bis(triphenylphosphino)nickel(11) chloride, 1.3 g (8 mmol) of bipyridine and 100 g of glass beads (diameter 5 mm) are added, and the mixture is stirred at 70° C. for 48 h. After cooling, the mixture is filtered through a short Celite bed in order to remove the glass beads, excess nickel and salts, rinsed with toluene, and the filtrate is then evaporated in vacuo. The oily residue is taken up in 1000 ml of toluene, washed three times with 500 ml of water each time, the organic phase is dried over magnesium sulfate, evaporated in vacuo to a volume of about 100 ml, and 300 ml of methanol are added dropwise. The solid is filtered off with suction and recrystallised three times from toluene/ethanol. The solid obtained in this way is freed from readily volatile and non-volatile secondary components by fractional sublimation (p about $1 \times 10^{-5}$ mbar, T about 300° C.). Yield: 13.5 g (26 mmol), 52%, purity: about 99.5% (NMR).

Example 87

10-Benzo[h]quinolin-2-yl-3,5,8-trimethyl-indazolo[2,3-a]-quinoline (L87)

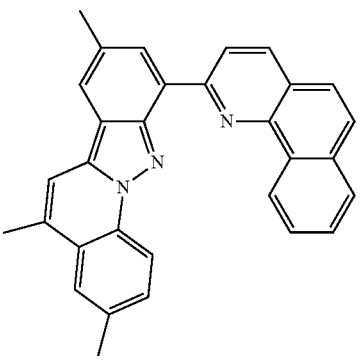 [SMILES: Cc1ccc2c(c1)c(C)cc1c3cc(C)cc(-c4ccc5ccc6ccccc6c5n4)c3nn21]

A mixture of 17.0 g (50 mmol) of 10-bromo-3,5,8-trimethylindazolo[2,3-a]-quinoline (Example 86), 19.8 g (65 mmol) of 2-(4,4,5,5-tetramethyl-1,3,2-dioxaborolan-2-yl)benzo[h]quinoline, 225 mg (1 mmol) of palladium(II) acetate, 1.8 g (6 mmol) of tri-o-tolylphosphine, 10.6 g (100 mmol) of sodium carbonate, 200 ml of toluene, 50 ml of dioxane and 300 ml of water is heated under reflux for 16 h. After cooling, the organic phase is separated off, washed twice with 300 ml of water, dried over magnesium sulfate, the organic phase is evaporated to dryness in vacuo, and the residue is recrystallised from toluene/ethanol. The solid obtained in this way is freed from readily volatile and non-volatile secondary components by fractional sublimation (p about $1 \times 10^{-5}$ mbar, T about 270° C.). Yield: 15.8 g (36 mmol), 72%, purity: about 99.5% (NMR).

The following compounds are prepared analogously:

| Ex. | Boronic acid | Product | Yield |
|---|---|---|---|
| 88 | (HO)₂B— (phenyl-pyridine), 833485-13-5 | L88 | 68% |

| Ex. | Boronic acid | Product | Yield |
|---|---|---|---|
| 89 | (HO)₂B-  881913-23-1 | 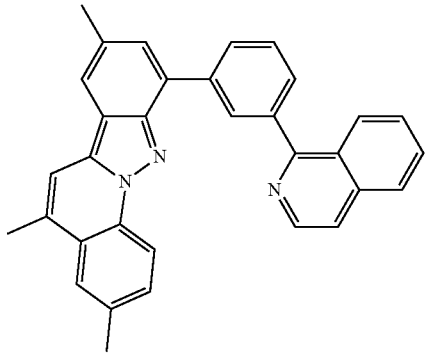 L89 | 70% |

Example 90

5-Methyl-10a,11-diazabenzo[a]fluorene (L90)

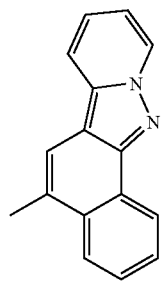 [SMILES: Cc1cc2c(nn3ccccc23)c2ccccc12]

Step 1:
4-Methyl-2-pyridin-2-ylnaphthalen-1-ylamine hydrochloride

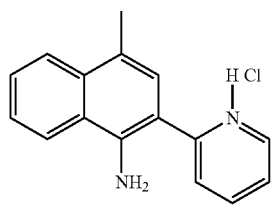

A mixture of 23.6 g (100 mmol) of 1-amino-2-bromo-4-methylnaphthalene [180411-16-9], 17.2 g (140 mmol) of pyridine-2-boronic acid [197958-29-5], 1.2 g (1 mmol) of tetrakis(triphenylphosphino)palladium(0), 21.2 g (200 mmol) of sodium carbonate, 500 ml of toluene, 100 ml of ethanol and 300 ml of water is heated under reflux for 12 h. After cooling, the organic phase is separated off, washed twice with 300 ml of water each time, evaporated to about 100 ml in vacuo, 30 ml of concentrated hydrochloric acid are added with vigorous stirring, the mixture is stirred for a further 30 min., the hydrochloride is filtered off with suction, washed once with 50 ml of toluene and then dried in vacuo. Yield: 22.1 g (81 mmol), 81%, purity: about 98% (NMR).

The following compounds are prepared analogously from the corresponding amines and boronic acids:

| Ex. | Amine | Boronic acid | Product | Yield |
|---|---|---|---|---|
| 91 | 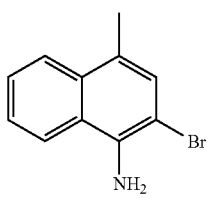 103858-47-5 | (HO)₂B- 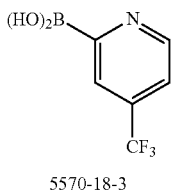 5570-18-3 | 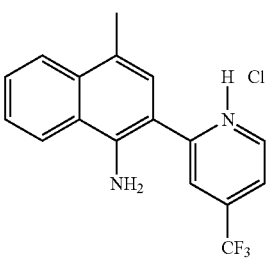 | 81% |

| Ex. | Amine | Boronic acid | Product | Yield |
|---|---|---|---|---|
| 92 | 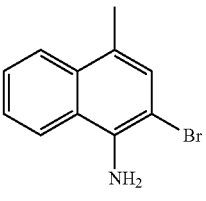<br>103858-47-5 | 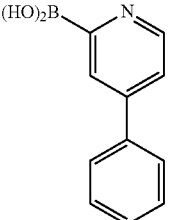<br>1257879-78-9 | 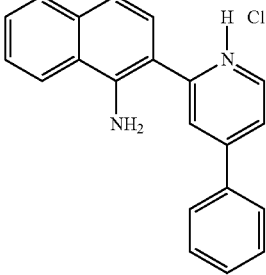 | 77% |
| 93 | 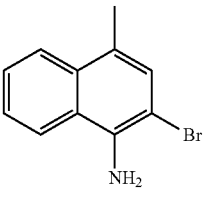<br>103858-47-5 | 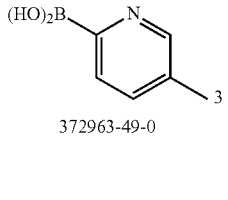<br>372963-49-0 | 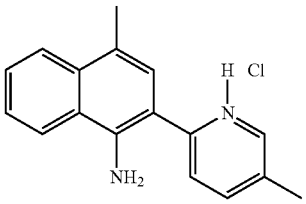 | 82% |
| 94 | 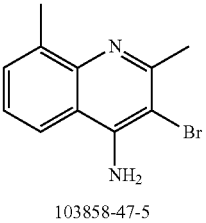<br>103858-47-5 | 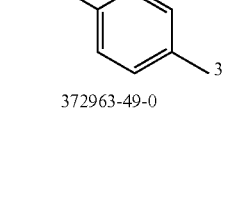<br>372963-49-0 | 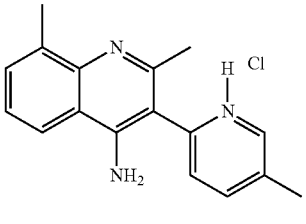 | 79% |
| 95 | 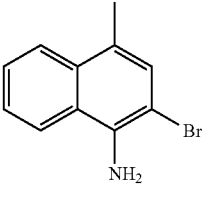<br>103858-47-5 | 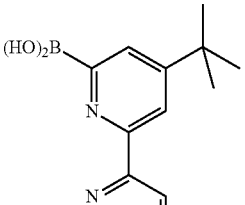<br>50 mmol of diboronic acid<br>879291-23-3 | 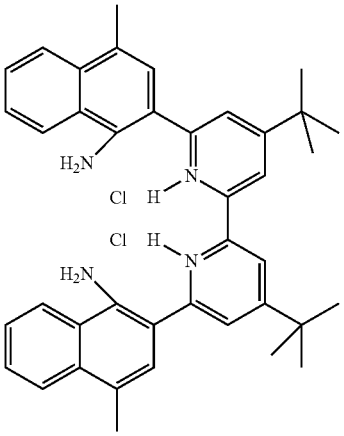 | 64% |

Step 2: 5-Methyl-10a,11-diazabenzo[a]fluorene (L90)

Preparation analogous Example 63, using 90.5 g (332 mmol) of 4-methyl-2-pyridin-2-ylnaphthalen-1-ylamine hydrochloride instead of 90.5 g (332 mmol) of 2-(4-methylquinolin-2-yl)phenylamine hydrochloride. Yield: 53.6 g (231 mmol), 70%, purity: about 99.5% (NMR).

The following compounds are prepared analogously:

| Ex. | Starting material | Product | Yield |
|---|---|---|---|
| 96 | | L96 | 64% |
| 97 | | L97 | 69% |
| 98 | | L98 | 71% |
| 99 | | L99 | 70% |

-continued

| Ex. | Starting material | Product | Yield |
|---|---|---|---|
| 100 | (structure shown, 165 mmol are employed) | L100 | 48% |

2) Synthesis of the Metal Complexes

1) Homoleptic Tris-Facial Iridium Complexes

Variant A: Trisacetylacetonatoiridium(III) as Iridium Starting Material

A mixture of 10 mmol of tris(acetylacetonato)iridium(III) [15635-87-7] and 60 mmol of ligand L is melted ($10^{-3}$ mbar) into a 50 ml glass ampoule in vacuo. The ampoule is heated at the stated temperature for the stated time, during which the molten mixture is stirred with the aid of a magnetic stirrer. After cooling (NOTE: the ampoules are usually under pressure!), the ampoule is opened, the sinter cake is stirred for 3 h with 100 g of glass beads (diameter 3 mm) in 100 ml of the suspension medium indicated and at the same time mechanically digested. The fine suspension is decanted off from the glass beads, the solid is filtered off with suction and dried in vacuo. The dry solid is placed on an aluminium oxide bed (basic, activity grade 1) with a depth of 10 cm in a hot extractor and then extracted with the extractant indicated (amount about 500 ml). When the extraction is complete, the extractant is evaporated to about 100 ml in vacuo. Metal complexes which have excessively good solubility in the extractant are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is less than 99.5%, the hot-extraction step is repeated, when a purity of 99.5-99.9% has been reached, the metal complex is heated or sublimed. The heating is carried out in a high vacuum (p about $10^{-6}$ mbar) in the temperature range 200-300° C. The sublimation is carried out in a high vacuum (p about $10^{-6}$ mbar) in the temperature range from about 320 to about 440° C., where the sublimation is preferably carried out in the form of a fractional sublimation.

Variant B: Tris(2,2,6,6-tetramethyl-3,5-heptanedionato) iridium as iridium starting material Procedure analogous to variant A, using 10 mmol of tris(2, 2,6,6-tetramethyl-3,5-heptanedionato)iridium [99581-86-9] instead of 10 mmol of tris(acetylacetonato)iridium(III) [15635-87-7].

| Ex. | Ligand L | Ir complex | Variant Reaction temp./ reaction time Suspension medium Extractant | Yield |
|---|---|---|---|---|
| 6 | L1 | Ir(L1)₃ | B 260° C./100 h DCM THF | 34% |

-continued
| Ex. | Ligand L | Ir complex | Variant Reaction temp./ reaction time Suspension medium Extractant | Yield |
|---|---|---|---|---|
| 7 | L2 | 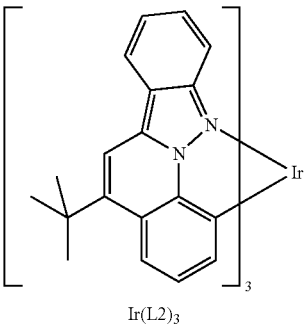<br>Ir(L2)₃ | A<br>260° C./60 h<br>DCM<br>THF | 37% |
| 8 | L3 | 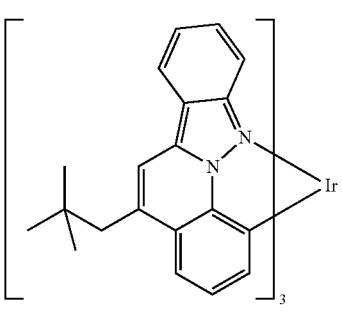<br>Ir(L3)₃ | such as Ir(L2)₃ | 31% |
| 9 | L4 | 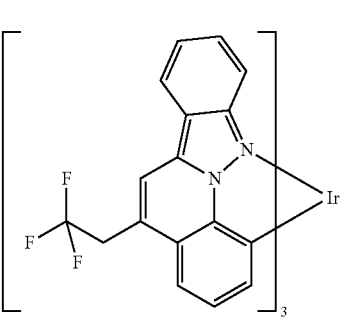<br>Ir(L4)₃ | such as Ir(L2)₃ | 17% |
| 10 | L5 | 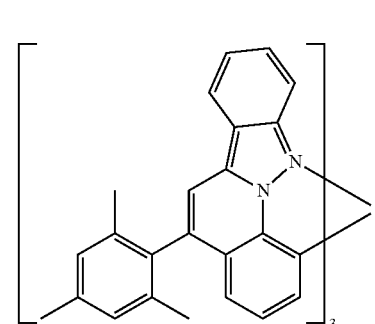<br>Ir(L5)₃ | such as Ir(L2)₃ | 24% |

-continued

| Ex. | Ligand L | Ir complex | Variant Reaction temp./reaction time Suspension medium Extractant | Yield |
|---|---|---|---|---|
| 101 | L46 | Ir(L46)₃ | B 290° C./100 h Acetone p-Xylene | 28% |
| 102 | L47 | Ir(L47)₃ | such as Ir(L46)₃ | 26% |
| 103 | L48 | Ir(L48)₃ | such as Ir(L46)₃ | 27% |
| 104 | L49 | Ir(L49)₃ | such as Ir(L46)₃ | 31% |
| 105 | L50 | Ir(L50)₃ | such as Ir(L46)₃ | 22% |
| 106 | L51 | Ir(L51)₃ | such as Ir(L46)₃ | 19% |
| 107 | L52 | Ir(L52)₃ | such as Ir(L46)₃ | 11% |
| 108 | L53 | Ir(L53)₃ | such as Ir(L46)₃ | 28% |
| 109 | L54 | Ir(L54)₃ | such as Ir(L46)₃ | 25% |
| 110 | L55 | Ir(L55)₃ | such as Ir(L46)₃ | 31% |
| 112 | L56 | Ir(L56)₃ | B 290° C./100 h Toluene p-Xylene | 28% |
| 113 | L57 | Ir(L57)₃ | such as Ir(L56)₃ | 28% |
| 114 | L58 | Ir(L58)₃ | such as Ir(L56)₃ | 26% |
| 115 | L59 | Ir(L59)₃ | such as Ir(L56)₃ | 30% |
| 116 | L60 | Ir(L60)₃ | such as Ir(L56)₃ | 29% |
| 117 | L63 | Ir(L63)₃ | B 290° C./100 h Acetone p-Xylene | 25% |
| 118 | L75 | Ir(L75)₃ | such as Ir(L63)₃ | 26% |

| Ex. | Ligand L | Ir complex | Variant Reaction temp./ reaction time Suspension medium Extractant | Yield |
|---|---|---|---|---|
| 119 | L76 | Ir(L76)$_3$ | such as Ir(L63)$_3$ | 28% |
| 120 | L77 | Ir(L77)$_3$ | such as Ir(L63)$_3$ | 14% |
| 121 | L78 | Ir(L78)$_3$ | such as Ir(L63)$_3$ | 16% |
| 122 | L79 | Ir(L79)$_3$ | such as Ir(L63)$_3$ | 29% |
| 123 | L80 | Ir(L80)$_3$ | such as Ir(L63)$_3$ | 8% |
| 124 | L81 | Ir(L81)$_3$ | such as Ir(L63)$_3$ | 28% |
| 125 | L82 | Ir(L82)$_3$ | such as Ir(L63)$_3$ | 19% |
| 126 | L83 | Ir(L83)$_3$ | such as Ir(L63)$_3$ | 26% |
| 127 | L84 | Ir(L84)$_3$ | such as Ir(L63)$_3$ | 18% |
| 128 | L85 | Ir(L85)$_3$ | such as Ir(L63)$_3$ | 18% |
| 129 | L90 | 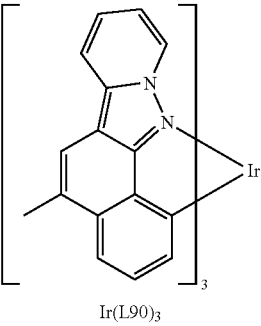  Ir(L90)$_3$ | B 290° C./100 h Acetone p-Xylene | 32% |
| 130 | L96 | Ir(L96)$_3$ | such as Ir(L90)$_3$ | 19% |
| 131 | L97 | Ir(L97)$_3$ | such as Ir(L90)$_3$ | 25% |
| 132 | L98 | Ir(L98)$_3$ | such as Ir(L90)$_3$ | 31% |
| 133 | L99 | Ir(L99)$_3$ | such as Ir(L90)$_3$ | 30% |

2) Heteroleptic Iridium Complexes

Variant A:

Step 1:

A mixture of 10 mmol of sodium bis(acetylacetonato)dichloroiridate(III) [770720-50-8] and 24 mmol of ligand L is melted into a 50 ml glass ampoule in vacuo ($10^{-3}$ mbar). The ampoule is heated at the stated temperature for the stated time, during which the molten mixture is stirred with the aid of a magnetic stirrer. After cooling (NOTE: the ampoules are usually under pressure!), the ampoule is opened, the sinter cake is stirred for 3 h with 100 g of glass beads (diameter 3 mm) in 100 ml of the suspension medium indicated and at the same time mechanically digested. The fine suspension is decanted off from the glass beads, the solid is filtered off with suction and dried in vacuo.

Step 2:

The crude chloro-bridged dimer of the formula [Ir(L)$_2$Cl]$_2$ obtained in this way is suspended in a mixture of 75 ml of 2-ethoxyethanol and 25 ml of water, 13 mmol of co-ligand CL and 15 mmol of sodium carbonate are added. After 20 h under reflux, a further 75 ml of water are added dropwise, the mixture is cooled, the solid is filtered off with suction, washed three times with 50 ml of water each time and three times with 50 ml of methanol each time and dried in vacuo. The dry solid is placed in a hot extractor on an aluminium oxide bed (basic, activity grade 1) with a depth of 10 cm and extracted with the extractant indicated (amount about 500 ml). When the extraction is complete, the extractant is concentrated to about 100 ml in vacuo. Metal complexes which have excessively good solubility in the extractant are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated; when a purity of 99.5-99.9% has been reached, the metal complex is heated or sublimed. The heating is carried out in a high vacuum (p about $10^{-6}$ mbar) in the temperature range 200-300° C. The sublimation is carried out in a high vacuum (p about $10^{-6}$ mbar) in the temperature range from about 300 to about 390° C., with the sublimation preferably being carried out in the form of a fractional sublimation.

| Ex. | Ligand L | Co-ligand CL | Ir complex Step 1: reaction temp./reaction time/suspension medium Step 2: extractant | Yield |
|---|---|---|---|---|
| 11 | L1 | 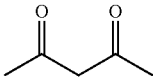 123-54-6 CL1 | 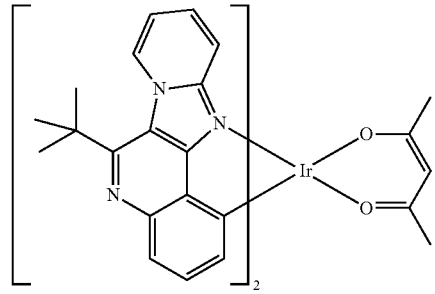 260° C./60 h/DCM THF Ir(L1)₂(CL1) | 38% |
| 12 | L1 | 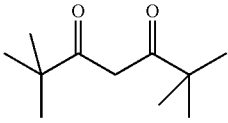 1118-71-4 CL2 | 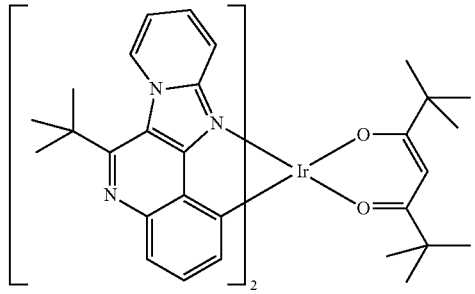 260° C./60 h/DCM THF Ir(L1)₂(CL2) | 36% |
| 13 | L1 | 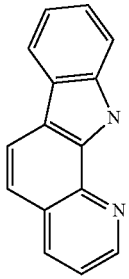 239-13-4 CL3 | 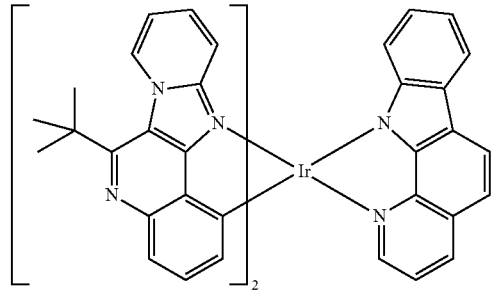 260° C./60 h/DCM THF Ir(L1)₂(CL3) | 41% |

| Ex. | Ligand L | Co-ligand CL | Ir complex Step 1: reaction temp./reaction time/suspension medium Step 2: extractant | Yield |
|---|---|---|---|---|
| 14 | L2 | CL1 | 260° C./40 h/DCM<br>THF<br>Ir(L2)₂(CL1) | 27% |

Variant B:
Step 1:
See Variant A, Step 1.
Step 2:

The crude chloro-bridged dimer of the formula [Ir(L)₂Cl]₂ obtained in this way is suspended in 1000 ml of dichloromethane and 150 ml of ethanol, 40 mmol of silver(I) trifluoromethanesulfonate are added to the suspension, and the mixture is stirred at room temperature for 24 h. The precipitated solid (AgCl) is filtered off with suction via a short Celite bed, and the filtrate is evaporated to dryness in vacuo. The solid obtained in this way is taken up in 100 ml of ethanol, 30 mmol of co-ligand CL are added, and the mixture is then heated under reflux for 30 h. After cooling, the solid is filtered off with suction, washed twice with 50 ml of ethanol each time and dried in vacuo. The solid obtained in this way is placed in a hot extractor on an aluminium oxide bed (aluminium oxide, basic, activity grade 1) with a depth of 10 cm and then extracted with the extractant indicated (amount about 500 ml). When the extraction is complete, the extractant is concentrated to about 100 ml in vacuo. Metal complexes which have excessively good solubility in the extractant are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated; when a purity of 99.5-99.9% has been reached, the metal complex is heated or sublimed. The heating is carried out in a high vacuum (p about $10^{-6}$ mbar) in the temperature range 200-300° C. The sublimation is carried out in a high vacuum (p about $10^{-6}$ mbar) in the temperature range from about 300 to about 390° C., with the sublimation preferably being carried out in the form of a fractional sublimation.

| Ex. | Ligand L | Co-ligand CL | Ir complex Step 1: reaction temp./reaction time/suspension medium Step 2: extractant | Yield |
|---|---|---|---|---|
| 15 | L1 | 1008-89-5<br>CL4 | 260° C./60 h/DCM<br>THF<br>Ir(L1)₂(CL4) | 34% |

-continued

| Ex. | Ligand L | Co-ligand CL | Ir complex Step 1: reaction temp./reaction time/suspension medium Step 2: extractant | Yield |
|---|---|---|---|---|
| 16 | L1 | 53911-36-7 CL5 | 260° C./60 h/DCM THF Ir(L1)₂(CL5) | 26% |
| 17 | L1 | 457932-45-5 CL6 | 260° C./60 h/DCM THF Ir(L1)₂(CL6) | 30% |
| 18 | L1 | 230-27-3 CL7 | 260° C./60 h/DCM THF Ir(L1)₂(CL7) | 21% |

| Ex. | Ligand L | Co-ligand CL | Ir complex Step 1: reaction temp./reaction time/suspension medium Step 2: extractant | Yield |
|---|---|---|---|---|
| 19 | L1 | 536753-86-3 CL8 | 260° C./60 h/DCM THF Ir(L1)$_2$(CL8) | 17% |
| 20 | L2 | 38210-35-4 CL9 | 260° C./40 h/DCM THF Ir(L2)$_2$(CL9) | 35% |
| 21 | L2 | 883-93-2 CL10 | 260° C./40 h/DCM THF Ir(L2)$_2$(CL10) | 33% |

3) Heteroleptic Platinum Complexes

A mixture of 10 mmol of platinum(II) chloride, 12 mmol of ligand L and 1 mmol of tetra-n-butylammonium chloride in 30 ml of dichloromethane is heated under reflux for 12 h. After dropwise addition of 100 ml of methanol, the fine solid is filtered off with suction, washed twice with 25 ml of methanol each time and dried in vacuo. The crude chloro-bridged dimer of the formula [Pt(L)Cl]$_2$ obtained in this way is suspended in a mixture of 60 ml of 2-ethoxyethanol and 20 ml of water, and 12 mmol of co-ligand CL or co-ligand compound CL and 12 mmol of sodium carbonate are added. After 20 h under reflux, a further 100 ml of water are added dropwise, the mixture is cooled, the solid is filtered off with suction, washed three times with 50 ml of water each time and three times with 50 ml of methanol each time and dried in vacuo. The solid obtained in this way is placed in a hot extractor on a Celite bed with a depth of 10 cm and extracted with the extractant indicated (amount about 500 ml). When the extraction is complete, the extractant is concentrated to about 100 ml in vacuo. Metal complexes which have excessively good solubility in the extractant are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated; when a purity of 99.5-99.9% has been reached, the metal complex is heated or sublimed. The heating is carried out in a high vacuum (p about $10^{-6}$ mbar) in the temperature range 200-300° C. The sublimation is carried out in a high vacuum (p about $10^{-6}$ mbar) in the temperature range from about 300 to about 390° C., with the sublimation preferably being carried out in the form of a fractional sublimation.

4) Platinum Complexes of Tetradentate Ligands

Variant A:

A mixture of 10 mmol of potassium tetrachloroplatinate, 10 mmol of ligand L, 50 mmol of lithium acetate, anhydrous, in 100 ml of glacial acetic acid is heated under reflux for 60 h. After dropwise addition of 100 ml of methanol and 100 ml of water to the cooled reaction mixture, the solid is filtered off with suction, washed five times with 25 ml of methanol each time and dried in vacuo. The solid obtained in this way is placed on a Celite bed with a depth of 3 cm in a hot extractor and then extracted with the extractant indicated (amount about 300 ml). When the extraction is complete, the extractant is evaporated to about 100 ml in vacuo. Metal complexes which have excessively good solubility in the extractant are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is less than 99.5%, the hot-extraction step is repeated; when a purity of 99.5-99.9% has been reached, the Pt complex is sublimed. The sublimation is carried out in a high vacuum (p about $10^{-6}$ mbar) in the temperature range from about 350 to about 420° C., where the sublimation is preferably carried out in the form of a fractional sublimation.

| Ex. | Ligand L | Co-ligand CL | Pt complex Extractant | Yield |
|---|---|---|---|---|
| 22 | L1 | CL2 | 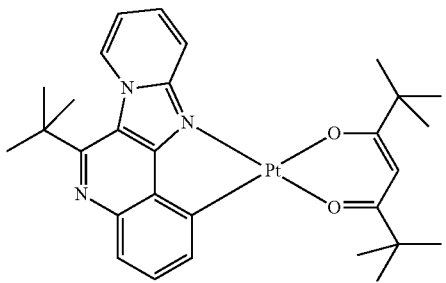 THF Pt(L1)$_2$(CL2) | 25% |
| 23 | L2 | CL2 | 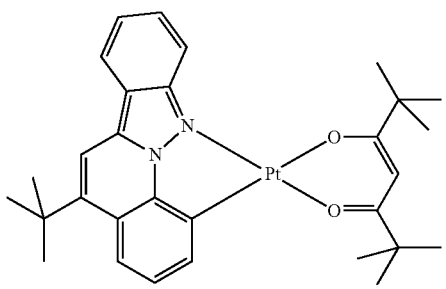 THF Pt(L2)$_2$(CL2) | 21% |

Variant B:

A mixture of 10 mmol of platinum(II) chloride and 10 mmol of ligand L in 50 ml of benzonitrile is heated under reflux for 24 h. After dropwise addition of 100 ml of methanol to the cooled reaction mixture, the solid is filtered off with suction, washed five times with 25 ml of methanol each time and dried in vacuo. Remainder of the work-up as described in the case of variant A.

| Ex. | Ligand L | Pt complex | Variant Extractant | Yield |
|---|---|---|---|---|
| 134 | L61 | Pt(L61) | A p-Xylene | 33% |
| 135 | L61 | Pt(L61) | B p-Xylene | 41% |
| 136 | L62 | Pt(L62) | B p-Xylene | 38% |
| 137 | L86 | Pt(L86) | A p-Xylene | 36% |
| 138 | L87 | Pt(L87) | A p-Xylene | 33% |

-continued

| Ex. | Ligand L | Pt complex | Variant Extractant | Yield |
|---|---|---|---|---|
| 139 | L88 | 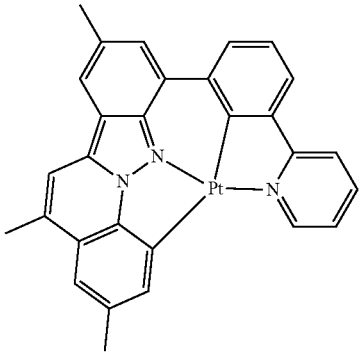<br>Pt(L88) | A<br>p-Xylene | 38% |
| 140 | L89 | 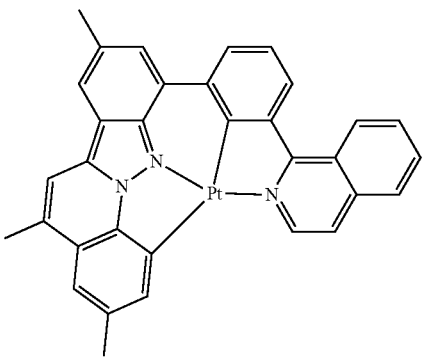<br>Pt(L89) | A<br>p-Xylene | 27% |
| 141 | L100 | 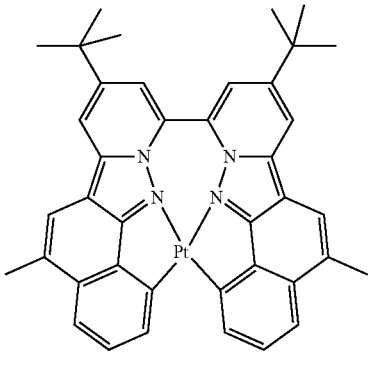<br>Pt(L100) | A<br>p-Xylene | 33% |

Example 24

Production of OLEDs

OLEDs according to the invention and OLEDs in accordance with the prior art are produced by a general process in accordance with WO 2004/058911, which is adapted to the circumstances described here (layer-thickness variation, materials used).

The results for various OLEDs are presented in Examples 25 to 42 below (see Tables 1 and 2). Glass plates coated with structured ITO (indium tin oxide) in a thickness of 150 nm are coated with 20 nm of PEDOT (poly(3,4-ethylenedioxy-2,5-thiophene), applied by spin coating from water; purchased from H. C. Starck, Goslar, Germany) for improved processing. These coated glass plates form the substrates to which the OLEDs are applied. The OLEDs have basically the following layer structure: substrate/optional hole-injection layer (NIL)/hole-transport layer (HTL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm.

Firstly, vacuum-processed OLEDs are described. For this purpose, all materials are applied by thermal vapour deposition in a vacuum chamber. The emission layer here always consists of at least one matrix material (host material) and an emitting dopant (emitter), which is admixed with the matrix material or matrix materials in a certain proportion by volume by coevaporation. An expression such as M3:M2:Ir(L1)$_3$ (55%:35%:10%) here means that material M3 is present in the layer in a proportion by volume of 55%, M2 is present in the layer in a proportion of 35% and Ir(L1)$_3$ is present in the layer in a proportion of 10%. Analogously, the electron-transport layer may also consist of a mixture of two materials. The precise structure of the OLEDs is shown in Table 1. The materials used for the production of the OLEDs are shown in Table 3.

The OLEDs are characterised by standard methods. For this purpose, the electroluminescence spectra, the current efficiency (measured in cd/A) and the voltage (measured at 1000 cd/m$^2$ in V) are determined from current/voltage/luminance characteristic lines (IUL characteristic lines). For selected experiments, the lifetime was determined. The lifetime is defined as the time after which the luminous density has dropped to a certain proportion from a certain initial luminous density. The expression LD50 means that the lifetime given is the time at which the luminous density has dropped to 50% of the initial luminous density, i.e. from, for example, 4000 cd/m$^2$ to 2000 cd/m$^2$. Depending on the emission colour, different initial luminances were selected. The values for the lifetime can be converted to a figure for other initial luminous densities with the aid of conversion formulae known to the person skilled in the art. The lifetime for an initial luminous density of 1000 cd/m$^2$ is a usual figure here.

Use of Compounds According to the Invention as Emitter Materials in Phosphorescent OLEDS The compounds according to the invention can be employed, inter alia, as phosphorescent emitter materials in the emission layer in OLEDs. The metal complexes having the central atoms Ir and Pt are employed here. The compound Ir-ref is used as comparison in accordance with the prior art. The results for the OLEDs are summarised in Table 2. In the case of the processed OLEDs, it is evident here that the materials according to the invention result in efficient yellow- to red-emitting OLEDs. In particular, the lifetime improves significantly compared with the reference emitter (Ex. 43).

TABLE 1

Structure of the OLEDs

| Ex. | HTL1 Thickness | HTL2 Thickness | EML Thickness | HBL Thickness | ETL Thickness | EIL Thickness |
|---|---|---|---|---|---|---|
| 25 | HIM 20 nm | HTM 20 nm | M1:Ir(L1)$_3$ (90%:10%) 30 nm | M1 10 nm | ETM1 35 nm | LiQ 2 nm |
| 26 | HIM 20 nm | HTM 20 nm | M1:Ir(L2)$_3$ (90%:10%) 30 nm | M1 10 nm | ETM1 35 nm | LiQ 2 nm |
| 27 | HIM 20 nm | HTM 20 nm | M1:Ir(L3)$_3$ (90%:10%) 30 nm | M1 10 nm | ETM1 35 nm | LiQ 2 nm |
| 28 | HIM 20 nm | HTM 20 nm | M1:Ir(L4)$_3$ (90%:10%) 30 nm | M1 10 nm | ETM1 35 nm | LiQ 2 nm |
| 29 | HIM 20 nm | HTM 20 nm | M1:Ir(L5)$_3$ (90%:10%) 30 nm | M1 10 nm | ETM1 35 nm | LiQ 2 nm |
| 30 | HIM 20 nm | HTM 20 nm | M1:Ir(L1)$_2$(CL1) (90%:10%) 30 nm | M1 10 nm | ETM1 35 nm | LiQ 2 nm |
| 31 | HIM 20 nm | HTM 20 nm | M1:Ir(L1)$_2$(CL2) (90%:10%) 30 nm | M1 10 nm | ETM1 35 nm | LiQ 2 nm |
| 32 | HIM 20 nm | HTM 20 nm | M1:Ir(L1)$_2$(CL3) (90%:10%) 30 nm | M1 10 nm | ETM1 35 nm | LiQ 2 nm |

TABLE 1-continued

Structure of the OLEDs

| Ex. | HTL1 Thickness | HTL2 Thickness | EML Thickness | HBL Thickness | ETL Thickness | EIL Thickness |
|---|---|---|---|---|---|---|
| 33 | HIM 20 nm | HTM 20 nm | M1:Ir(L2)$_2$(CL1) (90%:10%) 30 nm | M1 10 nm | ETM1 35 nm | LiQ 2 nm |
| 34 | HIM 20 nm | HTM 20 nm | M1:Ir(L1)$_2$(CL4) (90%:10%) 30 nm | M1 10 nm | ETM1 35 nm | LiQ 2 nm |
| 35 | HIM 20 nm | HTM 20 nm | M1:Ir(L1)$_2$(CL5) (90%:10%) 30 nm | M1 10 nm | ETM1 35 nm | LiQ 2 nm |
| 36 | HIM 20 nm | HTM 20 nm | M1:Ir(L1)$_2$(CL6) (90%:10%) 30 nm | M1 10 nm | ETM1 35 nm | LiQ 2 nm |
| 37 | HIM 20 nm | HTM 20 nm | M1:Ir(L1)$_2$(CL7) (90%:10%) 30 nm | M1 10 nm | ETM1 35 nm | LiQ 2 nm |
| 38 | HIM 20 nm | HTM 20 nm | M1:Ir(L1)$_2$(CL8) (90%:10%) 30 nm | M1 10 nm | ETM1 35 nm | LiQ 2 nm |
| 39 | HIM 20 nm | HTM 20 nm | M1:Ir(L2)$_2$(CL9) (90%:10%) 30 nm | M1 10 nm | ETM1 35 nm | LiQ 2 nm |
| 40 | HIM 20 nm | HTM 20 nm | M1:Ir(L2)$_2$(CL10) (90%:10%) 30 nm | M1 10 nm | ETM1 35 nm | LiQ 2 nm |
| 41 | HIM 20 nm | HTM 20 nm | M1:Pt(L1)(CL2) (90%:10%) 30 nm | M1 10 nm | ETM1 35 nm | LiQ 2 nm |
| 42 | HIM 20 nm | HTM 20 nm | M1:Ir(L2)(CL1) (90%:10%) 30 nm | M1 10 nm | ETM1 35 nm | LiQ 2 nm |
| 43 (cmp.) | HIM 20 nm | HTM 20 nm | M1:Ir-ref (90%:10%) 30 nm | M1 10 nm | ETM1 35 nm | LiQ 2 nm |
| 44 (cmp.) | HIM 20 nm | HTM 20 nm | M1:Ir-ref (80%:20%) 30 nm | M1 10 nm | ETM1 35 nm | LiQ 2 nm |
| 45 (cmp.) | HIM 20 nm | HTM 20 nm | M1:Ir-ref (90%:10%) 30 nm | M1 5 nm | ETM1 35 nm | LiQ 2 nm |
| 142 | HIM 20 nm | HTM 20 nm | M1:Ir(L46)$_3$ (90%:10%) 30 nm | M1 10 nm | ETM1 35 nm | LiQ 2 nm |
| 143 | HIM 20 nm | HTM 20 nm | M1:Ir(L47)$_3$ (90%:10%) 30 nm | M1 10 nm | ETM1 35 nm | LiQ 2 nm |
| 144 | HIM 20 nm | HTM 20 nm | M1:Ir(L48)$_3$ (90%:10%) 30 nm | M1 10 nm | ETM1 35 nm | LiQ 2 nm |
| 145 | HIM 20 nm | HTM 20 nm | M1:Ir(L49)$_3$ (90%:10%) 30 nm | M1 10 nm | ETM1 35 nm | LiQ 2 nm |
| 146 | HIM 20 nm | HTM 20 nm | M1:Ir(L50)$_3$ (90%:10%) 30 nm | M1 10 nm | ETM1 35 nm | LiQ 2 nm |
| 146 | HIM 20 nm | HTM 20 nm | M1:Ir(L51)$_3$ (90%:10%) 30 nm | M1 10 nm | ETM1 35 nm | LiQ 2 nm |
| 148 | HIM 20 nm | HTM 20 nm | M1:Ir(L52)$_3$ (90%:10%) 30 nm | M1 10 nm | ETM1 35 nm | LiQ 2 nm |
| 149 | HIM 20 nm | HTM 20 nm | M1:Ir(L53)$_3$ (90%:10%) 30 nm | M1 10 nm | ETM1 35 nm | LiQ 2 nm |
| 150 | HIM 20 nm | HTM 20 nm | M1:Ir(L54)$_3$ (90%:10%) 30 nm | M1 10 nm | ETM1 35 nm | LiQ 2 nm |
| 151 | HIM 20 nm | HTM 20 nm | M1:Ir(L55)$_3$ (90%:10%) 30 nm | M1 10 nm | ETM1 35 nm | LiQ 2 nm |
| 152 | HIM 20 nm | HTM 20 nm | M1:Ir(L56)$_3$ (90%:10%) 30 nm | M1 10 nm | ETM1 35 nm | LiQ 2 nm |

TABLE 1-continued

Structure of the OLEDs

| Ex. | HTL1 Thickness | HTL2 Thickness | EML Thickness | HBL Thickness | ETL Thickness | EIL Thickness |
|---|---|---|---|---|---|---|
| 153 | HIM 20 nm | HTM 20 nm | M1:Ir(L57)$_3$ (90%:10%) 30 nm | M1 10 nm | ETM1 35 nm | LiQ 2 nm |
| 154 | HIM 20 nm | HTM 20 nm | M1:Ir(L58)$_3$ (90%:10%) 30 nm | M1 10 nm | ETM1 35 nm | LiQ 2 nm |
| 155 | HIM 20 nm | HTM 20 nm | M1:Ir(L59)$_3$ (90%:10%) 30 nm | M1 10 nm | ETM1 35 nm | LiQ 2 nm |
| 156 | HIM 20 nm | HTM 20 nm | M1:Ir(L60)$_3$ (90%:10%) 30 nm | M1 10 nm | ETM1 35 nm | LiQ 2 nm |
| 157 | HIM 20 nm | HTM 20 nm | M1:Ir(L63)$_3$ (90%:10%) 30 nm | M1 10 nm | ETM1 35 nm | LiQ 2 nm |
| 158 | HIM 20 nm | HTM 20 nm | M1:Ir(L75)$_3$ (90%:10%) 30 nm | M1 10 nm | ETM1 35 nm | LiQ 2 nm |
| 159 | HIM 20 nm | HTM 20 nm | M1:Ir(L76)$_3$ (90%:10%) 30 nm | M1 10 nm | ETM1 35 nm | LiQ 2 nm |
| 160 | HIM 20 nm | HTM 20 nm | M1:Ir(L47)$_3$ (90%:10%) 30 nm | M1 10 nm | ETM1 35 nm | LiQ 2 nm |
| 161 | HIM 20 nm | HTM 20 nm | M1:Ir(L77)$_3$ (90%:10%) 30 nm | M1 10 nm | ETM1 35 nm | LiQ 2 nm |
| 162 | HIM 20 nm | HTM 20 nm | M1:Ir(L78)$_3$ (90%:10%) 30 nm | M1 10 nm | ETM1 35 nm | LiQ 2 nm |
| 162 | HIM 20 nm | HTM 20 nm | M1:Ir(L79)$_3$ (90%:10%) 30 nm | M1 10 nm | ETM1 35 nm | LiQ 2 nm |
| 164 | HIM 20 nm | HTM 20 nm | M1:Ir(L80)$_3$ (90%:10%) 30 nm | M1 10 nm | ETM1 35 nm | LiQ 2 nm |
| 165 | HIM 20 nm | HTM 20 nm | M1:Ir(L81)$_3$ (90%:10%) 30 nm | M1 10 nm | ETM1 35 nm | LiQ 2 nm |
| 166 | HIM 20 nm | HTM 20 nm | M1:Ir(L82)$_3$ (90%:10%) 30 nm | M1 10 nm | ETM1 35 nm | LiQ 2 nm |
| 167 | HIM 20 nm | HTM 20 nm | M1:Ir(L83)$_3$ (90%:10%) 30 nm | M1 10 nm | ETM1 35 nm | LiQ 2 nm |
| 168 | HIM 20 nm | HTM 20 nm | M1:Ir(L84)$_3$ (90%:10%) 30 nm | M1 10 nm | ETM1 35 nm | LiQ 2 nm |
| 169 | HIM 20 nm | HTM 20 nm | M1:Ir(L85)$_3$ (90%:10%) 30 nm | M1 10 nm | ETM1 35 nm | LiQ 2 nm |
| 170 | HIM 20 nm | HTM 20 nm | M1:Ir(L90)$_3$ (90%:10%) 30 nm | M1 10 nm | ETM1 35 nm | LiQ 2 nm |
| 171 | HIM 20 nm | HTM 20 nm | M1:Ir(96)$_3$ (90%:10%) 30 nm | M1 10 nm | ETM1 35 nm | LiQ 2 nm |
| 172 | HIM 20 nm | HTM 20 nm | M1:Ir(L97)$_3$ (90%:10%) 30 nm | M1 10 nm | ETM1 35 nm | LiQ 2 nm |
| 173 | HIM 20 nm | HTM 20 nm | M1:Ir(L98)$_3$ (90%:10%) 30 nm | M1 10 nm | ETM1 35 nm | LiQ 2 nm |
| 174 | HIM 20 nm | HTM 20 nm | M1:Ir(L99)$_3$ (90%:10%) 30 nm | M1 10 nm | ETM1 35 nm | LiQ 2 nm |
| 175 | HIM 20 nm | HTM 20 nm | M1:Pt(L61) (90%:10%) 30 nm | M1 10 nm | ETM1 35 nm | LiQ 2 nm |
| 176 | HIM 20 nm | HTM 20 nm | M1:Pt(L62) (90%:10%) 30 nm | M1 10 nm | ETM1 35 nm | LiQ 2 nm |
| 177 | HIM 20 nm | HTM 20 nm | M1:Pt(L86) (90%:10%) 30 nm | M1 10 nm | ETM1 35 nm | LiQ 2 nm |
| 178 | HIM 20 nm | HTM 20 nm | M1:Pt(L87) (90%:10%) 30 nm | M1 10 nm | ETM1 35 nm | LiQ 2 nm |
| 179 | HIM 20 nm | HTM 20 nm | M1:Pt(L88) (90%:10%) 30 nm | M1 10 nm | ETM1 35 nm | LiQ 2 nm |
| 180 | HIM 20 nm | HTM 20 nm | M1:Pt(L89) (90%:10%) 30 nm | M1 10 nm | ETM1 35 nm | LiQ 2 nm |
| 181 | HIM 20 nm | HTM 20 nm | M1:Pt(L100) (90%:10%) 30 nm | M1 10 nm | ETM1 35 nm | LiQ 2 nm |

TABLE 2

Use of compounds according to the invention as emitter materials in phosphorescent OLEDs

| Ex. | Efficiency (cd/A) at 1000 cd/m$^2$ | Voltage (V) at 1000 cd/m$^2$ | CIE x/y at 1000 cd/m$^2$ | LT50 (h) at 1000 cd/m$^2$ |
|---|---|---|---|---|
| 25 | 28.2 | 4.2 | 0.49/0.48 | 18000 |
| 26 | 30.4 | 4.6 | 0.50/0.47 | 26000 |
| 27 | 27.7 | 4.8 | 0.49/0.48 | 12000 |
| 28 | 25.5 | 4.5 | 0.52/0.46 | 20000 |
| 29 | 25.1 | 4.7 | 0.54/0.44 | 29000 |
| 30 | 34.9 | 4.5 | 0.50/0.48 | 37000 |
| 31 | 31.1 | 4.4 | 0.51/0.46 | 35000 |
| 32 | 27.6 | 4.6 | 0.62/0.38 | 37000 |
| 33 | 22.3 | 4.8 | 0.49/0.47 | 11000 |
| 34 | 29.9 | 5.2 | 0.48/0.49 | 20000 |
| 35 | 35.2 | 5.0 | 0.49/0.48 | 29000 |
| 36 | 22.4 | 4.4 | 0.51/0.46 | 31000 |
| 37 | 25.1 | 4.5 | 0.60/0.39 | 25000 |
| 38 | 23.7 | 5.0 | 0.63/0.37 | 27000 |
| 39 | 19.8 | 5.2 | 0.63/0.37 | 31000 |
| 40 | 35.4 | 4.3 | 0.48/0.49 | 28000 |
| 41 | 22.2 | 6.1 | 0.50/0.47 | 24000 |
| 42 | 23.6 | 5.5 | 0.49/0.48 | 21000 |
| 43 (cmp.) | 20.9 | 4.6 | 0.62/0.38 | 4100 |

TABLE 3

Use of compounds according to the invention as emitter materials in phosphorescent OLEDs

| Ex. | EQE [%] at 1000 cd/m$^2$ | Voltage (V) at 1000 cd/m$^2$ | CIE x/y at 1000 cd/m$^2$ | LT50 (h) at 1000 cd/m$^2$ |
|---|---|---|---|---|
| 142 | 12.5 | 4.0 | 0.49/0.48 | 26000 |
| 143 | 13.8 | 4.1 | 0.49/0.48 | 35000 |
| 144 | 13.4 | 4.2 | 0.49/0.48 | 31000 |
| 145 | 14.3 | 3.9 | 0.49/0.48 | 30000 |
| 146 | 14.6 | 4.0 | 0.49/0.48 | 31000 |
| 146 | 13.9 | 4.1 | 0.47/0.51 | 26000 |
| 148 | 14.0 | 3.8 | 0.49/0.48 | 34000 |
| 149 | 16.7 | 4.0 | 0.49/0.48 | 36000 |
| 150 | 15.0 | 4.0 | 0.49/0.48 | 33000 |
| 151 | 15.2 | 3.9 | 0.49/0.48 | 40000 |
| 152 | 14.9 | 4.6 | 0.29/0.69 | 24000 |
| 153 | 14.9 | 4.5 | 0.31/0.66 | 25000 |
| 154 | 11.0 | 4.6 | 0.44/0.55 | 22000 |
| 155 | 12.0 | 4.5 | 0.46/0.51 | 26000 |

TABLE 3-continued
Use of compounds according to the invention as emitter materials in phosphorescent OLEDs
| Ex. | EQE [%] at 1000 cd/m$^2$ | Voltage (V) at 1000 cd/m$^2$ | CIE x/y at 1000 cd/m$^2$ | LT50 (h) at 1000 cd/m$^2$ |
|---|---|---|---|---|
| 156 | 13.6 | 4.5 | 0.29/0.69 | 27000 |
| 157 | 14.1 | 4.4 | 0.33/0.63 | 29000 |
| 158 | 14.3 | 4.5 | 0.50/0.49 | 27000 |
| 159 | 14.7 | 4.5 | 0.51/0.48 | 27000 |
| 160 | 14.5 | 4.6 | 0.51/0.48 | 24000 |
| 161 | 15.0 | 4.5 | 0.56/0.42 | 25000 |
| 162 | 15.6 | 4.5 | 0.56/0.42 | 27000 |
| 162 | 14.9 | 4.5 | 0.53/0.46 | 26000 |
| 164 | 13.8 | 4.4 | 0.43/0.56 | 29000 |
| 165 | 15.5 | 4.4 | 0.51/0.48 | 34000 |
| 166 | 14.7 | 4.5 | 0.55/0.44 | 33000 |
| 167 | 14.0 | 4.6 | 0.52/0.47 | 25000 |
| 168 | 10.5 | 5.8 | 0.29/0.66 | 11000 |
| 169 | 10.3 | 5.4 | 0.49/0.50 | 9000 |
| 170 | 12.0 | 3.9 | 0.36/0.63 | 41000 |
| 171 | 12.2 | 3.8 | 0.34/0.65 | 40000 |
| 172 | 13.1 | 3.9 | 0.37/0.62 | 39500 |
| 173 | 14.6 | 3.9 | 0.37/0.62 | 42000 |
| 174 | 15.4 | 4.4 | 0.37/0.62 | 27000 |
| 175 | 11.9 | 4.2 | 0.69/0.31 | 66000 |
| 176 | 12.3 | 4.1 | 0.69/0.31 | 70000 |
| 177 | 11.7 | 4.3 | 0.68/0.30 | 65000 |
| 178 | 4.0 | 4.3 | 0.73/0.27 | — |
| 179 | 13.5 | 4.2 | 0.71/0.28 | 27000 |
| 180 | 4.3 | 4.4 | 0.73/0.27 | — |
| 181 | 12.9 | 4.3 | 0.67/0.30 | 65000 |
TABLE 4
Structural formulae of the materials used
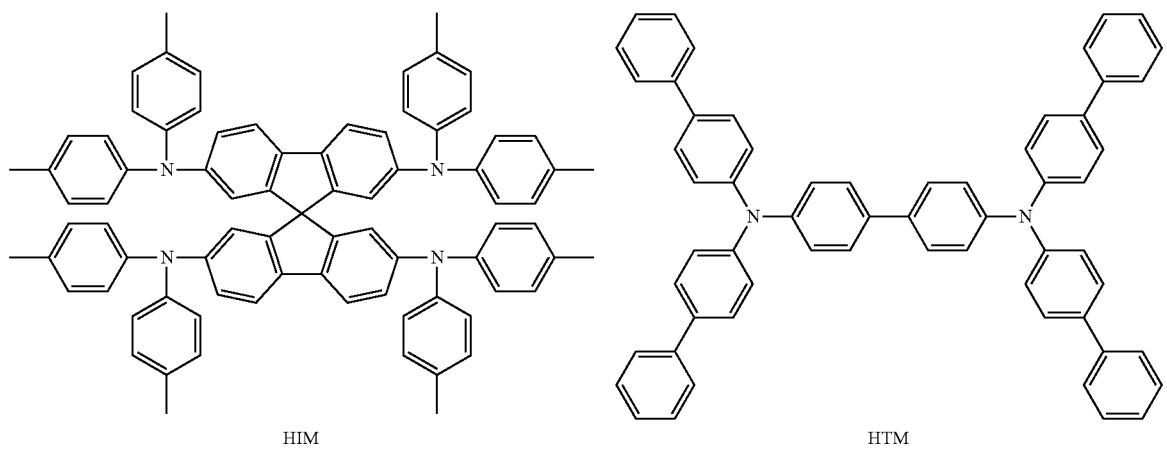
HIM                HTM
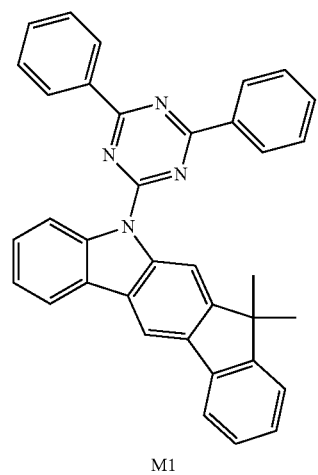
M1
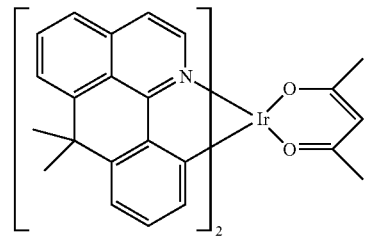
Ir-ref TABLE 4-continued Structural formulae of the materials used

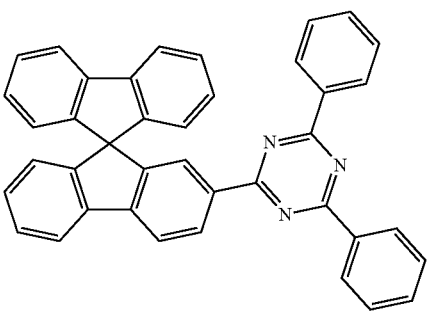 [SMILES: c1ccc(-c2nc(-c3ccccc3)nc(-c3ccc4c(c3)C3(c5ccccc5-c5ccccc53)c3ccccc3-4)n2)cc1]

ETM1

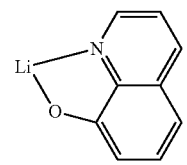

LiQ

Materials according to the invention can also be used from solution, where they result in simpler OLEDs compared with vacuum-processed OLEDs nevertheless having good properties. The production of such components is based on the production of polymeric light-emitting diodes (PLEDs), which has already been described many times in the literature (for example in WO 2004/037887). The structure is composed of substrate/ITO/PEDOT (80 nm)/interlayer/emission layer (80 nm)/cathode. The interlayer used serves for hole injection; in this case, HIL-012 from Merck was used. In the present case, the emitters according to the invention for the emission layer are dissolved in toluene along with the matrices. The typical solids content of such solutions is between 16 and 25 g/l if, as here, the typical layer thickness of 80 nm for a device is to be achieved by means of spin coating. The emission layer is applied by spin coating in an inert-gas atmosphere, in the present case argon, and dried by heating at 120° C. for 10 min. Finally, a cathode comprising barium and aluminium is applied by vacuum vapour deposition. The layers HBL and ETL used in the above-mentioned examples can also be applied between EML and cathode by vapour deposition, and the interlayer can also be replaced by one or more layers, which merely have to satisfy the condition of not being detached again by the subsequent processing step of EML deposition from solution. The solution-processed devices are also characterised by standard methods in the matrices PS (polystyrene):ETM1: Ir(LX)$_3$ (26%:54%:20%). The OLED examples given have not yet been optimised. Table 4 summarises the data obtained. In the case of the processed OLEDs, it is apparent that the materials according to the invention result in efficient yellow- to orange/red-emitting OLEDs.

TABLE 4

Results with materials processed from solution

| Ex. | EML with emitter 80 nm | Voltage [V] at 100 cd/m² | Max. eff. [cd/A] | CIE (x, y) | LT50 (h) at 1000 cd/m² |
|---|---|---|---|---|---|
| 44 | Ir(L5)$_3$ | 5.6 | 18.6 | 0.54/0.44 | 13000 |
| 45 | Ir(L2)$_2$(CL9) | 4.9 | 16.3 | 0.63/0.37 | 16000 |
| 182 | Pt(L62) | 4.7 | 8.0 | 0.69/0.31 | 7000 |
| 183 | Pt(L88) | 4.8 | 6.9 | 0.71/0.28 | 31000 |
| 184 | Pt(L100) | 4.8 | 8.9 | 0.67/0.30 | 30000 |

The invention claimed is:

1. A compound of the formula (1), $$M(L)_n(L')_m \qquad \text{formula (1)}$$

where the compound contains a moiety $M(L)_n$, of the formula (2):

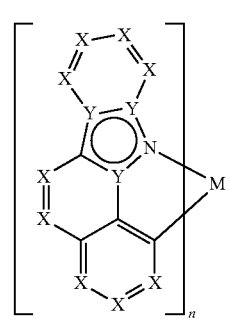

formula (2)

where the following applies to the symbols and indices used:

M is a metal;

Y is on each occurrence, identically or differently, C or N, with the proviso that precisely one symbol Y in each ligand stands for N and the other two symbols Y stand for C;

X is on each occurrence, identically or differently, CR or N;

R is on each occurrence, identically or differently, H, D, F, Cl, Br, I, N(R$^1$)$_2$, CN, NO$_2$, OH, COOH, C(=O)N(R$^1$)$_2$, Si(R$^1$)$_3$, B(OR$^1$)$_2$, C(=O)R$^1$, P(=O)(R$^1$)$_2$, S(=O)R$^1$, S(=O)$_2$R$^1$, OSO$_2$R$^1$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals R$^1$, where one or more non-adjacent CH$_2$ groups is optionally replaced by R$^1$C=CR$^1$, C≡C, Si(R$^1$)$_2$, C=O, NR$^1$, O, S or CONR$^1$ and where one or more H atoms is optionally replaced by D, F, Cl, Br, I or CN, or an aromatic or heteroaromatic ring system having 5 to 60 aromatic ring atoms, which may in each case be substituted by one or more radicals R$^1$, or an aryloxy or heteroaryloxy group having 5 to 40 aromatic ring atoms, which is optionally substituted by one or more radicals R$^1$, or an aralkyl or heteroaralkyl group having 5 to 40 aromatic ring atoms, which is optionally substituted by one or more radicals R$^1$, or a diarylamino group, diheteroarylamino group or arylheteroarylamino group having 10 to 40 aromatic ring atoms, which is optionally substituted by one or more radicals R¹; two adjacent radicals R here may also form a mono- or polycyclic, and/or aliphatic ring system with one another, with the proviso that the two adjacent radicals R do not form a benzo-fused ring system;

R¹ is on each occurrence, identically or differently, H, D, F, Cl, Br, I, N(R²)₂, CN, NO₂, Si(R²)₃, B(OR²)₂, C(=O)R², P(=O)(R²)₂, S(=O)R², S(=O)₂R², OSO₂R², a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals R², where one or more non-adjacent CH₂ groups is optionally replaced by R²C=CR², C≡C, Si(R²)₂, C=O, NR², O, S or CONR² and where one or more H atoms is optionally replaced by D, F, Cl, Br, I, CN, or NO₂, or an aromatic or heteroaromatic ring system having 5 to 60 aromatic ring atoms, which may in each case be substituted by one or more radicals R², or an aryloxy or heteroaryloxy group having 5 to 40 aromatic ring atoms, which is optionally substituted by one or more radicals R², or an aralkyl or heteroaralkyl group having 5 to 40 aromatic ring atoms, which is optionally substituted by one or more radicals R², or a diarylamino group, diheteroarylamino group or arylheteroarylamino group having 10 to 40 aromatic ring atoms, which is optionally substituted by one or more radicals R²; two adjacent radicals R¹ here may also form a mono- or polycyclic, aliphatic, aromatic and/or benzo-fused ring system with one another;

R² is on each occurrence, identically or differently, H, D, F or an aliphatic, aromatic and/or heteroaromatic hydrocarbon radical having 1 to 20 C atoms, in which, in addition, one or more H atoms is optionally replaced by F; two or more substituents R² here may also form a mono- or polycyclic aliphatic ring system with one another;

L' is, identically or differently on each occurrence, a co-ligand;

n is 1, 2 or 3;

m is 0, 1, 2, 3 or 4;

a plurality of ligands L here may also be linked to one another or L is optionally linked to L' via any desired bridge V and thus form a tridentate, tetradentate, pentadentate or hexadentate ligand system and/or a substituent R may additionally be coordinated to the metal;

the following compounds are excluded from the invention:

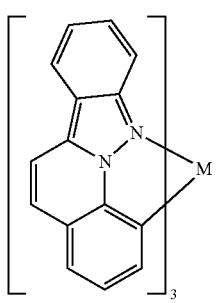
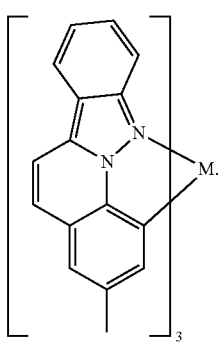

2. The compound according to claim 1, wherein M is selected from the group consisting of chromium, molybdenum, tungsten, rhenium, ruthenium, osmium, rhodium, iridium, nickel, palladium, platinum, copper, silver and gold.

3. The compound according to claim 1, wherein all X in ligand L stand for CR or in that precisely one, two, three or four groups X stand for N and the remaining groups X stand for CR.

4. The compound according to claim 1, wherein the moieties of the formula (2) are selected from the moieties of the formulae (4) to (33),

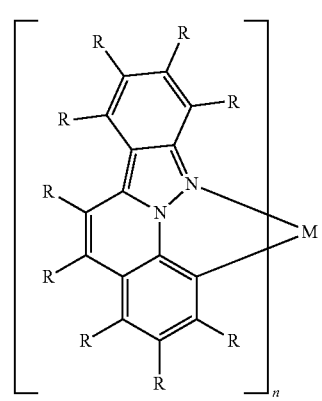

formula (4)

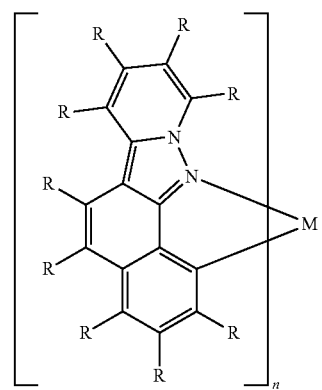

formula (5)

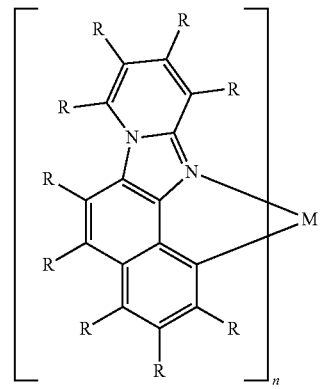

formula (6)

-continued
formula (7)
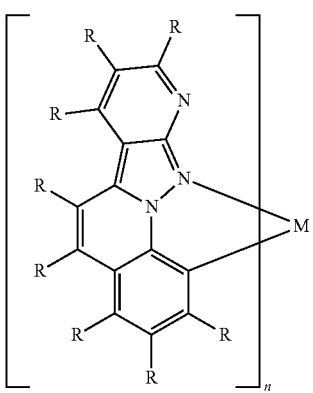
formula (8)
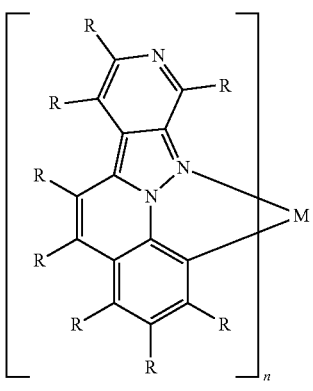
formula (9)
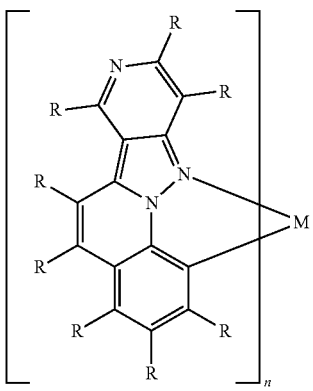
formula (10)
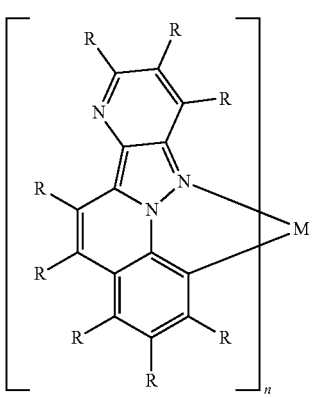
-continued
formula (11)
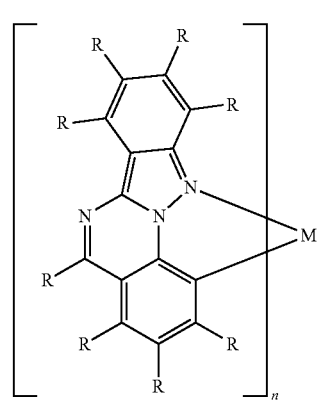
formula (12)
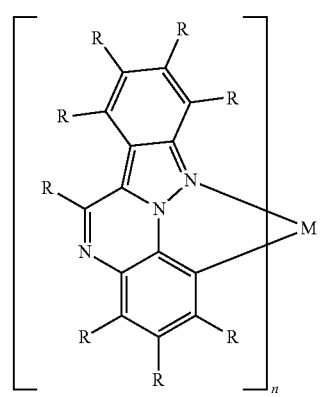
formula (13)
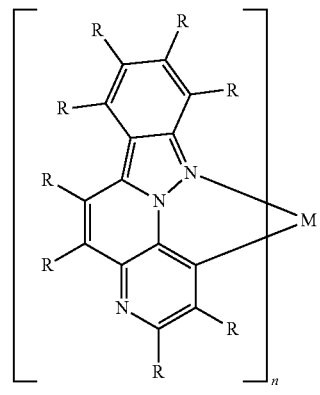
formula (14)
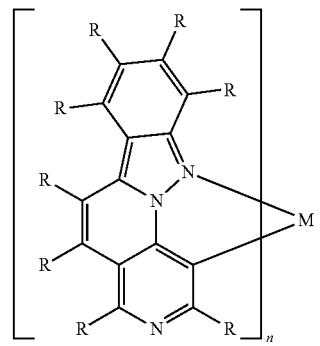

formula (15)
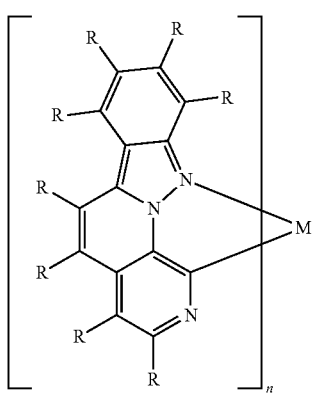
formula (16)
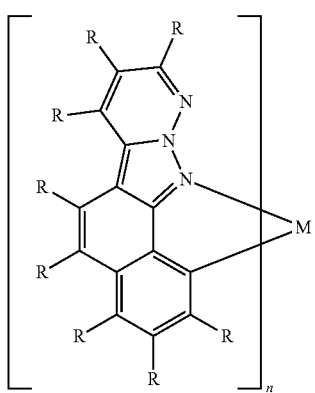
formula (17)
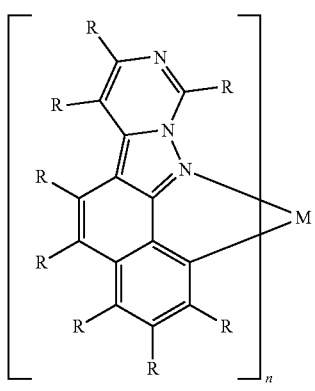
formula (18)
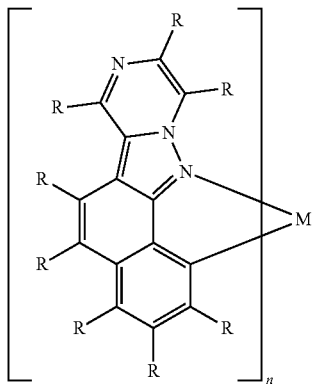
formula (19)
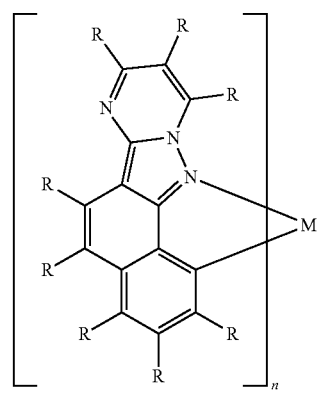
formula (20)
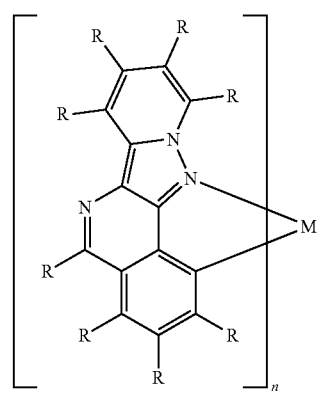
formula (21)
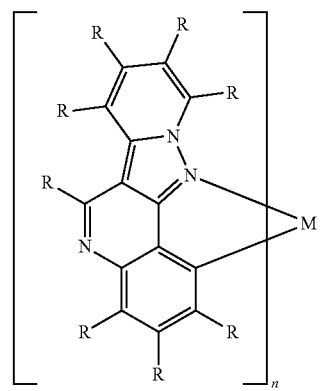
formula (22)
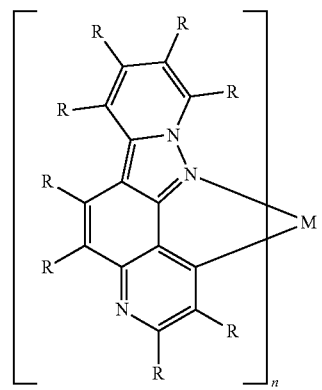

formula (23)
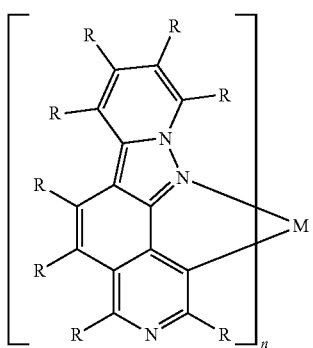
formula (24)
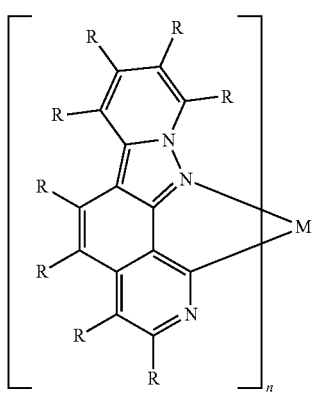
formula (25)
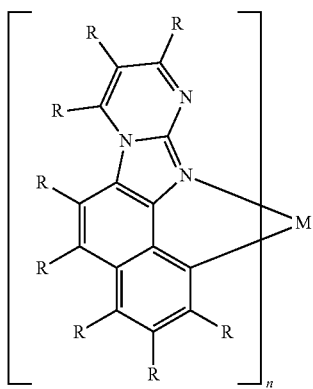
formula (26)
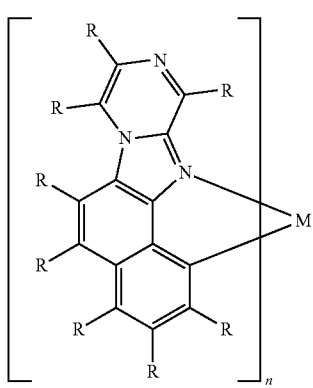
formula (27)
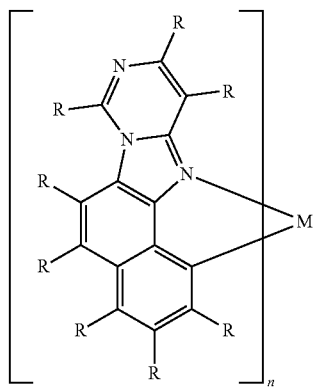
formula (28)
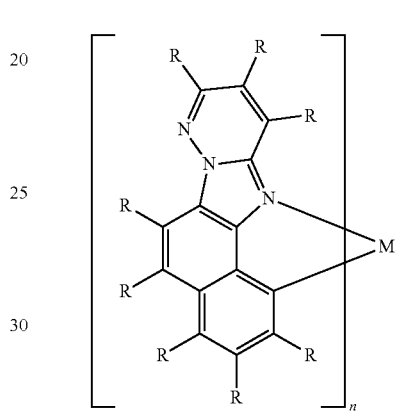
formula (29)
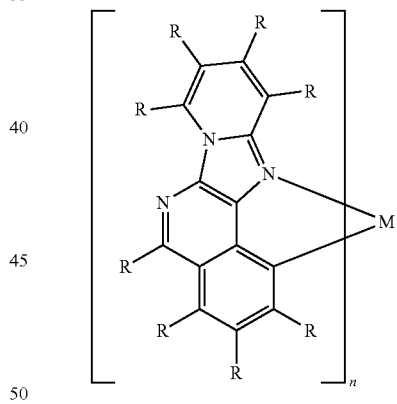
formula (30)
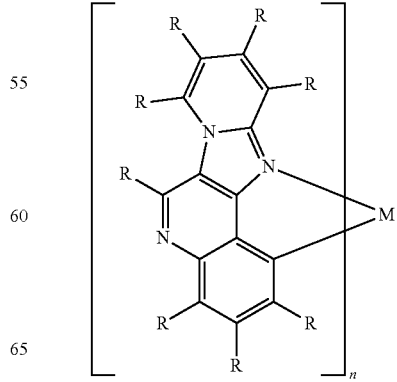

formula (31)

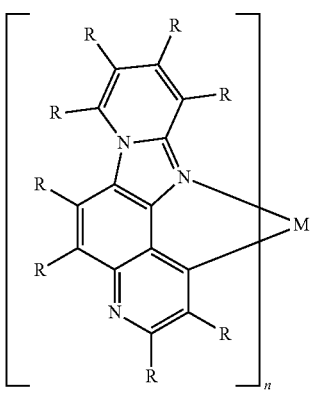

formula (32)

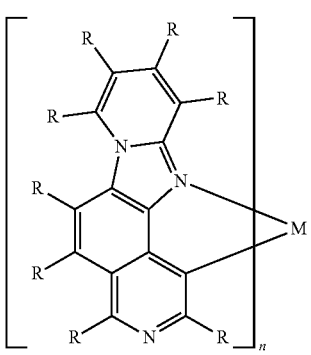

formula (33)

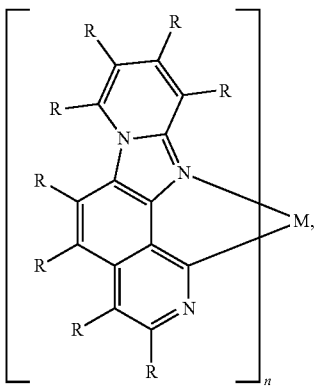

where the symbols and indices used have the meanings given in claim 1.

5. The compound according to claim 1, in which at least one group X=N, wherein at least one group X which is adjacent to this nitrogen atom stands for a $CR^3$ group, where $R^3$ is on each occurrence, identically or differently, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals $R^1$, where one or more non-adjacent $CH_2$ groups is optionally replaced by $R^1C=CR^1$, $Si(R^1)_2$, C=O, $NR^1$, O, S or $CONR^1$ and where one or more H atoms is optionally replaced by D, F, Cl, Br, I or CN, or an aromatic or heteroaromatic ring system having 5 to 60 aromatic ring atoms, which may in each case be substituted by one or more radicals $R^1$, or an aryloxy or heteroaryloxy group having 5 to 40 aromatic ring atoms, which is optionally substituted by one or more radicals $R^1$, or an aralkyl or heteroaralkyl group having 5 to 40 aromatic ring atoms, which is optionally substituted by one or more radicals $R^1$, or a diarylamino group, diheteroarylamino group or arylheteroarylamino group having 10 to 40 aromatic ring atoms, which is optionally substituted by one or more radicals $R^1$; $R^3$ here may also form a mono- or polycyclic, aliphatic, aromatic and/or benzo-fused ring system with an adjacent radical R.

6. The compound according to claim 1, selected from the structures of the formulae (7a) to (33a) and (8b) to (32b), formula (7a)

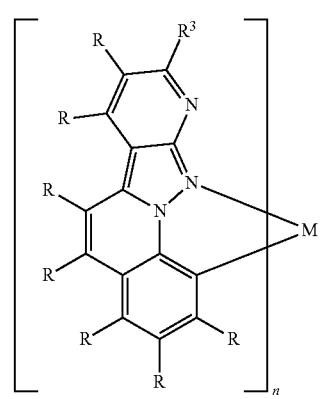

formula (8a)

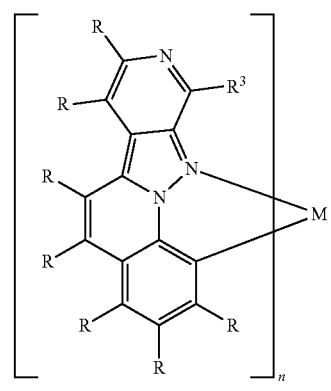

formula (8b)

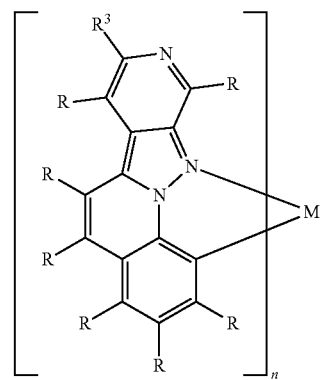

-continued
formula (9a)
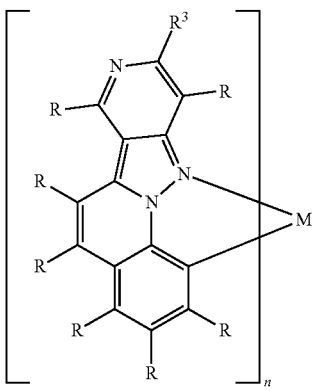
formula (9b)
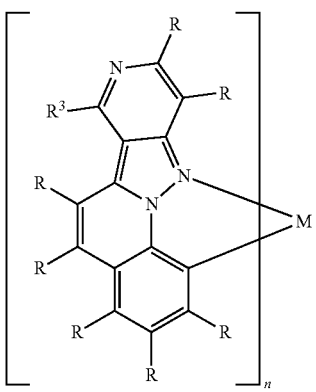
formula (10a)
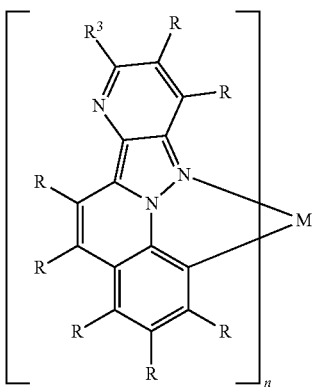
formula (10b)
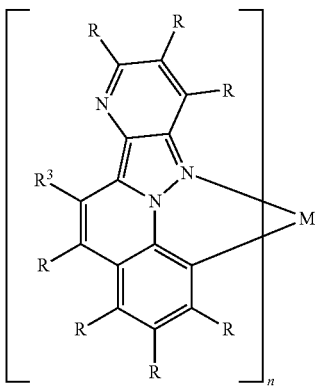
formula (11a)
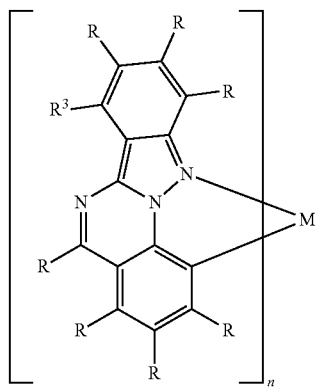
formula (11b)
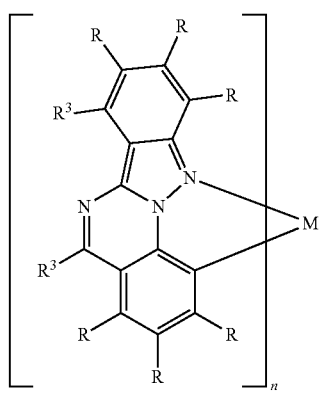
formula (12a)
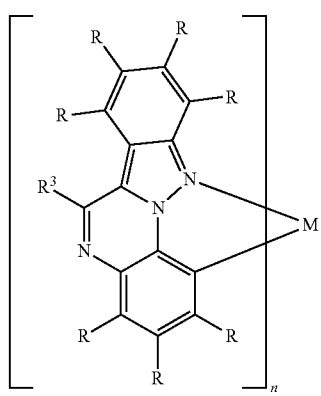
formula (12b)
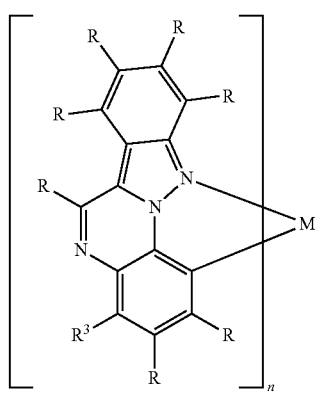

-continued
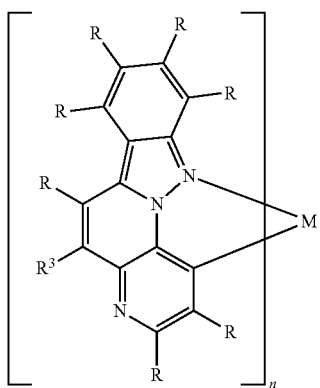
formula (13a)
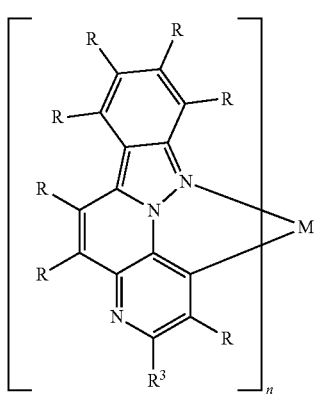
formula (13b)
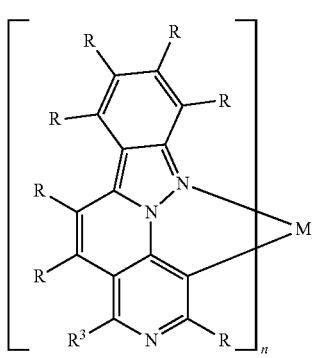
formula (14a)
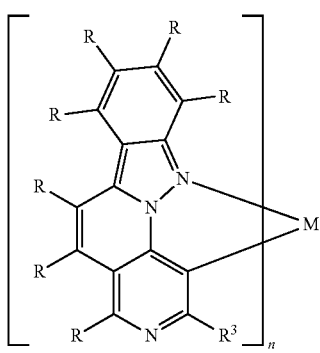
formula (14b)
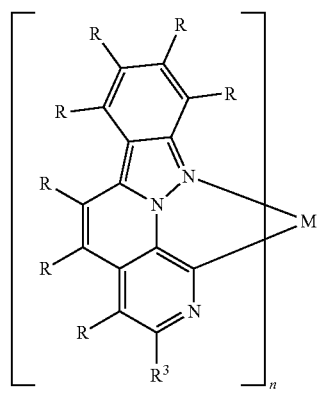
formula (15a)
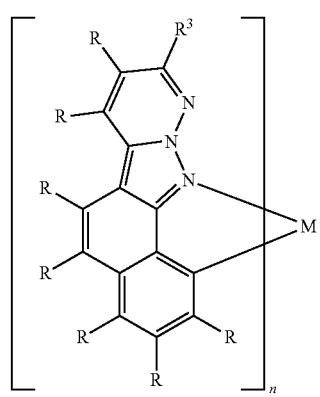
formula (16a)
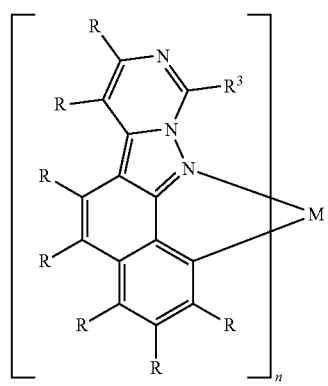
formula (17a)
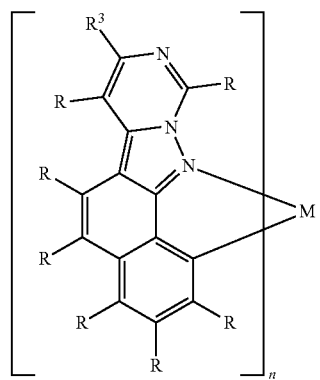
formula (17b)

formula (18a)
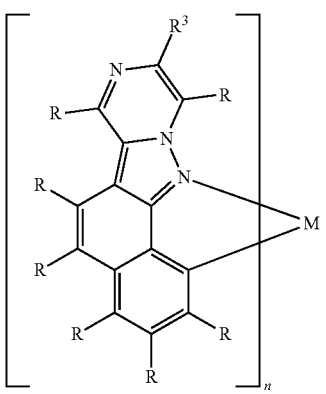
formula (18b)
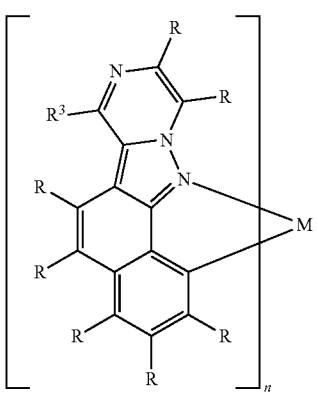
formula (19a)
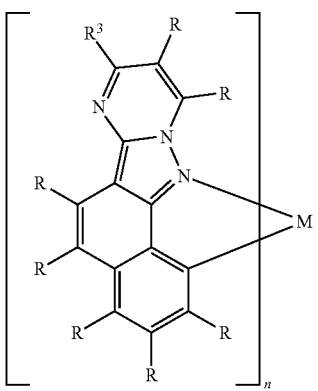
formula (19b)
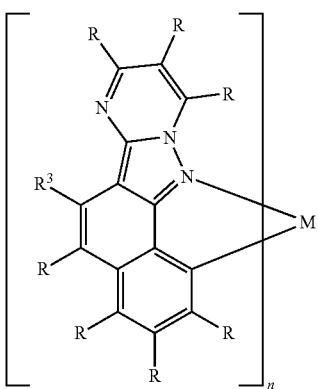
formula (20a)
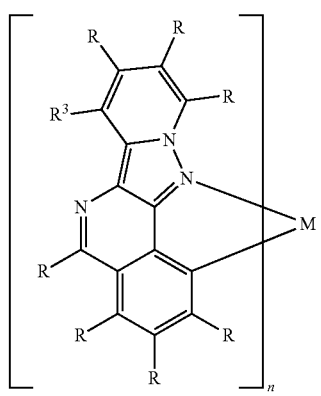
formula (20b)
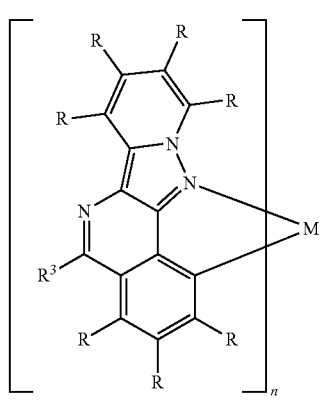
formula (21a)
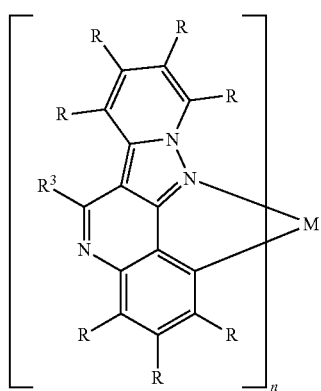
formula (21b)
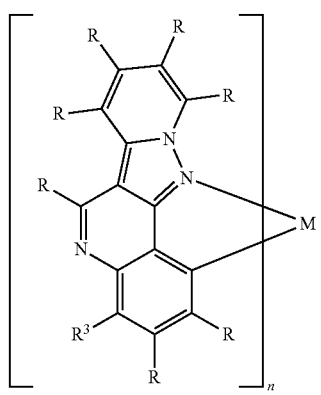

formula (22a)
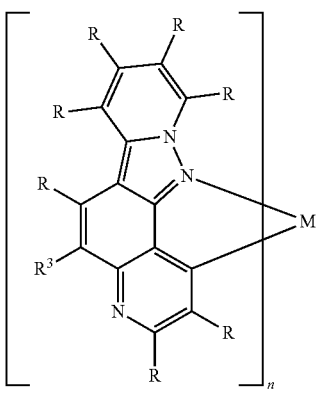
formula (22b)
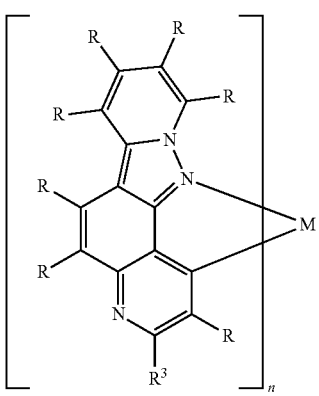
formula (23a)
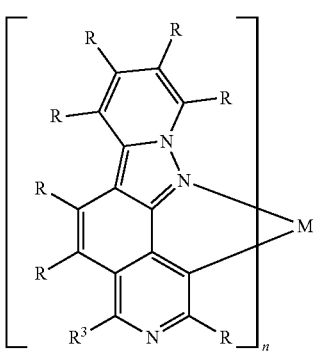
formula (23b)
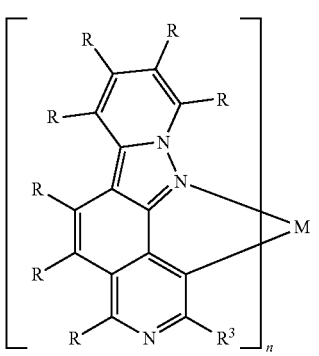
formula (24a)
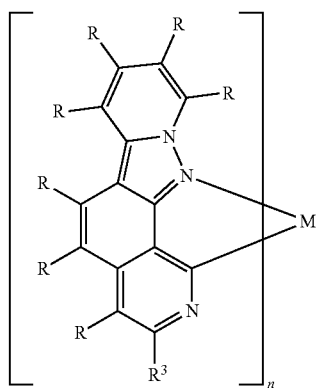
formula (25a)
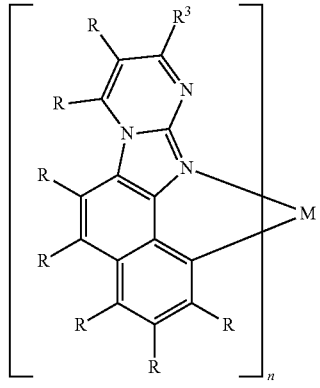
formula (26a)
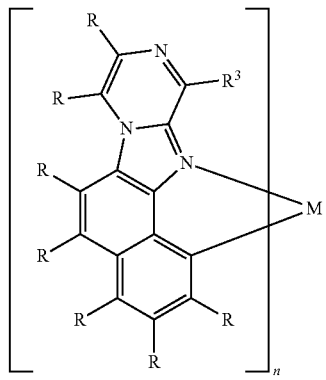
formula (26b)
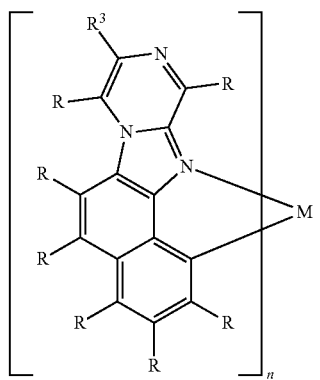

-continued
formula (27a)
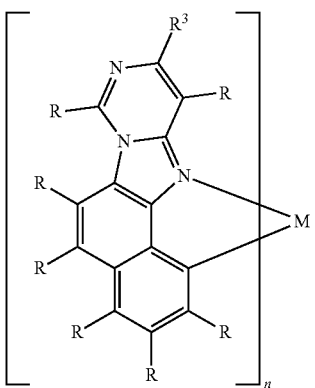
formula (27b)
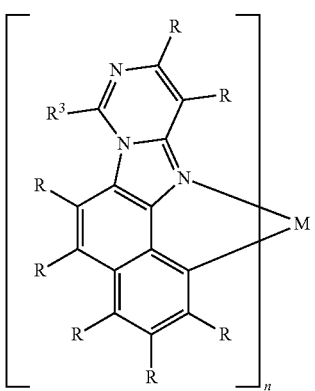
formula (28a)
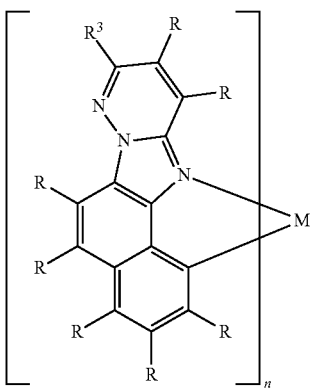
formula (28b)
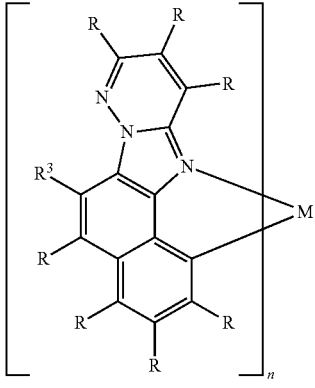
formula (29a)
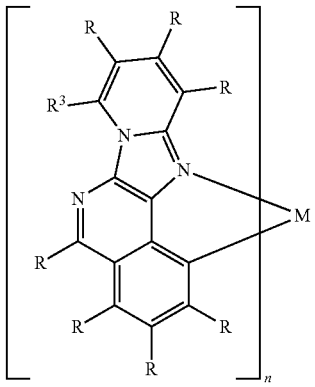
formula (29b)
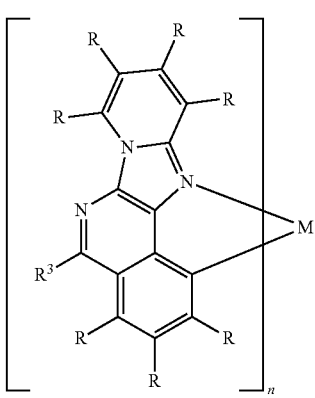
formula (30a)
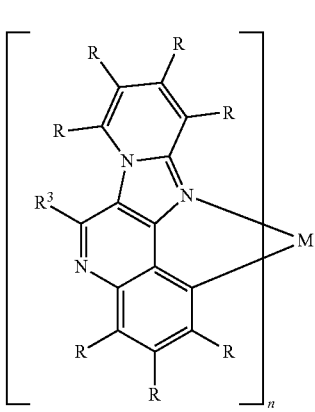
formula (30b)
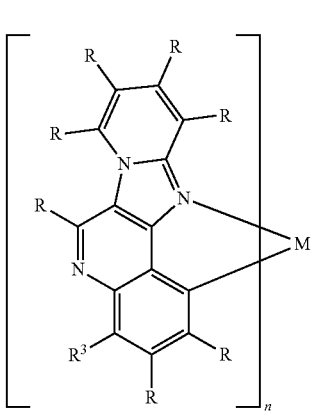

formula (31a)

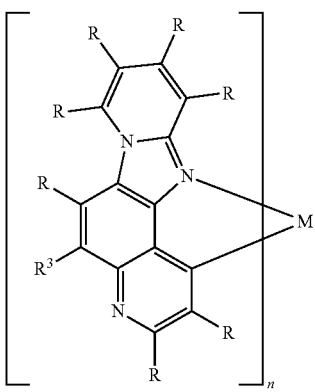

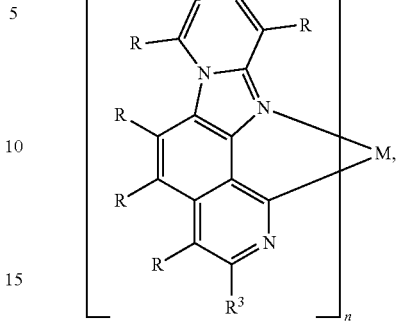

formula (31b)

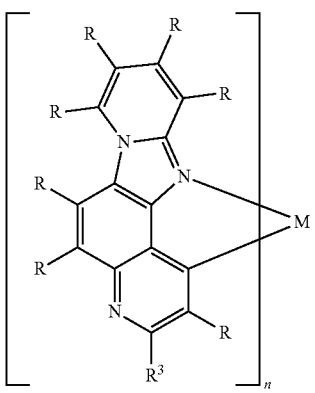

formula (32a)

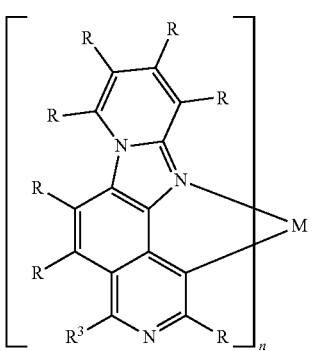

formula (32b)

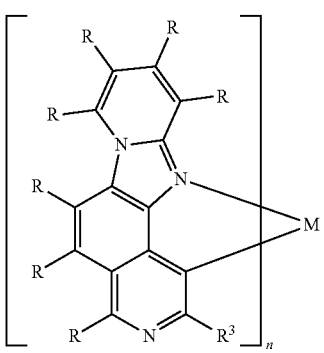

formula (33a)

where the symbols and indices used have the meanings given in claim 1 and $R^3$ is on each occurrence, identically or differently, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals $R^1$, where one or more non-adjacent $CH_2$ groups is optionally replaced by $R^1C=CR^1$, $C\equiv C$, $Si(R^1)_2$, $C=O$, $NR^1$, O, S or $CONR^1$ and where one or more H atoms is optionally replaced by D, F, Cl, Br, I or CN, or an aromatic or heteroaromatic ring system having 5 to 60 aromatic ring atoms, which may in each case be substituted by one or more radicals $R^1$, or an aryloxy or heteroaryloxy group having 5 to 40 aromatic ring atoms, which is optionally substituted by one or more radicals $R^1$, or an aralkyl or heteroaralkyl group having 5 to 40 aromatic ring atoms, which is optionally substituted by one or more radicals $R^1$, or a diarylamino group, diheteroarylamino group or arylheteroarylamino group having 10 to 40 aromatic ring atoms, which is optionally substituted by one or more radicals $R^1$; $R^3$ here may also form a mono- or polycyclic, aliphatic, aromatic and/or benzo-fused ring system with an adjacent radical R.

7. The compound according to claim 5, wherein $R^3$ is selected from the structures of the following formulae $(R^3\text{-}1)$ to $(R^3\text{-}115)$, where in each case the linking of these groups to the ligand is also shown:

(R³-1)

(R³-2)

(R³-3)

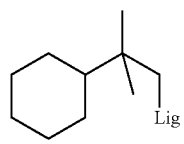
(R³-4)
(R³-5)
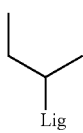
(R³-6)
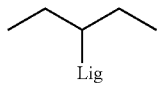
(R³-7)
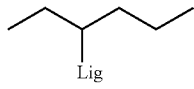
(R³-8)
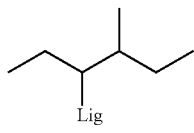
(R³-9)
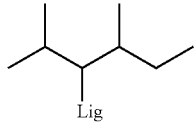
(R³-10)
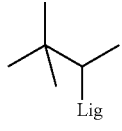
(R³-11)
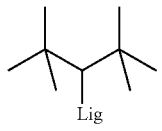
(R³-12)
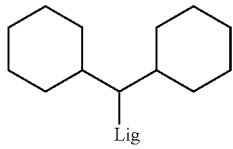
(R³-13)
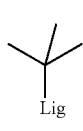
(R³-14)
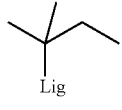
(R³-15)
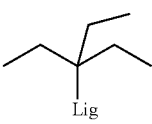
(R³-16)
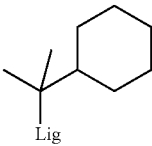
(R³-17)
(R³-18)
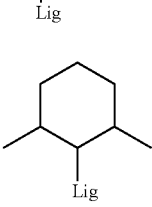
(R³-19)
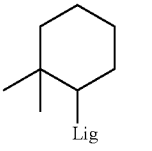
(R³-20)
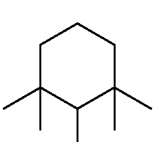
(R³-21)
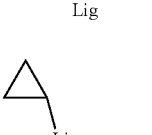
(R³-22)
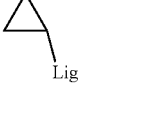
(R³-23)
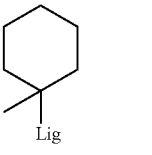
(R³-24)
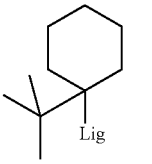
(R³-25)
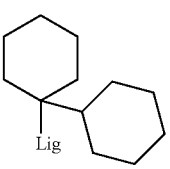

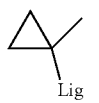 (R³-26)
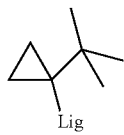 (R³-27)
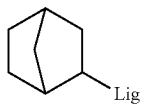 (R³-28)
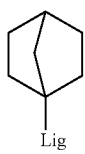 (R³-29)
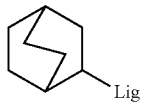 (R³-30)
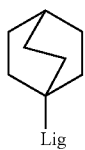 (R³-31)
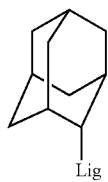 (R³-32)
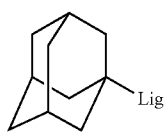 (R³-33)
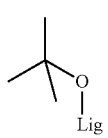 (R³-34)
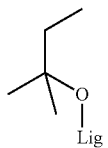 (R³-35)
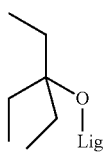 (R³-36)
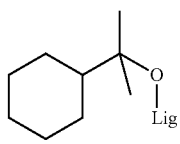 (R³-37)
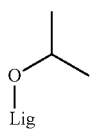 (R³-38)
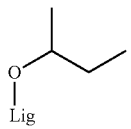 (R³-39)
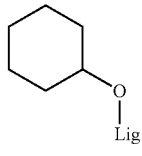 (R³-40)
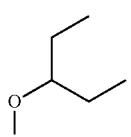 (R³-41)
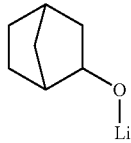 (R³-42)
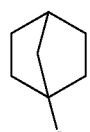 (R³-43)
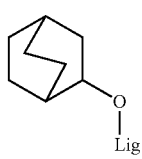 (R³-44)

(R³-45) 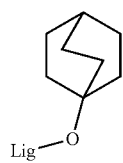
(R³-46) 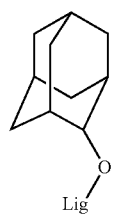
(R³-47) 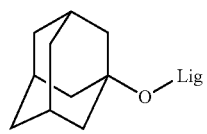
(R³-48) 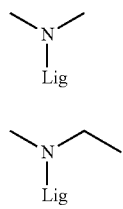
(R³-49) 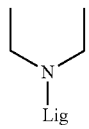
(R³-50) 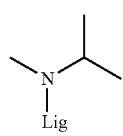
(R³-51) 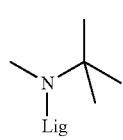
(R³-52) 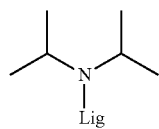
(R³-53) 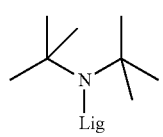
(R³-54) 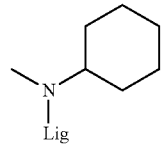
(R³-55) 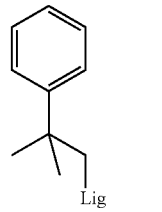
(R³-56) 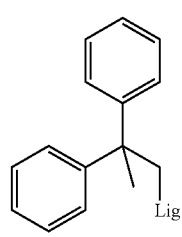
(R³-57) 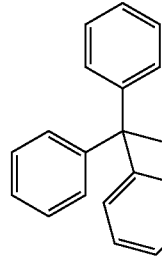
(R³-58) 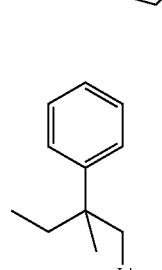
(R³-59) 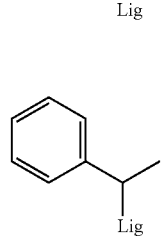
(R³-60) 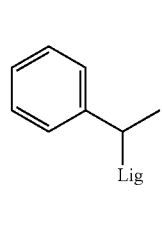
(R³-61) 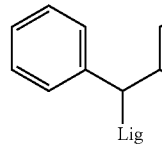

(R³-62) 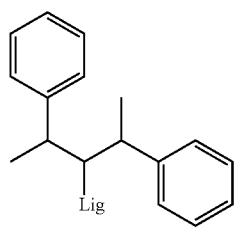
(R³-63) 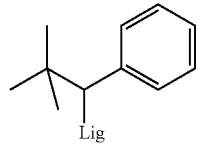
(R³-64) 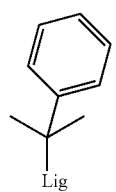
(R³-65) 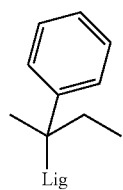
(R³-66) 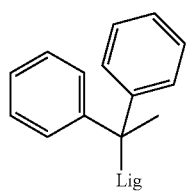
(R³-67) 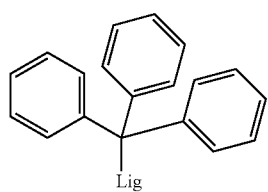
(R³-68) 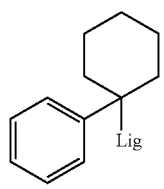
(R³-69) 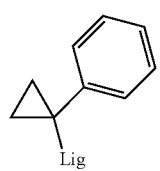
(R³-70) 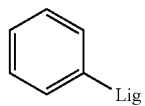
(R³-71) 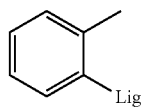
(R³-72) 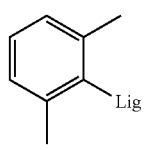
(R³-73) 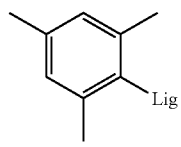
(R³-74) 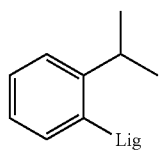
(R³-75) 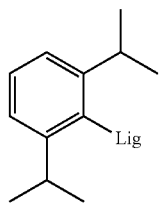
(R³-76) 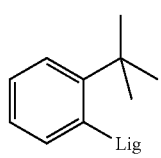
(R³-77) 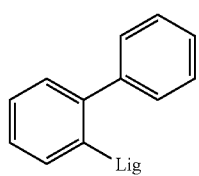
(R³-78) 

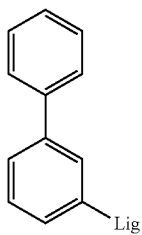 (R³-79)
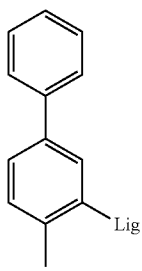 (R³-80)
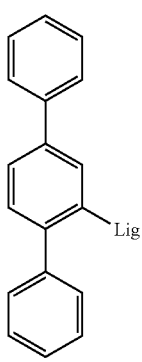 (R³-81)
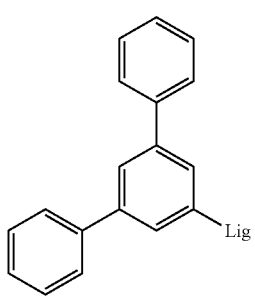 (R³-82)
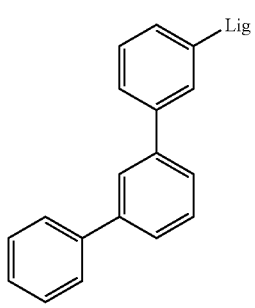 (R³-83)
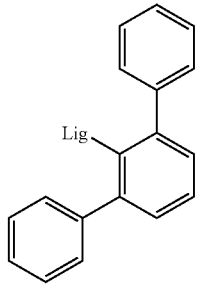 (R³-84)
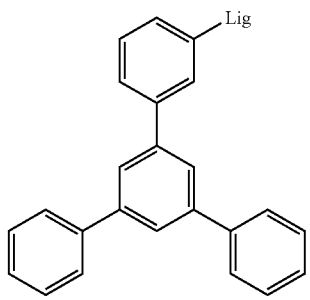 (R³-84a)
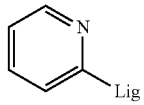 (R³-85)
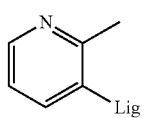 (R³-86)
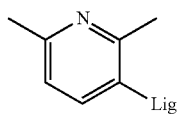 (R³-87)
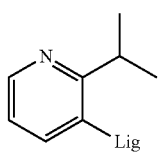 (R³-88)
(R³-89)
(R³-90)

(R³-91) 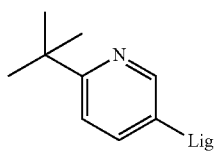
(R³-92) 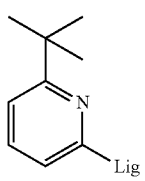
(R³-93) 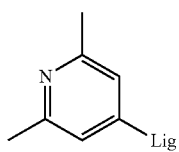
(R³-94) 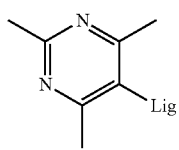
(R³-95) 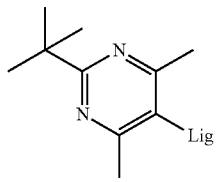
(R³-96) 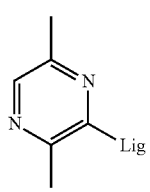
(R³-97) 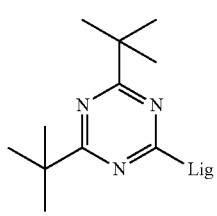
(R³-98) 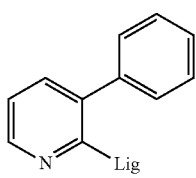
(R³-99) 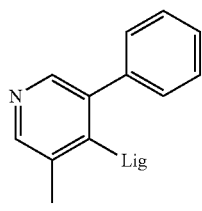
(R³-100) 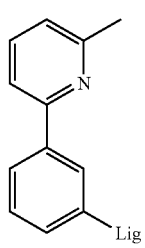
(R³-101) 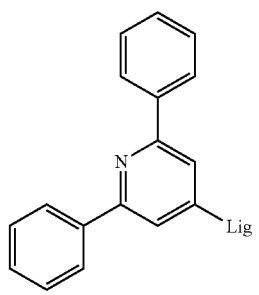
(R³-102) 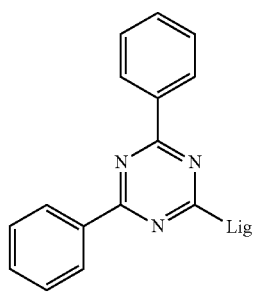
(R³-103) 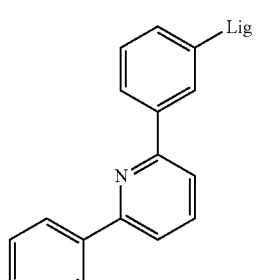
(R³-104) 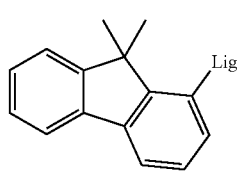

(R³-105) 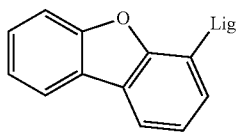

(R³-106) 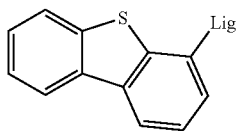

(R³-107) 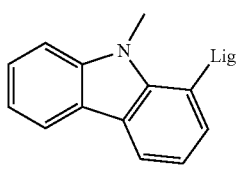

(R³-108) 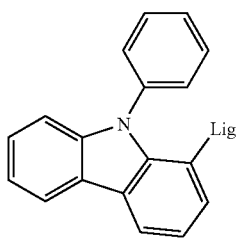

(R³-109) 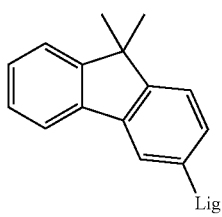

(R³-110) 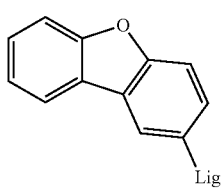

(R³-111) 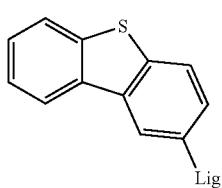

(R³-112) 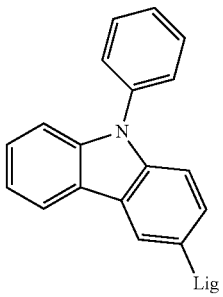

(R³-113) 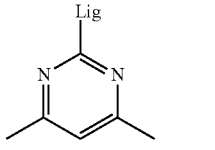

(R³-114) 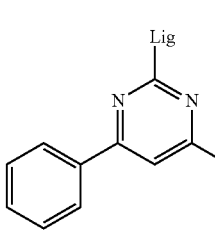

(R³-115) 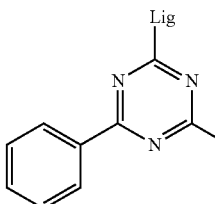

where Lig denotes the linking of the group to the ligand and the aromatic and heteroaromatic groups may each be substituted by one or more radicals R¹.

8. The compound according to claim 1, wherein the radicals R are selected on each occurrence, identically or differently, from the group consisting of H, D, F, Br, I, N(R¹)₂, CN, Si(R¹)₃, B(OR¹)₂, C(=O)R¹, a straight-chain alkyl group having 1 to 10 C atoms or an alkenyl group having 2 to 10 C atoms or a branched or cyclic alkyl group having 3 to 10 C atoms, each of which is optionally substituted by one or more radicals R¹, where one or more H atoms is optionally replaced by D or F, or an aromatic or heteroaromatic ring system having 5 to 30 aromatic ring atoms, which may in each case be substituted by one or more radicals R¹; two adjacent radicals R here may also form a mono- or polycyclic and/or aliphatic fused ring system with one another; the radicals R which are bonded to the central six-membered ring do not form an aromatic or benzo-fused ring system with one another.

9. The compound according to claim 1, wherein the substituent R which is in the ortho-position to the metal coordination represents a group which is coordinated to the metal M and is selected from aryl or heteroaryl groups, aryl or alkyl cyanides, aryl or alkyl isocyanides, amines, amides, alcohols, alcoholates, thioalcohols, thioalcoholates, phosphines, phosphites, carbonyl functions, carboxylates, carbamides or aryl- or alkylacetylides.

10. The compound according to claim 1, selected from metal complexes of the formulae (41) to (46), formula (41)
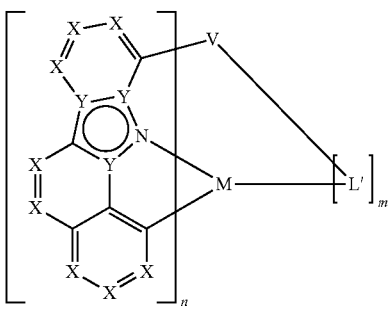

formula (42)
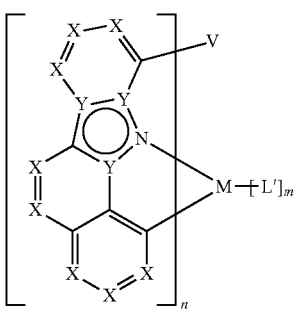

formula (43)
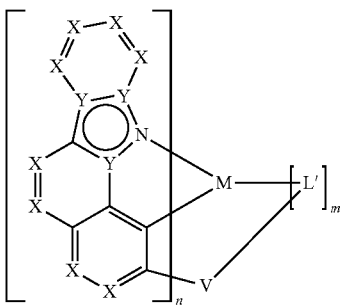

formula (44)
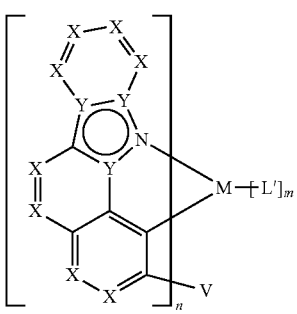

formula (45)
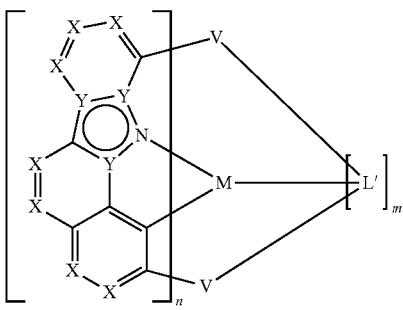

formula (46)
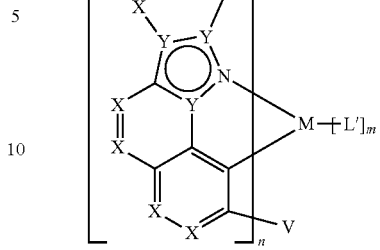

where the symbols used have the meanings given above, where V represents a bridging unit containing 1 to 80 atoms from the third, fourth, fifth and/or sixth main group (IUPAC group 13, 14, 15 or 16), which may also be substituted by one or more radicals $R^1$, or a 3- to 6-membered homo- or heterocycle which covalently connects the part-ligands L to one another or L to L' to one another.

11. The compound according to claim 1, wherein the ligand L' is identically or differently on each occurrence, carbon monoxide, nitrogen monoxide, alkyl cyanides, aryl cyanides, alkyl isocyanides, aryl isocyanides, amines, phosphines, phosphites, arsines, stibines, nitrogen-containing heterocycles, carbenes, hydride, deuteride, the halides $F^-$, $Cl^-$, $Br^-$ and $I^-$, alkylacetylides, arylacetylides, cyanide, cyanate, isocyanate, thiocyanate, isothiocyanate, aliphatic or aromatic alcoholates, aliphatic or aromatic thioalcoholates, amides, carboxylates, aryl groups, $O^{2-}$, $S^{2-}$, carbides, nitrenes, diamines, imines, diimines, diphosphines, 1,3-diketonates, 3-ketonates derived from 3-ketoesters, carboxylates derived from aminocarboxylic acids, salicyliminates derived from salicylimines, dialcoholates, dithiolates, borates of nitrogen-containing heterocycles and ligands which have a cyclometallated five-membered ring or six-membered ring with the metal.

12. A process for the preparation of the compound according to claim 1 which comprises reacting the ligand with metal alcoholates of the formula (93), with metal ketoketonates of the formula (94), with metal halides of the formula (95) or with dimeric metal complexes of the formula (96), $M(OR)_n$  formula (93)

formula (94)
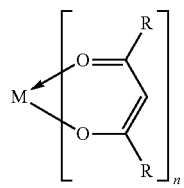

$MHal_n$  formula (95)

formula (96)

where the symbols M, L', m, n and R have the meanings indicated in claim 1 and Hal=F, Cl, Br or I.

13. An electronic device which comprises the compound according to claim 1.

14. The electronic device as claimed in claim 13, wherein the device is an organic electroluminescent device, organic integrated circuit, organic field-effect transistor, organic thin-film transistor, organic light-emitting transistor, organic solar cell, organic optical detector, organic photoreceptor, organic field-quench device, light-emitting electrochemical cell or organic laser diode.

15. An organic electroluminescent device which comprises the compound according to claim 1 is employed as emitting compound in one or more emitting layers.

16. An organic electroluminescent device which comprises the compound according to claim 1 is employed as emitting compound in one or more emitting layers in combination with one or more matrix materials.

17. A compound of the formula (1)

formula (1)

where the compound contains a moiety $M(L)_n$ of the formula (2):

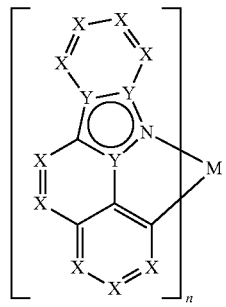

formula (2)

where the following applies to the symbols and indices used:

M is a metal;

Y is on each occurrence, identically or differently, C or N, with the proviso that precisely one symbol Y in each ligand stands for N and the other two symbols Y stand for C;

X is on each occurrence, identically or differently, CR or N; and in which at least one group X=N, wherein at least one group X which is adjacent to this nitrogen atom stands for a $CR^3$ group, where $R^3$ is on each occurrence, identically or differently, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals $R^1$, where one or more non-adjacent $CH_2$ groups is optionally replaced by $R^1C=CR^1$, C≡C, $Si(R^1)_2$, C=O, $NR^1$, O, S or $CONR^1$ and where one or more H atoms is optionally replaced by D, F, Cl, Br, I or CN, or an aromatic or heteroaromatic ring system having 5 to 60 aromatic ring atoms, which may in each case be substituted by one or more radicals $R^1$, or an aryloxy or heteroaryloxy group having 5 to 40 aromatic ring atoms, which is optionally substituted by one or more radicals $R^1$, or an aralkyl or heteroaralkyl group having 5 to 40 aromatic ring atoms, which is optionally substituted by one or more radicals $R^1$, or a diarylamino group, diheteroarylamino group or arylheteroarylamino group having 10 to 40 aromatic ring atoms, which is optionally substituted by one or more radicals $R^1$; $R^3$ here may also form a mono- or polycyclic, aliphatic, aromatic and/or benzo-fused ring system with an adjacent radical R;

R is on each occurrence, identically or differently, H, D, F, Cl, Br, I, $N(R^1)_2$, CN, $NO_2$, OH, COOH, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals $R^1$, where one or more non-adjacent $CH_2$ groups is optionally replaced by $R^1C=CR^1$, C≡C, $Si(R^1)_2$, C=O, $NR^1$, O, S or $CONR^1$ and where one or more H atoms is optionally replaced by D, F, Cl, Br, I or CN, or an aromatic or heteroaromatic ring system having 5 to 60 aromatic ring atoms, which may in each case be substituted by one or more radicals $R^1$, or an aryloxy or heteroaryloxy group having 5 to 40 aromatic ring atoms, which is optionally substituted by one or more radicals $R^1$, or an aralkyl or heteroaralkyl group having 5 to 40 aromatic ring atoms, which is optionally substituted by one or more radicals $R^1$, or a diarylamino group, diheteroarylamino group or arylheteroarylamino group having 10 to 40 aromatic ring atoms, which is optionally substituted by one or more radicals $R^1$; two adjacent radicals R here may also form a mono- or polycyclic, and/or aliphatic ring system with one another, with the proviso that the two adjacent radicals R do not form a benzo-fused ring system;

$R^1$ is on each occurrence, identically or differently, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals $R^2$; where one or more non-adjacent $CH_2$ groups is optionally replaced by $R^2C=CR^2$, C≡C, $Si(R^2)_2$, C=O, $NR^2$, O, S or $CONR^2$ and where one or more H atoms is optionally replaced by D, F, Cl, Br, I, CN, or $NO_2$, or an aromatic or heteroaromatic ring system having 5 to 60 aromatic ring atoms, which may in each case be substituted by one or more radicals $R^2$, or an aryloxy or heteroaryloxy group having 5 to 40 aromatic ring atoms, which is optionally substituted by one or more radicals $R^2$, or an aralkyl or heteroaralkyl group having 5 to 40 aromatic ring atoms, which is optionally substituted by one or more radicals $R^2$, or a diarylamino group, diheteroarylamino group or arylheteroarylamino group having 10 to 40 aromatic ring atoms, which is optionally substituted by one or more radicals $R^2$; two adjacent radicals $R^1$ here may also form a mono- or polycyclic, aliphatic, aromatic and/or benzo-fused ring system with one another;

$R^2$ is on each occurrence, identically or differently, H, D, F or an aliphatic, aromatic and/or heteroaromatic hydrocarbon radical having 1 to 20 C atoms, in which, in addition, one or more H atoms is optionally replaced by F; two or more substituents R² here may also form a mono- or polycyclic aliphatic ring system with one another;

L' is, identically or differently on each occurrence, a co-ligand;

n is 1, 2 or 3;

m is 0, 1, 2, 3 or 4;

a plurality of ligands L here may also be linked to one another or L is optionally linked to L' via any desired bridge V and thus form a tridentate, tetradentate, pentadentate or hexadentate ligand system and/or a substituent R may additionally be coordinated to the metal;

the following compounds are excluded from the invention:

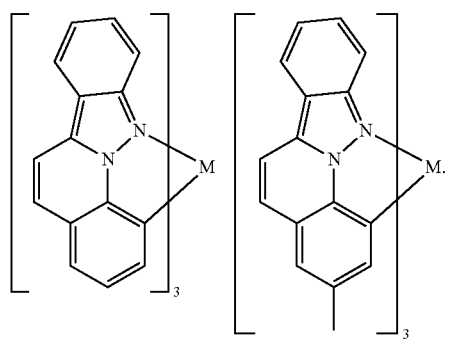

18. The compound according to claim 17, selected from the structures of the formulae (7a) to (33a) and (8b) to (32b),

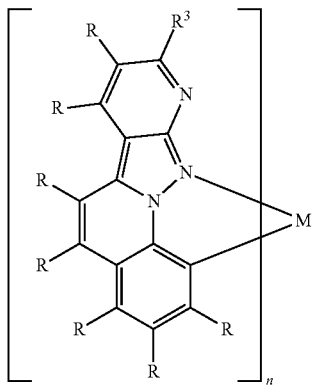

formula (7a)

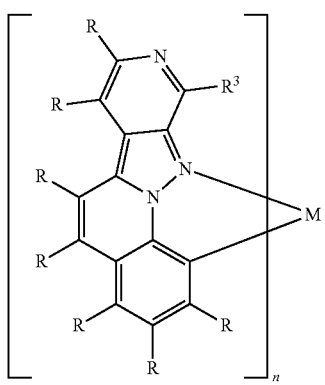

formula (8a)

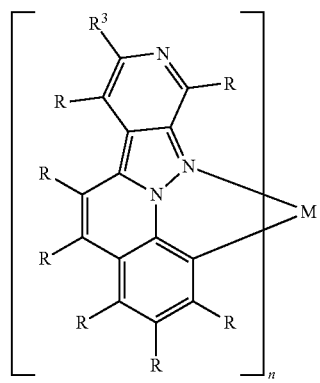

formula (8b)

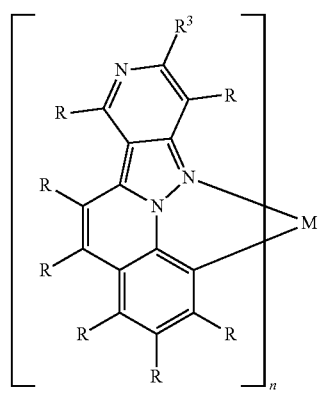

formula (9a)

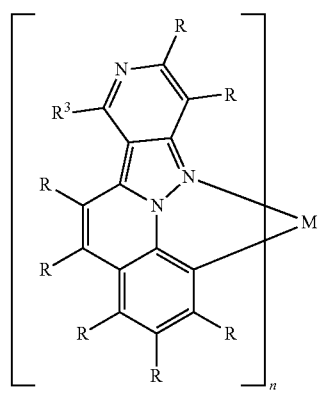

formula (9b)

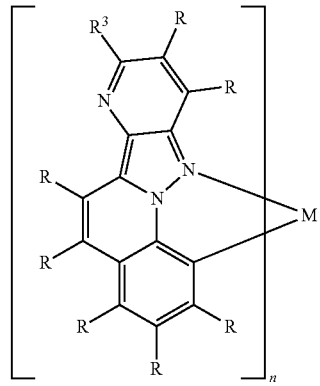

formula (10a)

formula (10b)
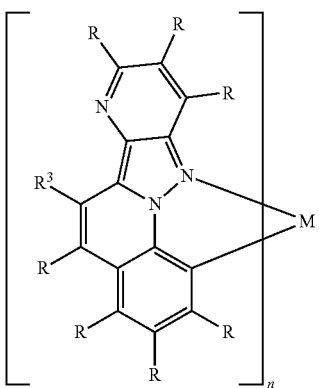
formula (11a)
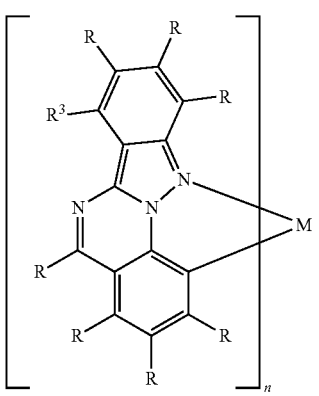
formula (11b)
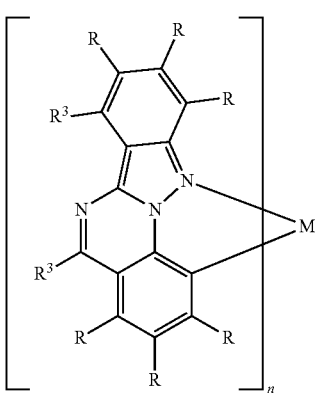
formula (12a)
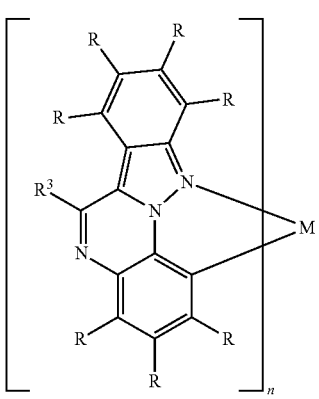
formula (12b)
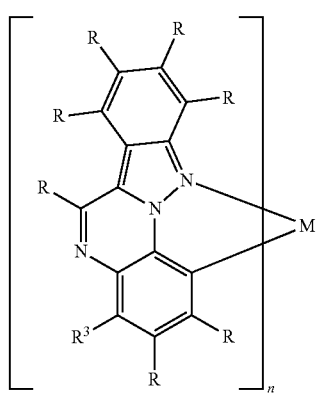
formula (13a)
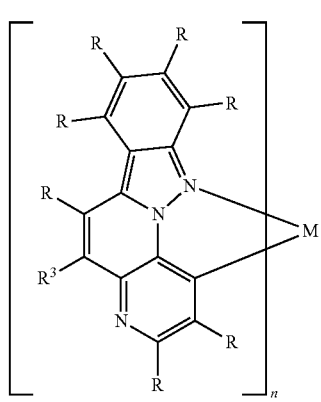
formula (13b)
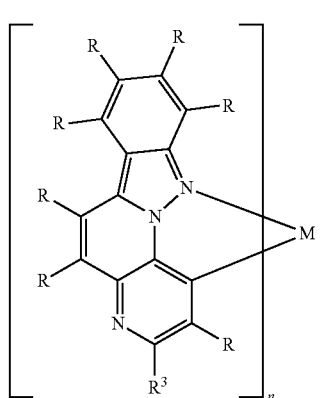
formula (14a)
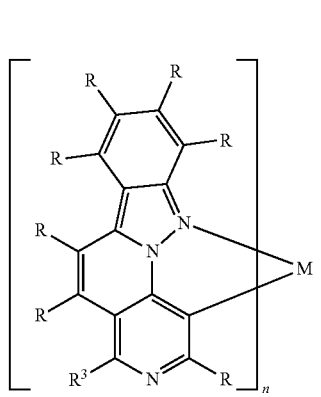

formula (14b)
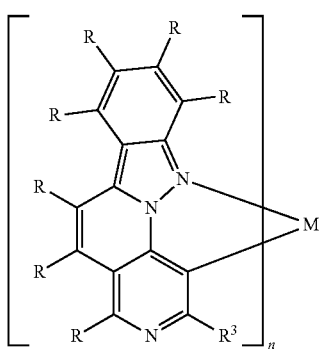
formula (15a)
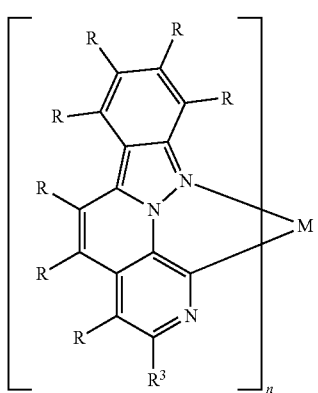
formula (16a)
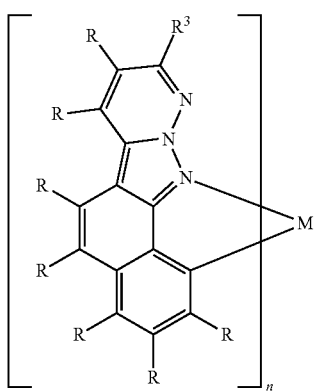
formula (17a)
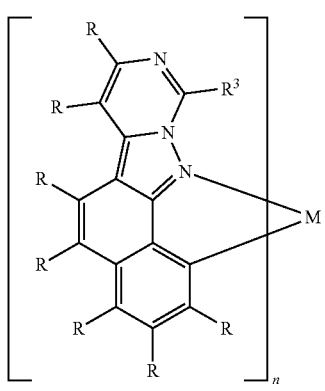
formula (17b)
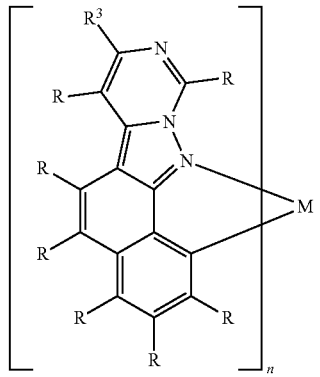
formula (18a)
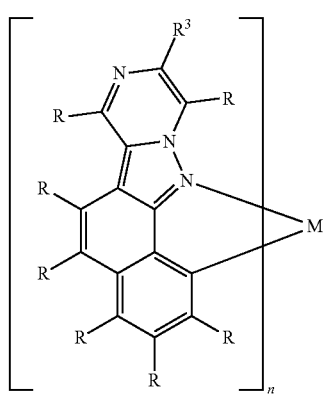
formula (18b)
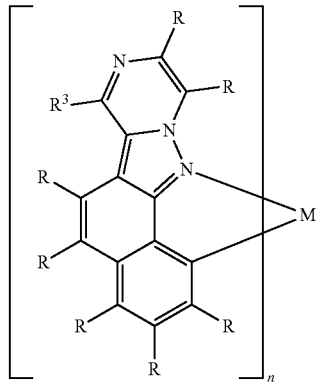
formula (19a)
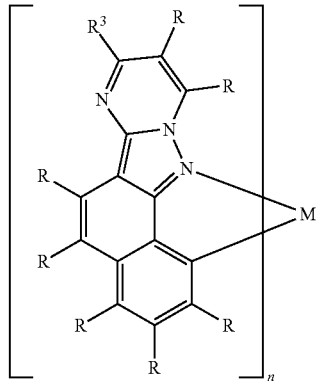

formula (19b)
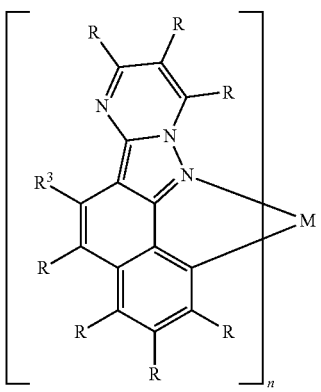
formula (20a)
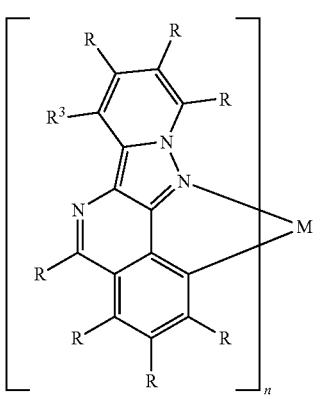
formula (20b)
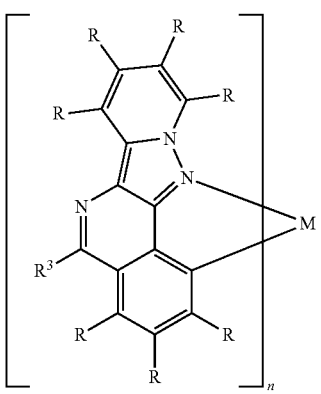
formula (21a)
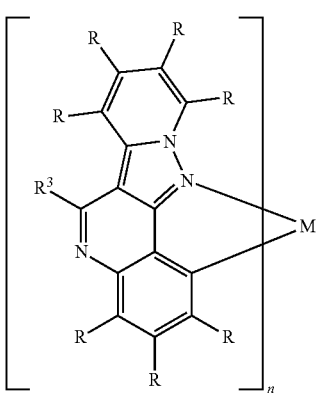
formula (21b)
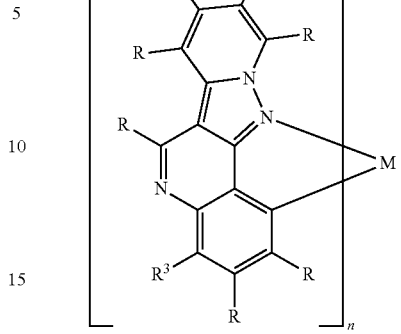
formula (22a)
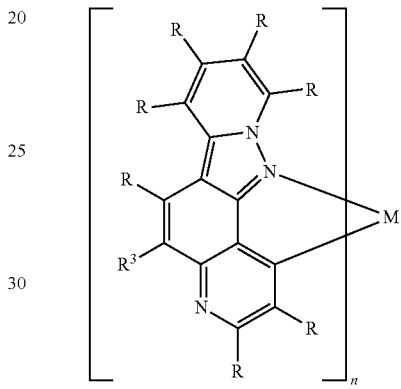
formula (22b)
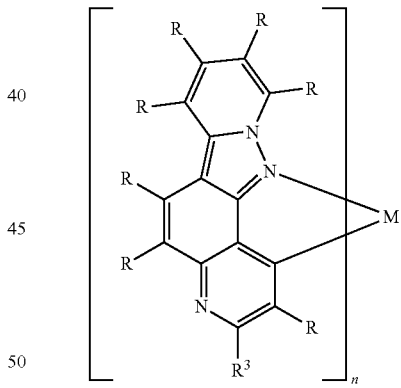
formula (23a)
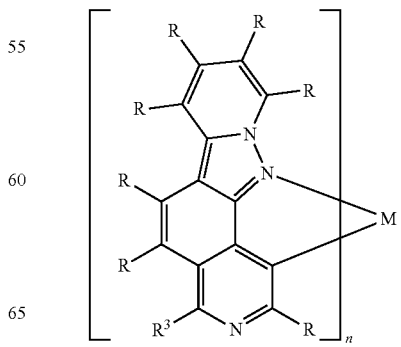

181
-continued
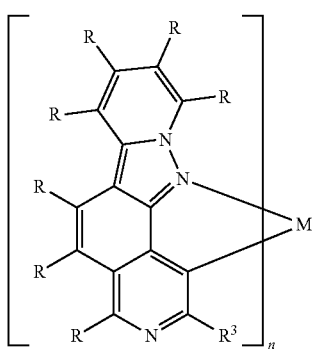
formula (23b)
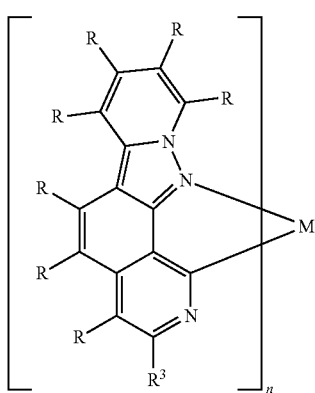
formula (24a)
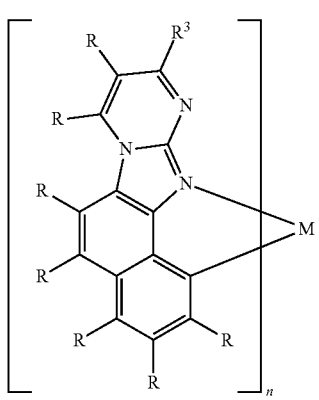
formula (25a)
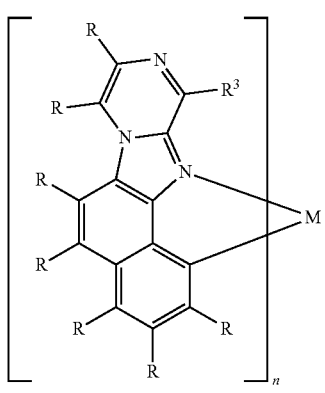
formula (26a)
182
-continued
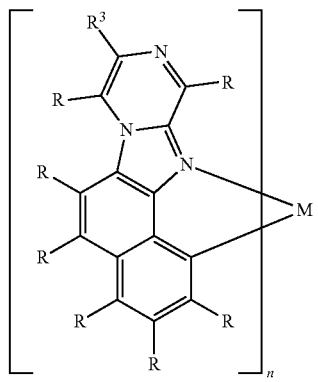
formula (26b)
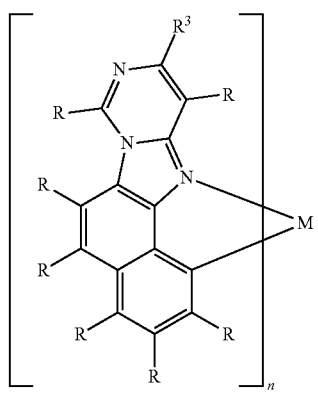
formula (27a)
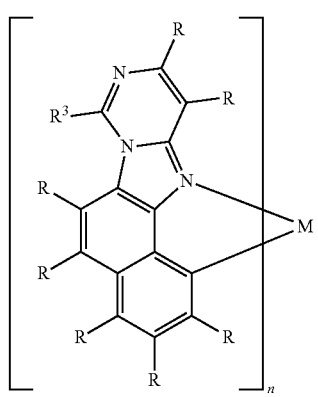
formula (27b)
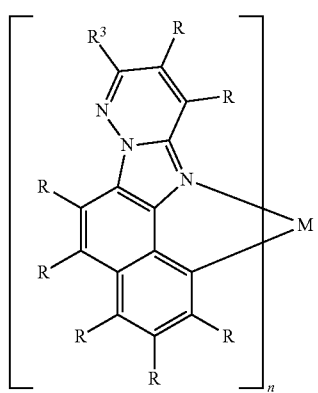
formula (28a)

-continued
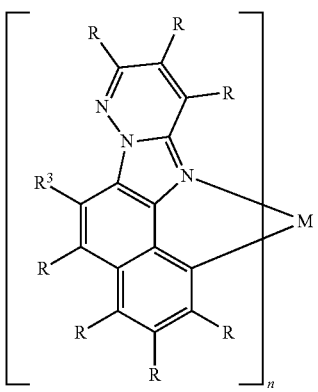
formula (28b)
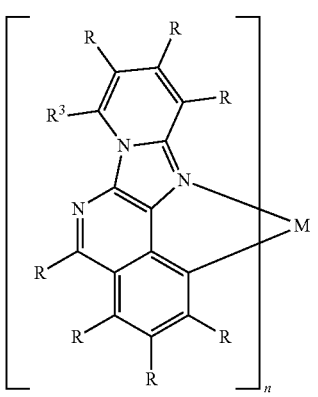
formula (29a)
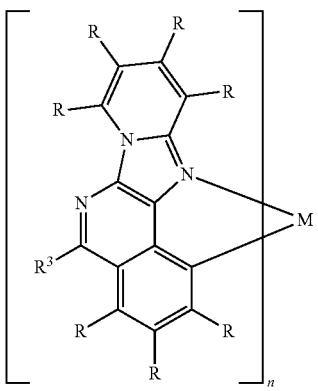
formula (29b)
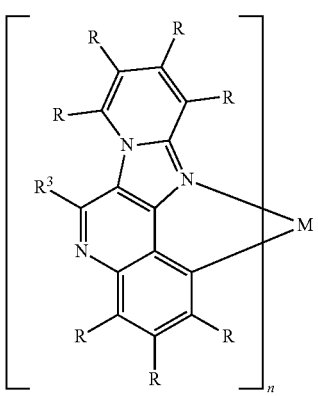
formula (30a)
-continued
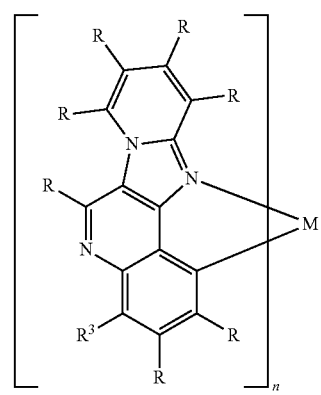
formula (30b)
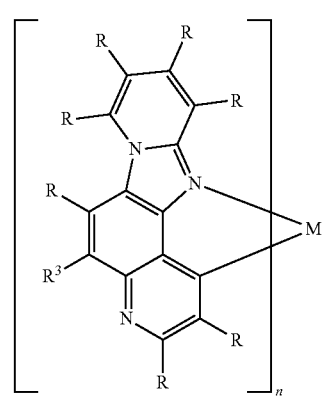
formula (31a)
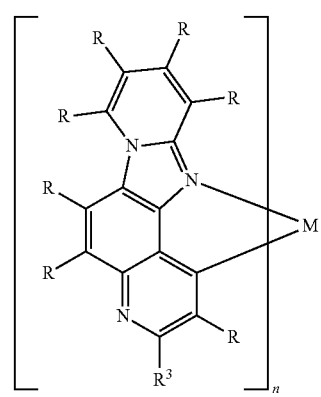
formula (31b)
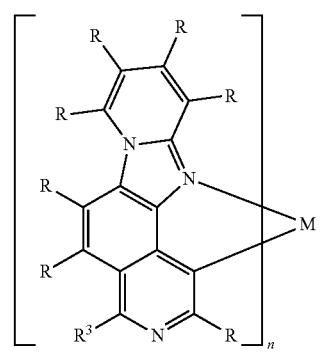
formula (32a)

formula (32b)

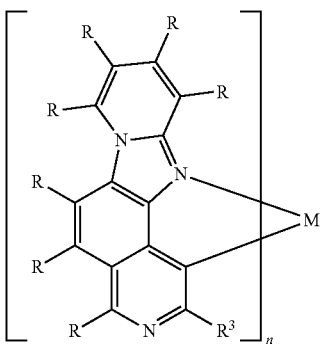

formula (33a)

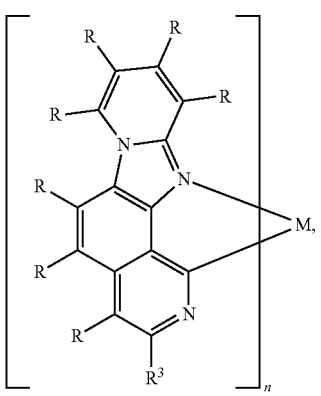

where the symbols and indices used have the meanings given in claim 17 and $R^3$ is on each occurrence, identically or differently, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals $R^1$, where one or more non-adjacent $CH_2$ groups is optionally replaced by $R^1C$=$CR^1$, C≡C, $Si(R^1)_2$, C=O, $NR^1$, O, S or $CONR^1$ and where one or more H atoms is optionally replaced by D, F, Cl, Br, I or CN, or an aromatic or heteroaromatic ring system having 5 to 60 aromatic ring atoms, which may in each case be substituted by one or more radicals $R^1$, or an aryloxy or heteroaryloxy group having 5 to 40 aromatic ring atoms, which is optionally substituted by one or more radicals $R^1$, or an aralkyl or heteroaralkyl group having 5 to 40 aromatic ring atoms, which is optionally substituted by one or more radicals $R^1$, or a diarylamino group, diheteroarylamino group or aryl-heteroarylamino group having 10 to 40 aromatic ring atoms, which is optionally substituted by one or more radicals $R^1$; $R^3$ here may also form a mono- or polycyclic, aliphatic, aromatic and/or benzo-fused ring system with an adjacent radical R.

19. The compound according to claim 17, wherein $R^3$ is selected from the structures of the following formulae ($R^3$-1) to ($R^3$-115), where in each case the linking of these groups to the ligand is also shown:

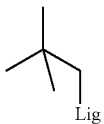
($R^3$-1)

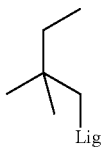
($R^3$-2)

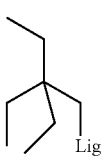
($R^3$-3)

($R^3$-4)

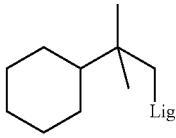

($R^3$-5)

($R^3$-6)

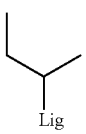

($R^3$-7)

($R^3$-8)

($R^3$-9)

($R^3$-10)

($R^3$-11)

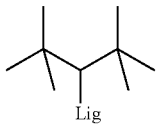
($R^3$-12)

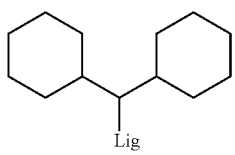 (R³-13)
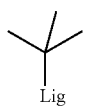 (R³-14)
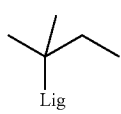 (R³-15)
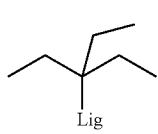 (R³-16)
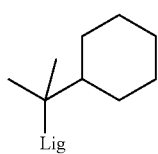 (R³-17)
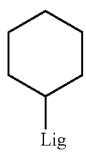 (R³-18)
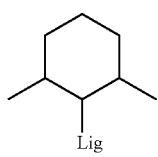 (R³-19)
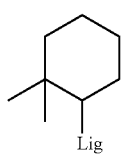 (R³-20)
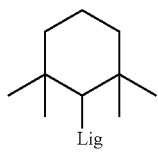 (R³-21)
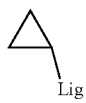 (R³-22)
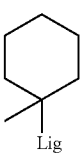 (R³-23)
(R³-24)
(R³-25)
(R³-26)
(R³-27)
(R³-28)
(R³-29)
(R³-30)
(R³-31)
(R³-32)

(R³-33) 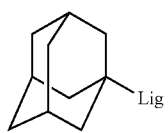
(R³-34) 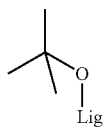
(R³-35) 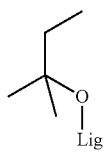
(R³-36) 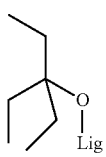
(R³-37) 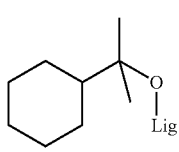
(R³-38) 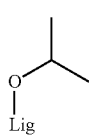
(R³-39) 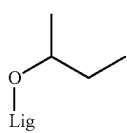
(R³-40) 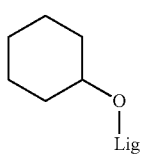
(R³-41) 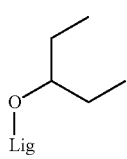
(R³-42) 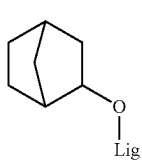
(R³-43) 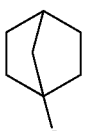
(R³-44) 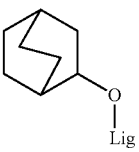
(R³-45) 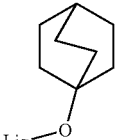
(R³-46) 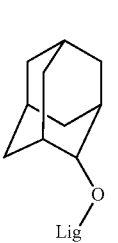
(R³-47) 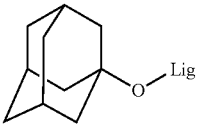
(R³-48) 
(R³-49) 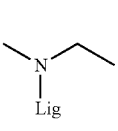
(R³-50) 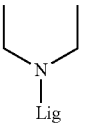
(R³-51) 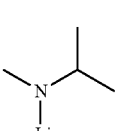
(R³-52) 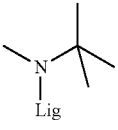

-continued
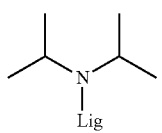 (R³-53)
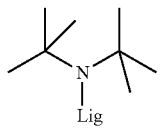 (R³-54)
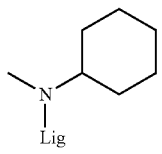 (R³-55)
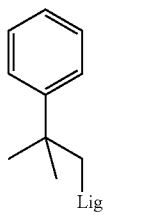 (R³-56)
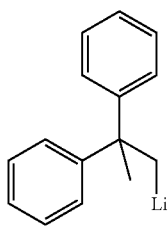 (R³-57)
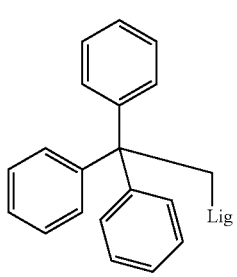 (R³-58)
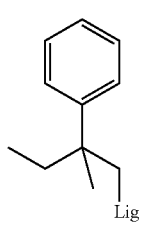 (R³-59)
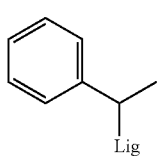 (R³-60)
-continued
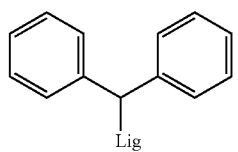 (R³-61)
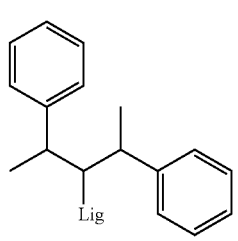 (R³-62)
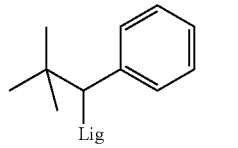 (R³-63)
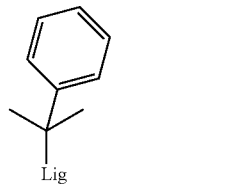 (R³-64)
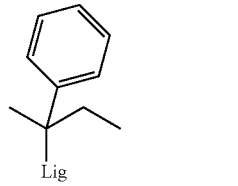 (R³-65)
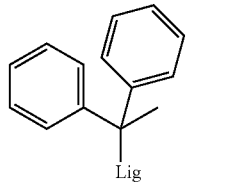 (R³-66)
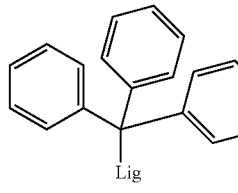 (R³-67)
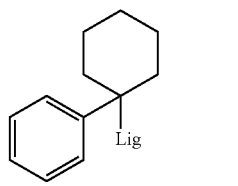 (R³-68)

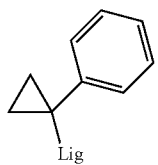 (R³-69)
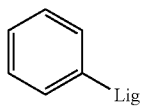 (R³-70)
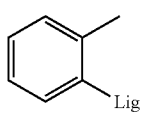 (R³-71)
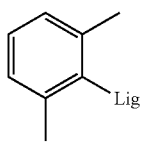 (R³-72)
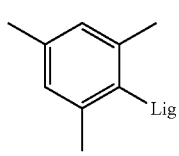 (R³-73)
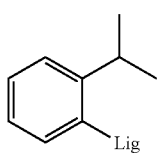 (R³-74)
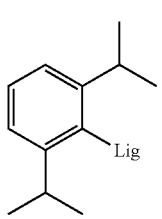 (R³-75)
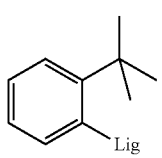 (R³-76)
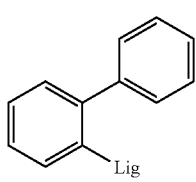 (R³-77)
 (R³-78)
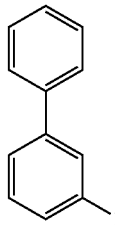 (R³-79)
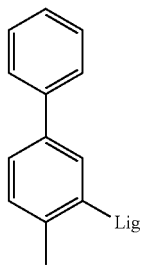 (R³-80)
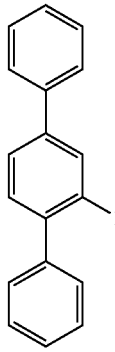 (R³-81)
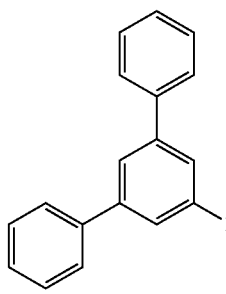 (R³-82)

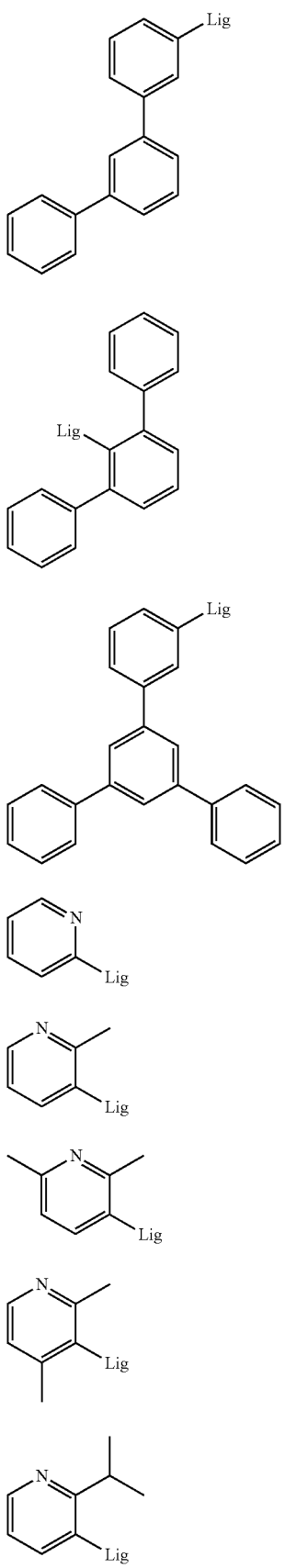
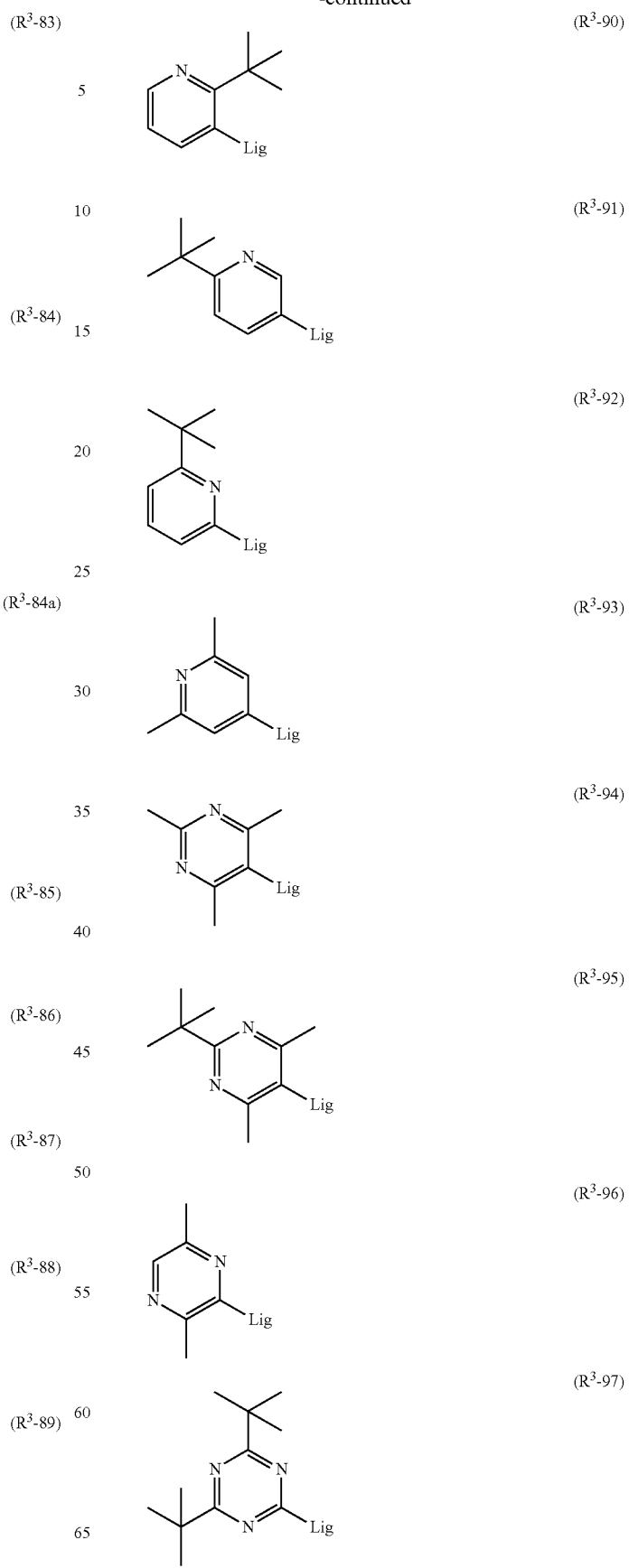

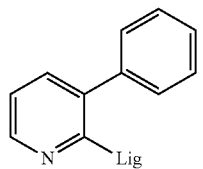 (R³-98)
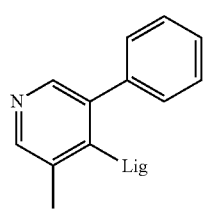 (R³-99)
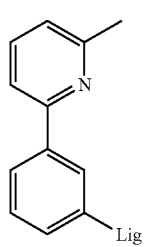 (R³-100)
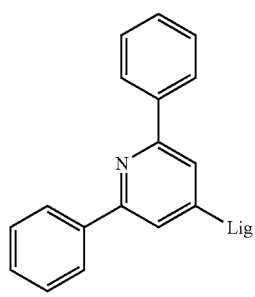 (R³-101)
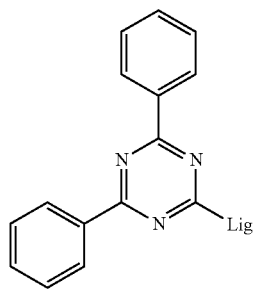 (R³-102)
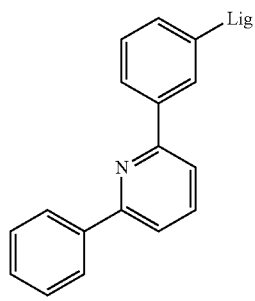 (R³-103)
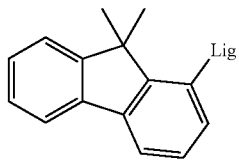 (R³-104)
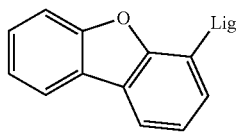 (R³-105)
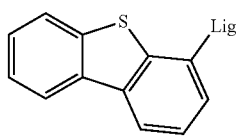 (R³-106)
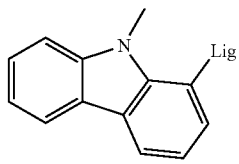 (R³-107)
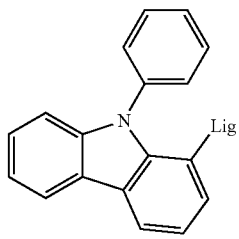 (R³-108)
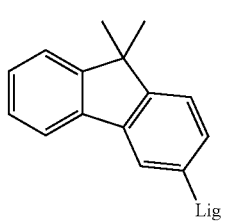 (R³-109)
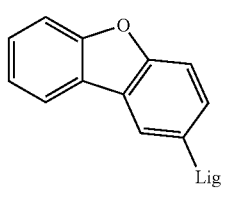 (R³-110)
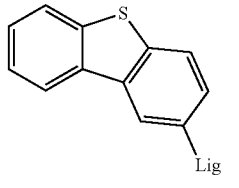 (R³-111)

(R³-112)

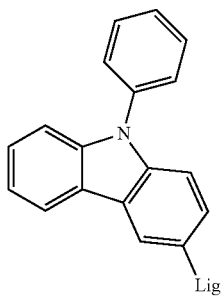

(R³-113)

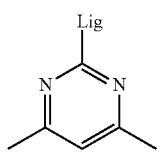

(R³-114)

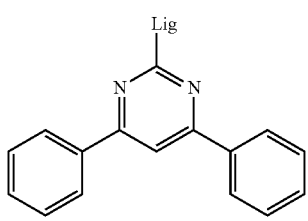

(R³-115)

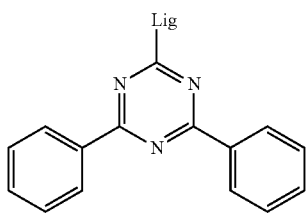

where Lig denotes the linking of the group to the ligand and the aromatic and heteroaromatic groups may each be substituted by one or more radicals R¹.

20. The compound according to claim 17, wherein the substituent R which is in the ortho-position to the metal coordination represents a group which is coordinated to the metal M and is selected from aryl or heteroaryl groups, aryl or alkyl cyanides, aryl or alkyl isocyanides, amines, amides, alcohols, alcoholates, thioalcohols, thioalcoholates, phosphines, phosphites, carbonyl functions, carboxylates, carbamides or aryl- or alkylacetylides.

21. The compound according to claim 17, selected from metal complexes of the formulae (41) to (46), formula (41)

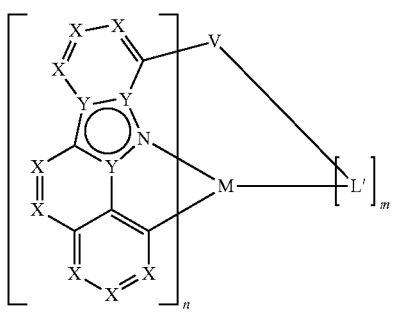

formula (42)

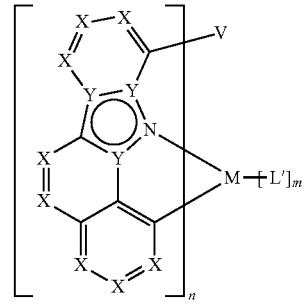

formula (43)

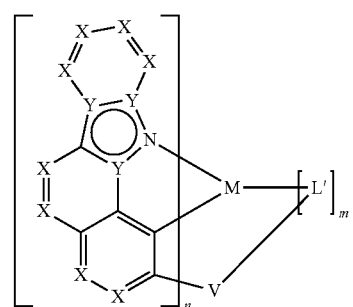

formula (44)

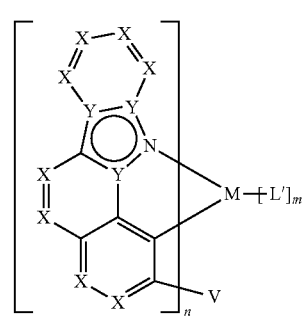

formula (45)

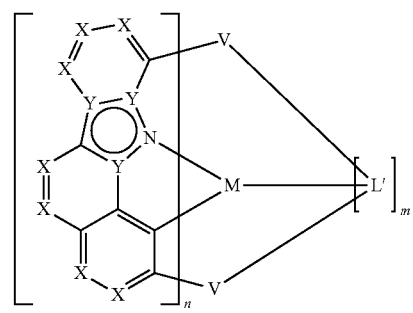

formula (46)

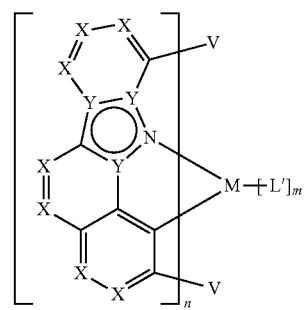

where the symbols used have the meanings given above, where V represents a bridging unit containing 1 to 80 atoms from the third, fourth, fifth and/or sixth main group (IUPAC group 13, 14, 15 or 16), which may also be substituted by one or more radicals R¹, or a 3- to 6-membered homo- or heterocycle which covalently connects the part-ligands L to one another or L to L' to one another.
22. A compound of the formula (1),
  formula (1)
where the compound contains a moiety $M(L)_n$ of the formulae (5) to (33),
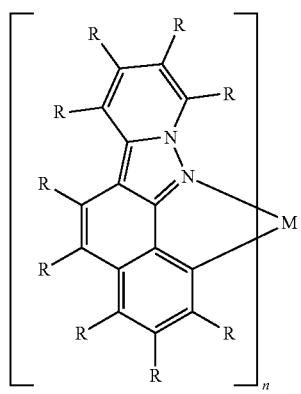  formula (5)
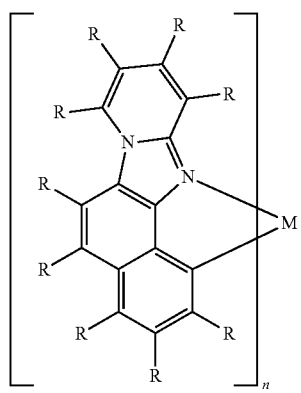  formula (6)
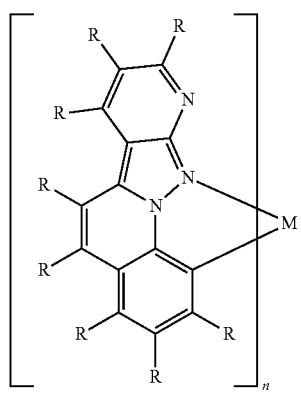  formula (7)
-continued
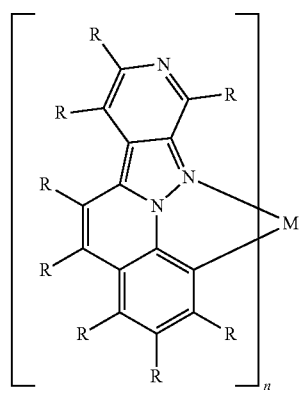  formula (8)
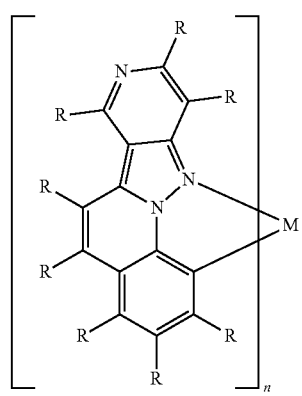  formula (9)
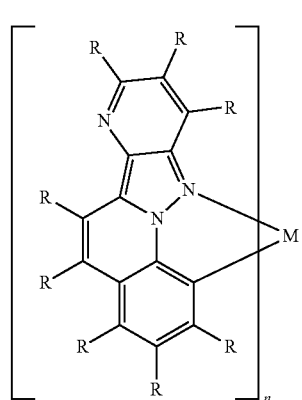  formula (10)
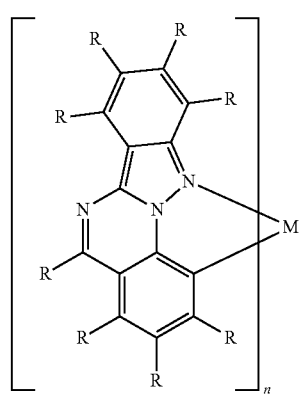  formula (11)

formula (12)
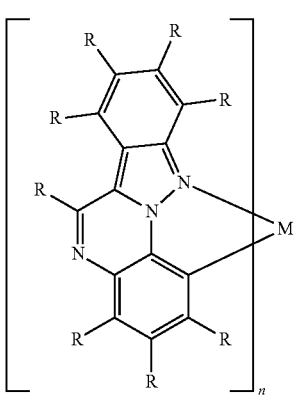
formula (13)
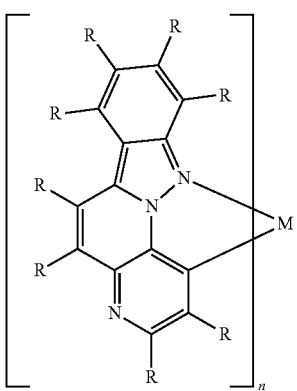
formula (14)
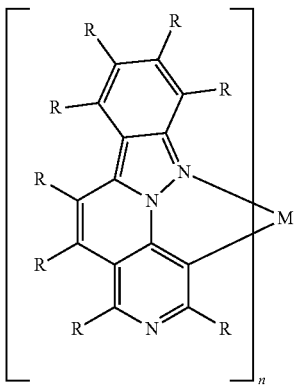
formula (15)
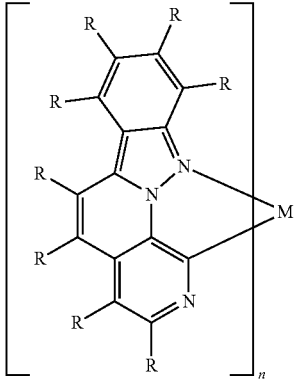
formula (16)
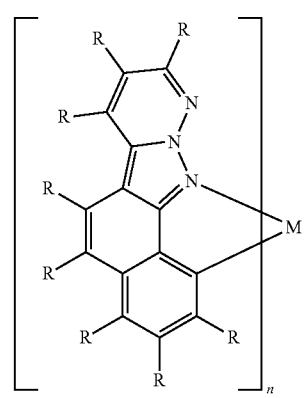
formula (17)
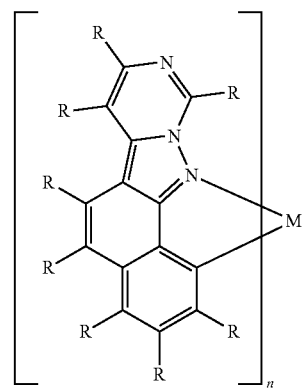
formula (18)
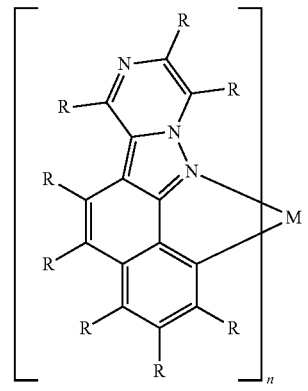
formula (19)
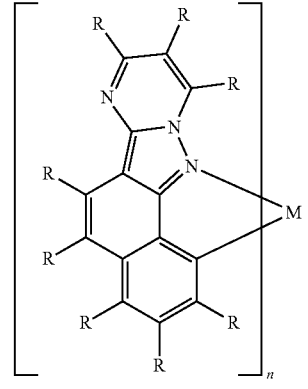

formula (20)
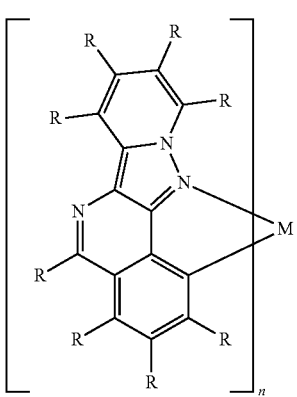
formula (21)
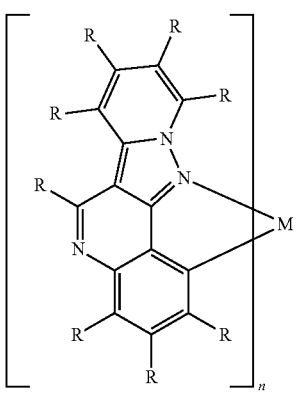
formula (22)
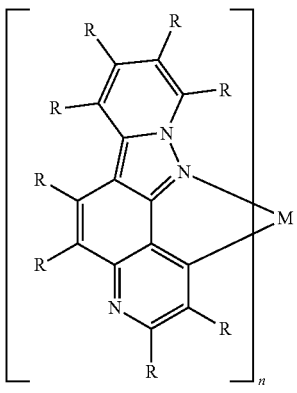
formula (23)
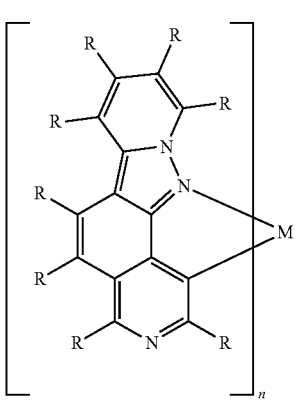
formula (24)
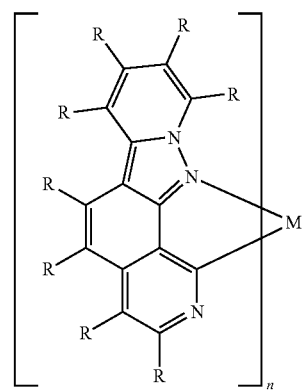
formula (25)
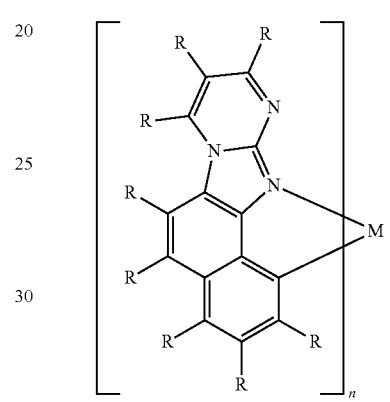
formula (26)
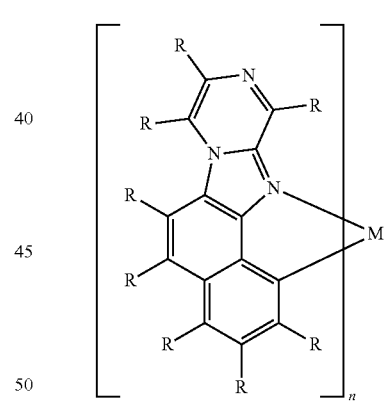
formula (27)
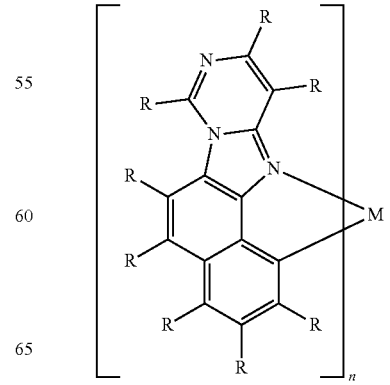

-continued

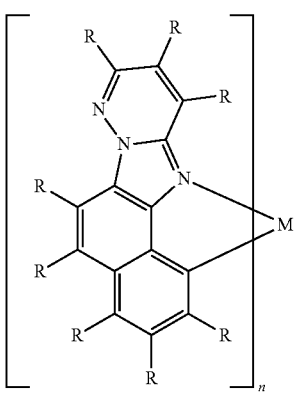
formula (28)

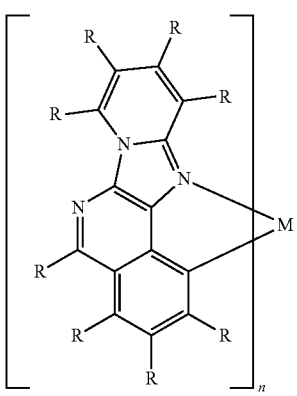
formula (29)

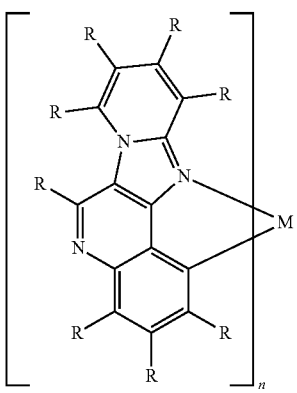
formula (30)

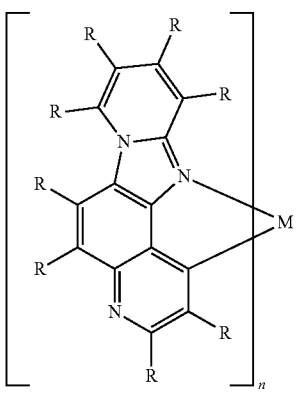
formula (31)

-continued

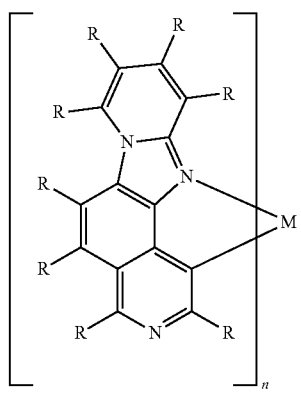
formula (32)

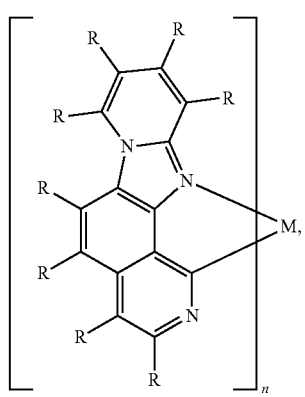
formula (33)

where the following applies to the symbols and indices used:

M is a metal;

Y is on each occurrence, identically or differently, C or N, with the proviso that precisely one symbol Y in each ligand stands for N and the other two symbols Y stand for C;

X is on each occurrence, identically or differently, CR or N;

R is on each occurrence, identically or differently, H, D, F, Cl, Br, I, $N(R^1)_2$, CN, $NO_2$, OH, COOH, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals $R^1$, where one or more non-adjacent $CH_2$ groups is optionally replaced by $R^1C=CR^1$, C≡C, $Si(R^1)_2$, C=O, $NR^1$, O, S or $CONR^1$ and where one or more H atoms is optionally replaced by D, F, Cl, Br, I or CN, or an aromatic or heteroaromatic ring system having 5 to 60 aromatic ring atoms, which may in each case be substituted by one or more radicals $R^1$, or an aryloxy or heteroaryloxy group having 5 to 40 aromatic ring atoms, which is optionally substituted by one or more radicals $R^1$, or an aralkyl or heteroaralkyl group having 5 to 40 aromatic ring atoms, which is optionally substituted by one or more radicals $R^1$, or a diarylamino group, diheteroarylamino group or arylheteroarylamino group having 10 to 40 aromatic ring atoms, which is optionally substituted by one or more radicals $R^1$; two adjacent radicals R here may also form a mono- or polycyclic, aliphatic, aromatic and/or benzo-fused ring system with one another;

$R^1$ is on each occurrence, identically or differently, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals $R^2$, where one or more non-adjacent $CH_2$ groups is optionally replaced by $R^2C=CR^2$, $C\equiv C$, $Si(R^2)_2$, $C=O$, $NR^2$, O, S or $CONR^2$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 40 aromatic ring atoms, which is optionally substituted by one or more radicals $R^2$, or an aralkyl or heteroalkyl group having 5 to 40 aromatic ring atoms, which is optionally substituted by one or more radicals $R^2$, or a diarylamino group, diheteroarylamino group or arylheteroarylamino group having 10 to 40 aromatic ring atoms, which is optionally substituted by one or more radicals $R^2$; two or more adjacent radicals $R^1$ here may form a mono- or polycyclic, aliphatic, aromatic and/or benzo-fused ring system with one another;

$R^2$ is on each occurrence, identically or differently, H, D, F or an aliphatic, aromatic and/or heteroaromatic hydrocarbon radical having 1 to 20 C atoms, in which, in addition, one or more H atoms is optionally replaced by F; two or more substituents $R^2$ here may also form a mono- or polycyclic, aliphatic ring system with one another;

L' is, identically or differently on each occurrence, a co-ligand;

n is 1, 2 or 3;

m is 0, 1, 2, 3 or 4;

a plurality of ligands L here may also be linked to one another or L is optionally linked to L' via any desired bridge V and thus form a tridentate, tetradentate, pentadentate or hexadentate ligand system and/or a substituent R may additionally be coordinated to the metal.

23. An electronic device which comprises the compound according to claim 17.

24. An electronic device which comprises the compound according to claim 22.

25. An organic electroluminescent device which comprises the compound according to claim 17 is employed as emitting compound in one or more emitting layers.

26. An organic electroluminescent device which comprises the compound according to claim 22 is employed as emitting compound in one or more emitting layers.

* * * * *